(12) United States Patent
Kolb et al.

(10) Patent No.: US 8,586,497 B2
(45) Date of Patent: Nov. 19, 2013

(54) POLYMERIZATION CATALYSTS, METHODS OF MAKING, METHODS OF USING, AND POLYOLEFIN PRODUCTS MADE THEREFROM

(75) Inventors: Rainer Kolb, Kingwood, TX (US); Dongming Li, Houston, TX (US); Francis C. Rix, League City, TX (US); Cesar A. Garcia-Franco, Houston, TX (US)

(73) Assignee: Univation Technologies, LLC, Houston, TX (US)

( * ) Notice: Subject to any disclaimer, the term of this patent is extended or adjusted under 35 U.S.C. 154(b) by 127 days.

(21) Appl. No.: 12/741,137

(22) PCT Filed: Nov. 12, 2008

(86) PCT No.: PCT/US2008/012691
§ 371 (c)(1),
(2), (4) Date: May 3, 2010

(87) PCT Pub. No.: WO2009/064404
PCT Pub. Date: May 22, 2009

(65) Prior Publication Data
US 2010/0234547 A1  Sep. 16, 2010

Related U.S. Application Data

(60) Provisional application No. 61/003,181, filed on Nov. 15, 2007.

(51) Int. Cl.
| C08F 4/64 | (2006.01) |
| C08F 4/642 | (2006.01) |
| C08F 4/653 | (2006.01) |
| C08F 4/655 | (2006.01) |
| C08F 210/02 | (2006.01) |

(52) U.S. Cl.
USPC ........... 502/113; 502/103; 502/152; 502/167; 526/113; 526/114; 526/160; 526/161; 526/348; 526/943

(58) Field of Classification Search
USPC ......... 502/102, 133, 152, 171, 103, 113, 167; 526/113, 114, 160, 172, 943, 161, 348
See application file for complete search history.

(56) References Cited

U.S. PATENT DOCUMENTS

| 4,243,619 A | 1/1981 | Fraser et al. |
| 4,354,004 A | 10/1982 | Hughes et al. |
| 4,530,914 A | 7/1985 | Ewen et al. |
| 4,659,685 A | 4/1987 | Coleman et al. |
| 4,937,299 A | 6/1990 | Ewen et al. |
| 5,470,811 A | 11/1995 | Jejelowo et al. |
| 5,516,848 A | 5/1996 | Canich et al. |
| 5,536,796 A | 7/1996 | Jjelowo et al. |
| 5,665,818 A | 9/1997 | Tilston et al. |
| 5,696,045 A | 12/1997 | Winter et al. |
| 5,749,202 A | 5/1998 | Eichbauer |
| 6,143,854 A | 11/2000 | Bamberger et al. |
| 6,232,410 B1 | 5/2001 | Rowland et al. |
| 6,248,845 B1 | 6/2001 | Loveday et al. |
| 6,268,448 B1 | 7/2001 | Collins et al. |
| 6,492,472 B2 | 12/2002 | Lue et al. |
| 6,800,692 B2 | 10/2004 | Farley et al. |
| 6,932,592 B2 | 8/2005 | Farley et al. |
| 6,936,675 B2 | 8/2005 | Szul et al. |
| 6,956,088 B2 | 10/2005 | Farley et al. |
| 7,122,601 B2 | 10/2006 | Musgrave et al. |
| 7,141,632 B2 | 11/2006 | Vaughan et al. |
| 7,163,906 B2 | 1/2007 | McDaniel et al. |
| 7,172,987 B2 | 2/2007 | Kao et al. |
| 7,241,715 B2 * | 7/2007 | Boussie et al. ............... 502/171 |
| 7,312,295 B2 | 12/2007 | Hagen et al. |
| 2004/0010103 A1 | 1/2004 | Boussie et al. |
| 2005/0148744 A1 * | 7/2005 | Kao ............................. 526/114 |
| 2009/0306323 A1 | 12/2009 | Kolb et al. |
| 2010/0261861 A1 | 10/2010 | Kolb et al. |
| 2010/0310892 A1 | 12/2010 | German et al. |

FOREIGN PATENT DOCUMENTS

| EP | 310734 B1 | 11/1994 |
| EP | 516018 B1 | 3/1996 |
| EP | 743327 A2 | 11/1996 |
| EP | 527221 B1 | 9/1997 |
| EP | 1368388 | 12/2003 |
| WO | WO 01/40330 | 6/2001 |
| WO | WO 01/62808 | 8/2001 |
| WO | WO 02/060963 | 8/2002 |
| WO | WO 2006/086104 | 8/2006 |
| WO | WO 2007/035485 | 3/2007 |

* cited by examiner

*Primary Examiner* — Caixia Lu
(74) *Attorney, Agent, or Firm* — Leandro Arechederra, III; Jennifer A. Schmidt

(57) ABSTRACT

Olefin polymerization catalyst systems including a high molecular weight catalyst compound and a low molecular weight catalyst compound, and methods of making same are provided. High molecular weight catalysts include metallocene catalysts and low molecular weight catalysts include non-metallocene compounds including biphenyl phenol compounds. Generally catalyst systems may include less than about 5.0 mol % of the high molecular weight catalyst compound relative to said low molecular weight catalyst. Methods for olefin polymerization including the aforementioned catalyst systems, and polyolefins and products made therefrom.

14 Claims, 7 Drawing Sheets

POLYMERIZATION CATALYSTS, METHODS OF MAKING, METHODS OF USING, AND POLYOLEFIN PRODUCTS MADE THEREFROM

CROSS REFERENCE TO RELATED APPLICATIONS

This application is a National Stage application under 35 U.S.C. §371 for International Application No. PCT/US08/12691, filed on Nov. 12, 2008, that claims the benefit of Ser. No. 61/003,181, filed Nov. 15, 2007, the disclosures of which is incorporated by reference in its entirety.

FIELD OF THE INVENTION

The present disclosure relates generally to polymerization catalysts, methods of using and methods of making said catalysts, and polymers and products made therefrom. More particularly, the present disclosure relates to catalyst systems comprising at least two catalyst components, methods of making said catalyst systems, methods for polymerizing olefins using catalyst systems, and polymers, resins, and articles made therefrom.

BACKGROUND

The use of metallocene compounds in polymerization catalysts, and the use of metallocene catalysts for polymerization are known. However, there remains an ongoing effort to develop metallocene catalysts, polymerization processes using such catalysts, and polyolefin resins and products made therewith, each having advantageous properties and performance.

There are numerous references discussing metallocene catalyst systems comprising at least two catalyst components, wherein at least one component is a metallocene catalyst. For example, U.S. Pat. No. 4,530,914 discusses a catalyst system for producing polyethylene having a broad molecular weight distribution using two different metallocene-type catalyst compounds having different propagation and termination rate constants for ethylene polymerization. U.S. Pat. No. 4,937,299 is directed to a homogeneous catalyst system of at least two metallocene-type catalyst compounds each having different reactivity ratios for use in a single reactor to produce a polymer blend. U.S. Pat. No. 5,470,811 discusses producing polymers having improved product properties using an isomeric mixture of two or more substituted metallocene-type catalyst compounds. EP-A2-0 743 327 discuss the use of meso and racemic bridged mixed metallocene-type catalysts compounds to produce ethylene polymers having improved processability. U.S. Pat. No. 5,516,848 relates to a process for producing polypropylene using a bridged mono-cyclopentadienyl heteroatom containing compound and an unbridged, bis-cyclopentadienyl containing compound. EP-B1-0 310 734 discusses the use of a mixed bridged hafnium and zirconium metallocene-type catalyst compounds to produce a polymer having broad molecular weight distribution. U.S. Pat. No. 5,696,045 describes using at least two different bridged zirconium metallocene-type catalyst compounds to produce propylene polymers having a broad molecular weight distribution where one of the stereorigid zirconocenes has an indenyl ligand having a substituent on the six-member ring. EP-B1-516 018 describes using two different bridged zirconium metallocene-type catalyst compounds to produce a broad molecular weight distribution polypropylene polymer where one of the bridged metallocenes has indenyl ligands that are substituted in at least the two position. U.S. Pat. No. 6,492,472 discusses a catalyst system comprising at least two different metallocene compounds, the system comprising a bridged metallocene catalyst compound and a bridged, asymmetrically substituted, metallocene catalyst compound useful for producing polymers generally having a narrow molecular weight distribution. U.S. Pat. No. 7,141,632 discusses a mixed metallocene catalyst system including a poor comonomer incorporating metallocene catalyst compound and a good comonomer incorporating metallocene catalyst compound useful in producing a more broadly separated bimodal polymer composition. U.S. Pat. No. 7,163,906 discusses a catalyst composition comprising the contact product of at least one metallocene compound and at least one organochromium compound. U.S. Pat. No. 7,172,987 discusses a bimetallic catalyst system comprising a modified Ziegler-Natta catalyst component and a metallocene catalyst component useful for producing bimodal polymers, specifically polyethylene, having a polydispersity of from 12 to 50.

Additionally, there are also references directed to polymerization processes in which two or more polymerization reactors are joined in series, where one catalyst is used in a first reactor to produce a first polymer that is then fed into a second reactor with the same or different catalyst, typically under different reactor conditions. In this way, the resulting polymer from a series polymerization process is a combination or blend of two different polymers. These polymer blends, typically, contain a high molecular weight and a low molecular weight component. For example, U.S. Pat. No. 5,665,818 discusses using two fluidized gas phase reactors in series using a transition metal based catalyst to form an in situ polymer blend having improved extrudability. EP-B1-0 527 221 discusses a series reactor process using metallocene-type catalyst systems for producing bimodal molecular weight distribution polymer products. However, series or multistage reactor processes are expensive and more difficult to operate.

However, there remains a need for catalyst systems with good reactor operability. There is also a need for catalyst systems for producing bimodal polyolefin compositions. There is even another need in the art for methods of polymerizing bimodal polyolefin, preferably, in a single reactor, having good processability. There is yet another need for olefin polymers and polyolefin products having enhanced properties. These and other limitations may be overcome with the catalysts, methods, polymers, and products of the present disclosure.

SUMMARY

The following presents a general summary of some of the many possible embodiments of this disclosure in order to provide a basic understanding of this disclosure. This summary is not an extensive overview of all embodiments of the disclosure. This summary is not intended to identify key or critical elements of the disclosure or to delineate or otherwise limit the scope of the claims. The following summary merely presents some concepts of the disclosure in a general form as a prelude to the more detailed description that follows.

According to one embodiment there is provided a catalyst system comprising a first catalyst compound and a second catalyst compound, wherein said first catalyst compound is a metallocene, and wherein said second catalyst compound has the following Structure I:

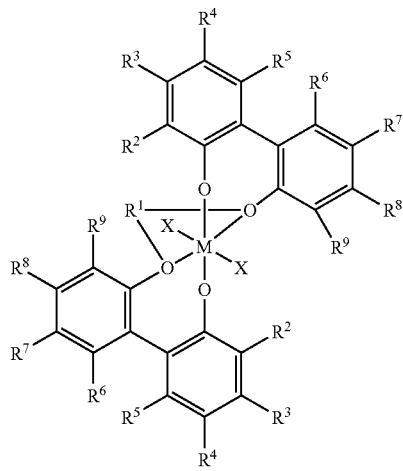

Structure I wherein M is a Group 4 metal (IUPAC; new notation), for example, M may be Ti, Zr, or Hf; each $R^1$ through $R^9$ may be any of hydrides, halides, alkyls or aryls, wherein the alkyls or aryls may optionally be substituted; and X is at least one leaving group, for example, X may be any of F, Cl, Br, I, Me, Bnz, $CH_2SiMe_3$, or $C_1$ to $C_5$ alkyls; and optionally a cocatalyst.

According to another embodiment there is provided a catalyst system comprising a first catalyst compound that when used in a polymerization reaction produces a first polymer having a weight average molecular weight (Mw) in the range of from 40,000 to 200,000 g/mol, and a second catalyst compound that when used in a polymerization reaction produces a second polymer having an Mw of greater than 1,000,000 g/mol, and a cocatalyst compound. Generally the catalyst system when used in a polymerization reaction produces a polymer product comprising said first and second polymers, wherein said polymer product comprises at least one of the following properties: (i) a melt strength value greater than $6*MI^{-0.6675}$ and wherein MI is the melt index value of said polymer product measured in accordance with ASTM-D-1238-E, (ii) a ratio of extensional viscosity measured at a strain rate of 1 $sec^{-1}$, 190° C., and time=4 seconds to that predicted by linear viscoelasticity at the same temperature and time of greater than 3, (iii) an activation energy ($E_a$) of less than 7 kcal/mol/K, and (iv) a Mz/Mw ratio greater than the Mw/Mn ratio, wherein Mz is the z-average molecular weight of said polymer product, Mw is the weight average molecular weight of said polymer product, Mn is the number average molecular weight of said polymer product; and v) a van Gurp-Palmen plot comprising a positive slope and possessing a maximum, wherein the van Gurp-Palmen plot is a plot of the phase angle versus the absolute value of the complex shear modulus determined from dynamic rheology, more particularly, from frequency sweeps in the range from 0.01 to 100 rad/s at 190° C.

According to even another embodiment there is provided a method for making a catalyst system comprising: contacting in a diluent (a) a first compound wherein said compound is a metallocene; and (b) a second compound having the following Structure I:

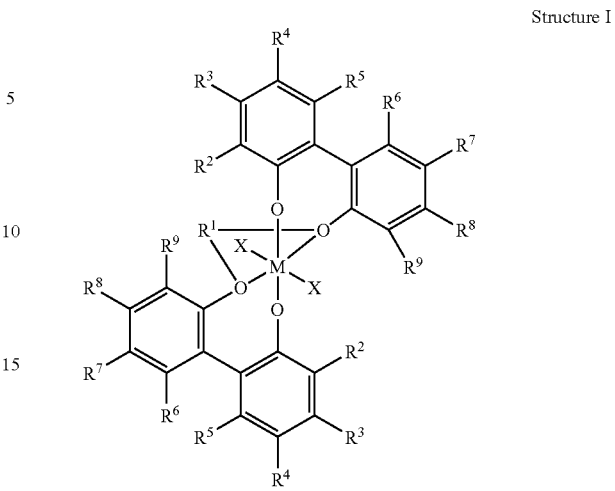

Structure I wherein M is a Group 4 metal (IUPAC; new notation), for example, M may be Ti, Zr, or Hf; each $R^1$ through $R^9$ may be any of hydrides, halides, alkyls or aryls, wherein the alkyls or aryls may optionally be substituted; and X is at least one leaving group, for example, X may be any of F, Cl, Br, I, Me, Bnz, $CH_2SiMe_3$, or $C_1$ to $C_5$ alkyls; and (c) a cocatalyst to form the catalyst system.

According to still another embodiment there is provided a method for olefin polymerization comprising: contacting two or more olefin monomers with a catalyst system under olefin polymerization conditions to create a polyolefin wherein said catalyst system comprises a first catalyst component and a second catalyst component, wherein said first catalyst component is a metallocene; and wherein said second catalyst component has the following Structure I:

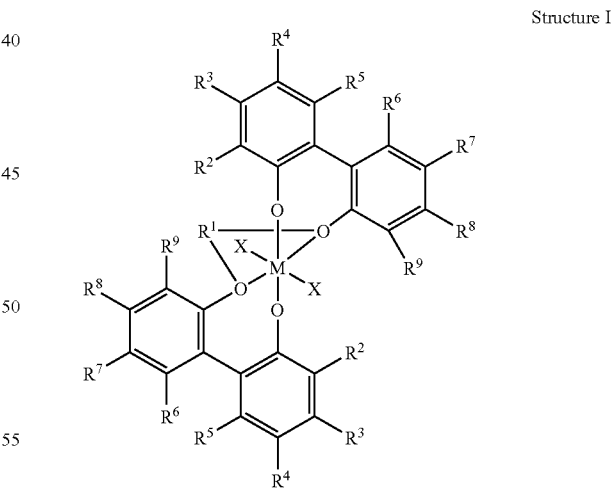

Structure I wherein M is a Group 4 (IUPAC; new notation) metal, for example, M may be Ti, Zr, or Hf; each $R^1$ through $R^9$ may be any of hydrides, halides, alkyls or aryls, wherein the alkyls or aryls may optionally be substituted; and X is at least one leaving group, for example, X is at least one leaving group, for example, X may be any of F, Cl, Br, I, Me, Bnz, $CH_2SiMe_3$, or $C_1$ to $C_5$ alkyls; and wherein said first catalyst component produces polymer having a weight average molecular weight (Mw) in the range of from 40,000 to 200, 000 g/mol, and said second catalyst component produces polymer having an Mw of greater than 1,000,000 g/mol.

According to even still another embodiment there is provided a method for producing polyethylene comprising the steps of: mixing a first polyethylene having a weight average molecular weight (Mw) of greater than 1,000,000 g/mol together and a second polyethylene having an Mw in the range of 40,000 to 200,000 g/mol in a solvent to produce a bimodal polyethylene solution; and precipitating said bimodal polyethylene out of said solution, wherein said bimodal polyethylene comprises at least one of the following properties: (i) a melt strength value greater than $6*MI^{-0.6675}$, wherein MI is the melt index value measured in accordance with ASTM-D-1238-E, (ii) a ratio of extensional viscosity measured at a strain rate of 1 $sec^{-1}$, 190° C., and time=4 seconds to that predicted by linear viscoelasticity at the same temperature and time of greater than 3, (iii) an activation energy ($E_a$) of less than 7 kcal/mol/K, and (iv) a Mz/Mw ratio greater than the Mw/Mn ratio, wherein Mz is the z-average molecular weight of said polyethylene, Mw is the weight average molecular weight of said polyethylene, Mn is the number average molecular weight of said polyethylene; and v) a van Gurp-Palmen plot comprising a positive slope and possessing a maximum, wherein the van Gurp-Palmen plot is a plot of the phase angle versus the absolute value of the complex shear modulus determined from dynamic rheology, more particularly, from frequency sweeps in the range from 0.01 to 100 rad/s at 190° C. Generally the step of mixing comprises dissolving the first and second polymers in the solvent.

According to even yet another embodiment there is provided an ethylene polymer comprising at least one of the following properties: (i) melt strength value greater than $6*MI^{0.6675}$, wherein MI is the melt index value of said polymer measured in accordance with ASTM-D-1238-E, (ii) a ratio of extensional viscosity measured at a strain rate of 1 $sec^{-1}$, 190° C., and time=4 seconds to that predicted by linear viscoelasticity at the same temperature and time of greater than 3, (iii) an activation energy ($E_a$) of less than 7 kcal/mol/ K, and (iv) a Mz/Mw ratio greater than the Mw/Mn ratio, wherein Mz is the z-average molecular weight of said polymer, Mw is the weight average molecular weight of said polymer, Mn is the number average molecular weight of said polymer; and v) a van Gurp-Palmen plot comprising a positive slope and possessing a maximum, wherein the van Gurp-Palmen plot is a plot of the phase angle versus the absolute value of the complex shear modulus determined from dynamic rheology, more particularly, from frequency sweeps in the range from 0.01 to 100 rad/s at 190° C.

According to still even another embodiment there is provided an article produced from an ethylene polymer comprising at least one of the following properties: (i) melt strength value greater than $6*MI^{-0.6675}$, wherein MI is the melt index value of said polymer measured in accordance with ASTM D-1238-E, (ii) a ratio of extensional viscosity measured at a strain rate of 1 $sec^{-1}$, 190° C., and time=4 seconds to that predicted by linear viscoelasticity at the same temperature and time of greater than 3, (iii) an activation energy ($E_a$) of less than 7 kcal/mol/K, and (iv) a Mz/Mw ratio greater than the Mw/Mn ratio, wherein Mz is the z-average molecular weight of said polymer, Mw is the weight average molecular weight of said polymer, Mn is the number average molecular weight of said polymer; and v) a van Gurp-Palmen plot comprising a positive slope and possessing a maximum, wherein the van Gurp-Palmen plot is a plot of the phase angle versus the absolute value of the complex shear modulus determined from dynamic rheology, more particularly, from frequency sweeps in the range from 0.01 to 100 rad/s at 190° C.

BRIEF DESCRIPTION OF THE DRAWINGS

The following drawings illustrate some of the many possible embodiments of this disclosure in order to provide a basic understanding of the present disclosure. These drawings do not provide an extensive overview of all embodiments of this disclosure. These drawings are not intended to identify key or critical elements of the disclosure or to delineate or otherwise limit the scope of the claims. The following drawings merely present some concepts of the disclosure in a general form. Thus, for a detailed understanding of this disclosure, reference should be made to the following detailed description, taken in conjunction with the accompanying drawings, in which like elements have been given like numerals.

DETAILED DESCRIPTION

Figure 1:
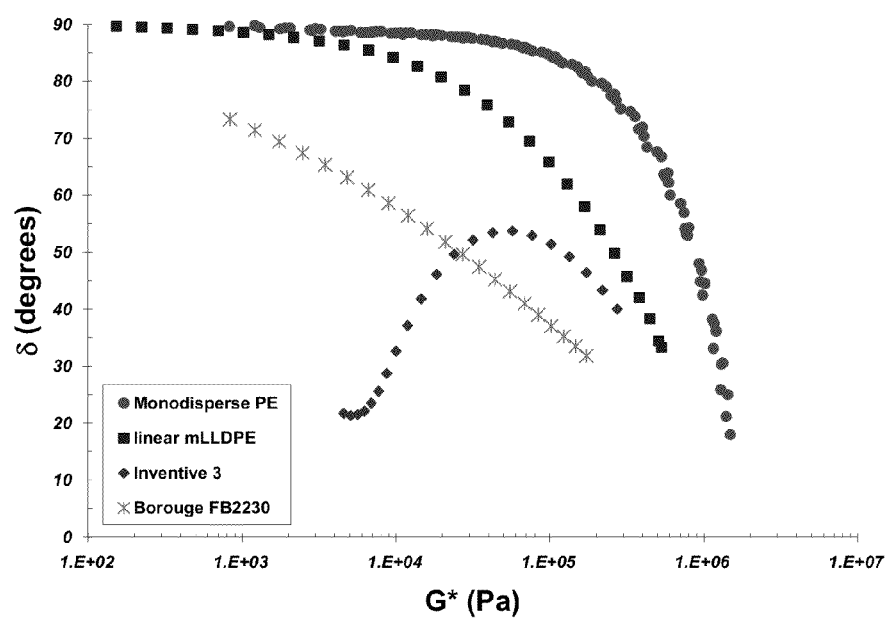
FIG. 1 provides a comparison of Van Gurp-Palmen plots of non-limiting example resins of the disclosure and conventional resins.

Before the present compounds, components, compositions, and/or methods are disclosed and described, it is to be understood that unless otherwise indicated this invention is not limited to specific compounds, components, compositions, reactants, reaction conditions, ligands, metallocene structures, or the like, as such may vary, unless otherwise specified. It is also to be understood that the terminology used herein is for the purpose of describing particular embodiments only and is not intended to be limiting.

It must also be noted that, as used in the specification and the appended claims, the singular forms "a," "an," and "the" include plural referents unless otherwise specified. Thus, for example, reference to "a leaving group" as in a moiety "substituted with a leaving group" includes more than one leaving group, such that the moiety may be substituted with two or more such groups. Similarly, reference to "a halogen atom" as in a moiety "substituted with a halogen atom" includes more than one halogen atom, such that the moiety may be substituted with two or more halogen atoms, reference to "a substituent" includes one or more substituents, reference to "a ligand" includes one or more ligands, and the like.

The present disclosure provides catalyst systems for olefin polymerization, methods of making and method of using said catalyst systems, and polymer and products made therewith. The catalyst systems of the disclosure comprise at least two catalyst components—a first catalyst compound and a second catalyst compound. The catalyst systems may further comprise one or more additional catalyst compounds. Any two or more catalyst systems of the disclosure may be combined to produce a catalyst system of the disclosure. The terms "mixed catalyst system" and "mixed catalyst" may be used interchangeably herein with "catalyst system."

The catalyst systems of the present disclosure comprise a first catalyst component that produces generally low molecular weight polyolefin, and a second catalyst component that produces generally high molecular weight polyolefin. As known by one of skill in the art, although the precise molecular weight of a polyolefin produced by a polymerization catalyst in a polymerization reaction is dependent upon reaction conditions including, but not limited to, reaction temperature, hydrogen concentration, and comonomer concentration, catalysts can be described by the general molecular weight of the polyolefin they produce under standard reactor conditions, or a range of standard reactor conditions. The first catalyst component that produces low molecular weight polyolefin may be referred to herein as a "low molecular weight catalyst". The second catalyst component that produces generally high molecular weight polyolefin may be referred to herein as a "high molecular weight catalyst". It should be understood that the molecular weight is in reference to the polymer produced by the catalyst and not the molecular weight of the catalyst itself.

As used herein, "low molecular weight" is defined to be a weight average molecular weight (Mw) in the range of from about 40,000 to about 200,000 g/mol, preferably from about 50,000 to about 180,000 g/mol, more preferably from about 60,000 to about 175,000 g/mol, and even more preferably from about 70,000 to about 150,000 g/mol. In one non-limiting embodiment, low molecular weight is about 100,000 g/mol. As used herein, "high molecular weight" is defined as a weight average molecular weight (Mw) greater than about 1 million g/mol, preferably greater than about 1.5 million g/mol, even more preferably greater than about 2 million g/mol, and still more preferably greater than about 3 million g/mol. In one non-limiting embodiment, high molecular weight is about 5 million g/mol.

In one non-limiting embodiment of the disclosure, the low molecular weight catalyst component is a metallocene compound, and the high molecular weight catalyst is a non-metallocene compound. In another non-limiting example the low molecular weight component is a Group 15 containing compound. In another non-limiting example the low molecular weight component is a phenoxide transition metal composition. In another non-limiting example the low molecular weight component is a Group 5 or 6 metal imido complex. In another non-limiting example the low molecular weight component is a bridged bis(arylamido) Group 4 compound. In another non-limiting example the low molecular weight component is a derivatives of a metallocene or a phenoxide transition metal composition or a group 5 or 6 metal imido complex or a bridged bis(arylamido) Group 4 compound. In another non-limiting example, the low molecular weight component is any combination of metallocene and a phenoxide transition metal composition and a Group 5 or 6 metal imido complex and a bridged bis(arylamido) Group 4 compound.

As used herein, the phrase "characterized by the formula" is not intended to be limiting and is used in the same way that "comprising" is commonly used. The term "independently selected" is used herein to indicate that the R groups, e.g., $R^1$, $R^2$, $R^3$, $R^4$, and $R^5$ can be identical or different (e.g. $R^1$, $R^2$, $R^3$, $R^4$, and $R^5$ may all be substituted alkyls or $R^1$ and $R^2$ may be a substituted alkyl and $R^3$ may be an aryl, etc.). Use of the singular includes use of the plural and vice versa (e.g., a hexane solvent, includes hexanes). A named R group will generally have the structure that is recognized in the art as corresponding to R groups having that name.

The terms "compound" and "complex" are generally used interchangeably in this specification, but those of skill in the art may recognize certain compounds as complexes and vice versa.

The terms "precatalyst", "catalyst", "precatalyst metal compound", "catalyst metal compound", "catalyst component" are generally used interchangeably in this specification, but those of skill in the art may recognize certain precatalysts as catalysts and vice versa.

The terms "monomer" and "comonomer" are generally used interchangeably in this specification, but those of skill in the art may recognize certain monomers as comonomers and vice versa.

For the purposes of illustration, representative certain groups are defined herein. These definitions are intended to supplement and illustrate, not preclude, the definitions known to those of skill in the art. "Optional" or "optionally" means that the subsequently described event or circumstance may or may not occur, and that the description includes instances where said event or circumstance occurs and instances where it does not. For example, the phrase "optionally substituted hydrocarbyl" means that a hydrocarbyl moiety may or may not be substituted and that the description includes both unsubstituted hydrocarbyl and hydrocarbyl where there is substitution.

The term "alkyl" as used herein refers to a branched or unbranched saturated hydrocarbon group typically although not necessarily containing 1 to about 50 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although again not necessarily, alkyl groups herein may contain 1 to about 12 carbon atoms. The term "lower alkyl" intends an alkyl group of one to six carbon atoms, specifically one to four carbon atoms. The term alkyl also refers to divalent alkyls such as —$CR_2$— which may be referred to as alkylenes or hydrocarbylenes and may be substituted with one or more substituent groups or heteroatom containing groups. "Substituted alkyl" refers to alkyl substituted with one or more substituent groups (e.g., benzyl or chloromethyl), and the terms "heteroatom-containing alkyl" and "heteroalkyl" refer to alkyl in which at least one carbon atom is replaced with a heteroatom (e.g., —$CH_2OCH_3$ is an example of a heteroalkyl).

The term "alkenyl" as used herein refers to a branched or unbranched hydrocarbon group typically although not necessarily containing 2 to about 50 carbon atoms and at least one double bond, such as ethenyl, n-propenyl, isopropenyl, n-butenyl, isobutenyl, octenyl, decenyl, and the like. Generally, although again not necessarily, alkenyl groups herein contain 2 to about 12 carbon atoms. The term "lower alkenyl" intends an alkenyl group of two to six carbon atoms, specifically two to four carbon atoms. "Substituted alkenyl" refers to alkenyl substituted with one or more substituent groups, and the terms "heteroatom-containing alkenyl" and "heteroalkenyl" refer to alkenyl in which at least one carbon atom is replaced with a heteroatom.

The term "alkynyl" as used herein refers to a branched or unbranched hydrocarbon group typically although not necessarily containing 2 to about 50 carbon atoms and at least one triple bond, such as ethynyl, n-propynyl, isopropynyl, n-butynyl, isobutynyl, octynyl, decynyl, and the like. Generally, although again not necessarily, alkynyl groups herein may have 2 to about 12 carbon atoms. The term "lower alkynyl" intends an alkynyl group of two to six carbon atoms, specifically three or four carbon atoms. "Substituted alkynyl" refers to alkynyl substituted with one or more substituent groups, and the terms "heteroatom-containing alkynyl" and "heteroalkynyl" refer to alkynyl in which at least one carbon atom is replaced with a heteroatom.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group having one to six, more specifically one to four, carbon atoms. The term "aryloxy" is used in a similar fashion, with aryl as defined below. The term "hydroxy" refers to —OH.

Similarly, the term "alkylthio" as used herein intends an alkyl group bound through a single, terminal thioether linkage; that is, an "alkylthio" group may be represented as —S-alkyl where alkyl is as defined above. A "lower alkyl thio" group intends an alkyl thio group having one to six, more specifically one to four, carbon atoms. The term "arylthio" is used similarly, with aryl as defined below. The term "thioxy" refers to —SH.

The term "aryl" as used herein, and unless otherwise specified, refers to an aromatic substituent containing a single aromatic ring or multiple aromatic rings that are fused together, linked covalently, or linked to a common group such as a methylene or ethylene moiety. More specific aryl groups contain one aromatic ring or two or three fused or linked aromatic rings, e.g., phenyl, naphthyl, biphenyl, anthracenyl, phenanthrenyl, and the like. In particular embodiments, aryl substituents have 1 to about 200 carbon atoms, typically 1 to about 50 carbon atoms, and specifically 1 to about 20 carbon atoms. "Substituted aryl" refers to an aryl moiety substituted with one or more substituent groups, (e.g., tolyl, mesityl and perfluorophenyl) and the terms "heteroatom-containing aryl" and "heteroaryl" refer to aryl in which at least one carbon atom is replaced with a heteroatom (e.g., rings such as thiophene, pyridine, isoxazole, pyrazole, pyrrole, furan, etc. or benzo-fused analogues of these rings are included in the term "heteroaryl"). In some embodiments herein, multi-ring moieties are substituents and in such an embodiment the multi-ring moiety can be attached at an appropriate atom. For example, "naphthyl" can be 1-naphthyl or 2-naphthyl; "anthracenyl" can be 1-anthracenyl, 2-anthracenyl or 9-anthracenyl; and "phenanthrenyl" can be 1-phenanthrenyl, 2-phenanthrenyl, 3-phenanthrenyl, 4-phenanthrenyl or 9-phenanthrenyl.

The term "aralkyl" refers to an alkyl group with an aryl substituent, and the term "aralkylene" refers to an alkylene group with an aryl substituent; the term "alkaryl" refers to an aryl group that has an alkyl substituent, and the term "alkarylene" refers to an arylene group with an alkyl substituent.

The terms "halo" and "halogen" and "halide" are used in the conventional sense to refer to a chloro, bromo, fluoro or iodo substituent. The terms "haloalkyl," "haloalkenyl" or "haloalkynyl" (or "halogenated alkyl," "halogenated alkenyl," or "halogenated alkynyl") refers to an alkyl, alkenyl or alkynyl group, respectively, in which at least one of the hydrogen atoms in the group has been replaced with a halogen atom.

The term "heteroatom-containing" as in a "heteroatom-containing hydrocarbyl group" refers to a molecule or molecular fragment in which one or more carbon atoms is replaced with an atom other than carbon, e.g., nitrogen, oxygen, sulfur, phosphorus, boron or silicon. Similarly, the term "heteroalkyl" refers to an alkyl substituent that is heteroatom-containing, the term "heterocyclic" refers to a cyclic substituent that is heteroatom-containing, the term "heteroaryl" refers to an aryl substituent that is heteroatom-containing, and the like. When the term "heteroatom-containing" appears prior to a list of possible heteroatom-containing groups, it is intended that the term apply to every member of that group. That is, the phrase "heteroatom-containing alkyl, alkenyl and alkynyl" is to be interpreted as "heteroatom-containing alkyl, heteroatom-containing alkenyl and heteroatom-containing alkynyl."

"Hydrocarbyl" refers to hydrocarbyl radicals containing 1 to about 50 carbon atoms, specifically 1 to about 24 carbon atoms, most specifically 1 to about 16 carbon atoms, including branched or unbranched, saturated or unsaturated species, such as alkyl groups, alkenyl groups, aryl groups, and the like. The term "lower hydrocarbyl" intends a hydrocarbyl group of one to six carbon atoms, specifically one to four carbon atoms. "Substituted hydrocarbyl" refers to hydrocarbyl substituted with one or more substituent groups, and the terms "heteroatom-containing hydrocarbyl" and "heterohydrocarbyl" refer to hydrocarbyl in which at least one carbon atom is replaced with a heteroatom.

By "substituted" as in "substituted hydrocarbyl," "substituted aryl," "substituted alkyl," "substituted alkenyl" and the like, as alluded to in some of the aforementioned definitions, is meant that in the hydrocarbyl, hydrocarbylene, alkyl, alkenyl, aryl or other moiety, at least one hydrogen atom bound to a carbon atom is replaced with one or more substituents that are functional groups such as hydroxyl, alkoxy, alkylthio, phosphino, amino, halo, silyl, and the like. When the term "substituted" appears prior to a list of possible substituted groups, it is intended that the term apply to every member of that group. That is, the phrase "substituted alkyl, alkenyl and alkynyl" is to be interpreted as "substituted alkyl, substituted alkenyl and substituted alkynyl." Similarly, "optionally substituted alkyl, alkenyl and alkynyl" is to be interpreted as "optionally substituted alkyl, optionally substituted alkenyl and optionally substituted alkynyl."

By "divalent" as in "divalent hydrocarbyl", "divalent alkyl", "divalent aryl" and the like, is meant that the hydrocarbyl, alkyl, aryl or other moiety is bonded at two points to atoms, molecules or moieties with the two bonding points being covalent bonds. The term "aromatic" is used in its usual sense, including unsaturation that is essentially delocalized across multiple bonds, such as around a ring.

As used herein the term "silyl" refers to the $-SiZ^1Z^2Z^3$ radical, where each of $SiZ^1Z^2Z^3$ is independently selected from the group consisting of hydride and optionally substituted alkyl, alkenyl, alkynyl, heteroatom-containing alkyl, heteroatom-containing alkenyl, heteroatom-containing alkynyl, aryl, heteroaryl, alkoxy, aryloxy, amino, silyl and combinations thereof.

As used herein the term "boryl" refers to the $-BZ^1Z^2$ group, where each of $Z^1$ and $Z^2$ is as defined above. As used herein, the term "phosphino" refers to the group $-PZ^1Z^2$, where each of $Z^1$ and $Z^2$ is as defined above. As used herein, the term "phosphine" refers to the group: $PZ^1Z^2Z^3$, where each of $Z^1$, $Z^2$, $Z^3$ as defined above. The term "amino" is used herein to refer to the group $-NZ^1Z^2$, where each of $Z^1$ and $Z^2$ is as defined above. The term "amine" is used herein to refer to the group: $NZ^1Z^2Z^3$, where each of $Z^1$, $Z^2$, $Z^3$ is as defined above.

The term "saturated" refers to lack of double and triple bonds between atoms of a radical group such as ethyl, cyclohexyl, pyrrolidinyl, and the like. The term "unsaturated" refers to the presence of one or more double and triple bonds between atoms of a radical group such as vinyl, acetylide, oxazolinyl, cyclohexenyl, acetyl and the like.

Metallocene Catalysts

The catalyst system may include at least one metallocene catalyst component. The metallocene catalyst component may include "half sandwich" and "full sandwich" compounds having one or more Cp ligands (cyclopentadienyl and ligands isolobal to cyclopentadienyl) bound to at least one Group 3 to Group 12 metal atom, and one or more leaving group(s) bound to the at least one metal atom. Hereinafter, these compounds will be referred to as "metallocenes" or "metallocene catalyst components".

In one aspect, the one or more metallocene catalyst components are represented by the formula (I):

$$Cp^A Cp^B MX_n \qquad (I)$$

The metal atom "M" of the metallocene catalyst compound, as described throughout the specification and claims, may be selected from the group consisting of Groups 3 through 12 atoms and lanthanide Group atoms in one embodiment; and selected from the group consisting of Groups 3 through 10 atoms in a more particular embodiment, and selected from the group consisting of Sc, Ti, Zr, Hf, V, Nb, Ta, Mn, Re, Fe, Ru, Os, Co, Rh, Ir, and Ni in yet a more particular embodiment; and selected from the group consisting of Groups 4, 5 and 6 atoms in yet a more particular embodiment, and a Ti, Zr, Hf atoms in yet a more particular embodiment, and Zr in yet a more particular embodiment. The oxidation state of the metal atom "M" may range from 0 to +7 in one embodiment; and in a more particular embodiment, is +1, +2, +3, +4 or +5; and in yet a more particular embodiment is +2, +3 or +4. The groups bound the metal atom "M" is such that the compounds described below in the formulas and structures are neutral, unless otherwise indicated. The Cp ligand(s) form at least one chemical bond with the metal atom M to form the "metallocene catalyst compound". The Cp ligands are distinct from the leaving groups bound to the catalyst compound in that they are not highly susceptible to substitution/abstraction reactions.

M is as described above; each X is chemically bonded to M; each Cp group is chemically bonded to M; and n is 0 or an integer from 1 to 4, and either 1 or 2 in a particular embodiment.

The ligands represented by $Cp^A$ and $Cp^B$ in formula (I) may be the same or different cyclopentadienyl ligands or ligands isolobal to cyclopentadienyl, either or both of which may contain heteroatoms and either or both of which may be substituted by a group R. In one embodiment, $Cp^A$ and $Cp^B$ are independently selected from the group consisting of cyclopentadienyl, indenyl, tetrahydroindenyl, fluorenyl, and substituted derivatives of each.

Independently, each $Cp^A$ and $Cp^B$ of formula (I) may be unsubstituted or substituted with any one or combination of substituent groups R. Non-limiting examples of substituent groups R as used in structure (I) include hydrogen radicals, hydrocarbyls, lower hydrocarbyls, substituted hydrocarbyls, heterohydrocarbyls, alkyls, lower alkyls, substituted alkyls, heteroalkyls, alkenyls, lower alkenyls, substituted alkenyls, heteroalkenyls, alkynyls, lower alkynyls, substituted alkynyls, heteroalkynyls, alkoxys, lower alkoxys, aryloxys, hydroxyls, alkylthios, lower alkyls thios, arylthios, thioxys, aryls, substituted aryls, heteroaryls, aralkyls, aralkylenes, alkaryls, alkarylenes, halides, haloalkyls, haloalkenyls, haloalkynyls, heteroalkyls, heterocycles, heteroaryls, heteroatom-containing groups, silyls, boryls, phosphinos, phosphines, aminos, amines, cycloalkyls, acyls, aroyls, alkylthiols, dialkylamines, alkylamidos, alkoxycarbonyls, aryloxycarbonyls, carbomoyls, alkyl- and dialkyl-carbamoyls, acyloxys, acylaminos, aroylaminos, and combinations thereof.

More particular non-limiting examples of alkyl substituents R associated with formula (I) includes methyl, ethyl, propyl, butyl, pentyl, hexyl, cyclopentyl, cyclohexyl, benzyl, phenyl, methylphenyl, and tert-butylphenyl groups and the like, including all their isomers, for example tertiary-butyl, isopropyl, and the like. Other possible radicals include substituted alkyls and aryls such as, for example, fluoromethyl, fluoroethyl, difluoroethyl, iodopropyl, bromohexyl, chlorobenzyl and hydrocarbyl substituted organometalloid radicals including trimethylsilyl, trimethylgermyl, methyldiethylsilyl and the like; and halocarbyl-substituted organometalloid radicals including tris(trifluoromethyl)silyl, methylbis(difluoromethyl)silyl, bromomethyldimethylgermyl and the like; and disubstituted boron radicals including dimethylboron for example; and disubstituted Group 15 radicals including dimethylamine, dimethylphosphine, diphenylamine, methylphenylphosphine, Group 16 radicals including methoxy, ethoxy, propoxy, phenoxy, methylsulfide and ethylsulfide. Other substituents R include olefins such as but not limited to olefinically unsaturated substituents including vinyl-terminated ligands, for example 3-butenyl, 2-propenyl, 5-hexenyl and the like. In one embodiment, at least two R groups, two adjacent R groups in one embodiment, are joined to form a ring structure having from 3 to 30 atoms selected from the group consisting of carbon, nitrogen, oxygen, phosphorous, silicon, germanium, aluminum, boron and combinations thereof. Also, a substituent group R group such as 1-butanyl may form a bonding association to the element M.

Each X in formula (I) is independently selected from the group consisting of: any leaving group in one embodiment; halogen ions, hydrides, hydrocarbyls, lower hydrocarbyls, substituted hydrocarbyls, heterohydrocarbyls, alkyls, lower alkyls, substituted alkyls, heteroalkyls, alkenyls, lower alkenyls, substituted alkenyls, heteroalkenyls, alkynyls, lower alkynyls, substituted alkynyls, heteroalkynyls, alkoxys, lower alkoxys, aryloxys, hydroxyls, alkylthios, lower alkyls thios, arylthios, thioxys, aryls, substituted aryls, heteroaryls, aralkyls, aralkylenes, alkaryls, alkarylenes, halides, haloalkyls, haloalkenyls, haloalkynyls, heteroalkyls, heterocycles, heteroaryls, heteroatom-containing groups, silyls, boryls, phosphinos, phosphines, aminos, amines, cycloalkyls, acyls, aroyls, alkylthiols, dialkylamines, alkylamidos, alkoxycarbonyls, aryloxycarbonyls, carbomoyls, alkyl- and dialkyl-carbamoyls, acyloxys, acylaminos, aroylaminos, and combinations thereof. In another embodiment, X is $C_1$ to $C_{12}$ alkyls, $C_2$ to $C_{12}$ alkenyls, $C_6$ to $C_{12}$ aryls, $C_7$ to $C_{20}$ alkylaryls, $C_1$ to $C_{12}$ alkoxys, $C_6$ to $C_{16}$ aryloxys, $C_7$ to $C_{18}$ alkylaryloxys, $C_1$ to $C_{12}$ fluoroalkyls, $C_6$ to $C_{12}$ fluoroaryls, and $C_1$ to $C_{12}$ heteroatom-containing hydrocarbons and substituted derivatives thereof in a more particular embodiment; hydride, halogen ions, $C_1$ to $C_6$ alkyls, $C_2$ to $C_6$ alkenyls, $C_7$ to $C_{18}$ alkylaryls, $C_1$ to $C_6$ alkoxys, $C_6$ to $C_{14}$ aryloxys, $C_7$ to $C_{16}$ alkylaryloxys, $C_1$ to $C_6$ alkylcarboxylates, $C_1$ to $C_6$ fluorinated alkylcarboxylates, $C_6$ to $C_{12}$ arylcarboxylates, $C_7$ to $C_{18}$ alkylarylcarboxylates, $C_1$ to $C_6$ fluoroalkyls, $C_2$ to $C_6$ fluoroalkenyls, and $C_7$ to $C_{18}$ fluoroalkylaryls in yet a more particular embodiment; hydride, chloride, fluoride, methyl, phenyl, phenoxy, benzoxy, tosyl, fluoromethyls and fluorophenyls in yet a more particular embodiment; $C_1$ to $C_{12}$ alkyls, $C_2$ to $C_{12}$ alkenyls, $C_6$ to $C_{12}$ aryls, $C_7$ to $C_{20}$ alkylaryls, substituted $C_1$ to $C_{12}$ alkyls, substituted $C_6$ to $C_{12}$ aryls, substituted $C_7$ to $C_{20}$ alkylaryls and $C_1$ to $C_{12}$ heteroatom-containing alkyls, $C_1$ to $C_{12}$ heteroatom-containing aryls and $C_1$ to $C_{12}$ heteroatom-containing alkylaryls in yet a more particular embodiment; chloride, fluoride, $C_1$ to $C_6$ alkyls, $C_2$ to $C_6$ alkenyls, $C_7$ to $C_{18}$ alkylaryls, halogenated $C_1$ to $C_6$ alkyls, halogenated $C_2$ to $C_6$ alkenyls, and halogenated $C_7$ to $C_{18}$ alkylaryls in yet a more particular embodiment; fluoride, methyl, ethyl, propyl, phenyl, methylphenyl, dimethylphenyl, trimethylphenyl, fluoromethyls (mono-, di- and trifluoromethyls) and fluorophenyls (mono-, di-, tri-, tetra- and pentafluorophenyls) in yet a more particular embodiment.

Other non-limiting examples of X groups in formula (I) include amines, phosphines, ethers, carboxylates, dienes, hydrocarbon radicals having from 1 to 20 carbon atoms, fluorinated hydrocarbon radicals (e.g., —$C_6F_5$ (pentafluorophenyl)), fluorinated alkylcarboxylates (e.g., $CF_3C(O)O^-$), hydrides and halogen ions and combinations thereof. Other examples of X ligands include alkyl groups such as cyclobutyl, cyclohexyl, methyl, heptyl, tolyl, trifluoromethyl, tetramethylene, pentamethylene, methylidene, methyoxy, ethyoxy, propoxy, phenoxy, bis(N-methylanilide), dimethylamide, dimethylphosphide radicals and the like. In one embodiment, two or more X's form a part of a fused ring or ring system.

In another aspect, the metallocene catalyst component includes those of formula (I) where $Cp^A$ and $Cp^B$ are bridged to each other by at least one bridging group, (A), such that the structure is represented by formula (II):

$$Cp^A(A)Cp^B MX_n \qquad (II)$$

These bridged compounds represented by formula (II) are known as "bridged metallocenes". $Cp^A$, $Cp^B$, M, X and n are as defined above for formula (I); and wherein each Cp ligand is chemically bonded to M, and (A) is chemically bonded to each Cp. Non-limiting examples of bridging group (A) include divalent alkyls, divalent lower alkyls, divalent substituted alkyls, divalent heteroalkyls, divalent alkenyls, divalent lower alkenyls, divalent substituted alkenyls, divalent heteroalkenyls, divalent alkynyls, divalent lower alkynyls, divalent substituted alkynyls, divalent heteroalkynyls, divalent alkoxys, divalent lower alkoxys, divalent aryloxys, divalent alkylthios, divalent lower alkyl thios, divalent arylthios, divalent aryls, divalent substituted aryls, divalent heteroaryls, divalent aralkyls, divalent aralkylenes, divalent alkaryls, divalent alkarylenes, divalent haloalkyls, divalent haloalkenyls, divalent haloalkynyls, divalent heteroalkyls, divalent heterocycles, divalent heteroaryls, divalent heteroatom-containing groups, divalent hydrocarbyls, divalent lower hydrocarbyls, divalent substituted hydrocarbyls, divalent heterohydrocarbyls, divalent silyls, divalent boryls, divalent phosphinos, divalent phosphines, divalent aminos, divalent amines, divalent ethers, divalent thioethers. Additional non-limiting examples of bridging group A include divalent hydrocarbon groups containing at least one Group 13 to 16 atom, such as but not limited to at least one of a carbon, oxygen, nitrogen, silicon, aluminum, boron, germanium and tin atom and combinations thereof; wherein the heteroatom may also be $C_1$ to $C_{12}$ alkyl or aryl substituted to satisfy neutral valency. The bridging group (A) may also contain substituent groups R as defined above for formula (I) including halogen radicals and iron. More particular non-limiting examples of bridging group (A) are represented by $C_1$ to $C_6$ alkylenes, substituted $C_1$ to $C_6$ alkylenes, oxygen, sulfur, $R'_2C=$, $R'_2Si=$, $—Si(R')_2Si(R'_2)—$, $R'_2Ge=$, $R'P=$ (wherein "=" represents two chemical bonds), where R' is independently selected from the group consisting of hydride, hydrocarbyl, substituted hydrocarbyl, halocarbyl, substituted halocarbyl, hydrocarbyl-substituted organometalloid, halocarbyl-substituted organometalloid, disubstituted boron, disubstituted Group 15 atoms, substituted Group 16 atoms, and halogen radical; and wherein two or more R' may be joined to form a ring or ring system. In one embodiment, the bridged metallocene catalyst component of formula (II) has two or more bridging groups (A).

Other non-limiting examples of bridging group (A) include methylene, ethylene, ethylidene, propylidene, isopropylidene, diphenylmethylene, 1,2-dimethylethylene, 1,2-diphenylethylene, 1,1,2,2-tetramethylethylene, dimethylsilyl, diethylsilyl, methyl-ethylsilyl, trifluoromethylbutylsilyl, bis(trifluoromethyl)silyl, di(n-butyl)silyl, di(n-propyl)silyl, di(1-propyl)silyl, di(n-hexyl)silyl, dicyclohexylsilyl, diphenylsilyl, cyclohexylphenylsilyl, t-butylcyclohexylsilyl, di(t-butylphenyl)silyl, di(p-tolyl)silyl and the corresponding moieties wherein the Si atom is replaced by a Ge or a C atom; dimethylsilyl, diethylsilyl, dimethylgermyl and diethylgermyl.

In another embodiment, bridging group (A) may also be cyclic, comprising, for example 4 to 10, 5 to 7 ring members in a more particular embodiment. The ring members may be selected from the elements mentioned above, from one or more of B, C, Si, Ge, N and O in a particular embodiment. Non-limiting examples of ring structures which may be present as or part of the bridging moiety are cyclobutylidene, cyclopentylidene, cyclohexylidene, cycloheptylidene, cyclooctylidene and the corresponding rings where one or two carbon atoms are replaced by at least one of Si, Ge, N and O, in particular, Si and Ge. The bonding arrangement between the ring and the Cp groups may be either cis-, trans-, or a combination.

The cyclic bridging groups (A) may be saturated or unsaturated and/or carry one or more substituents and/or be fused to one or more other ring structures. If present, the one or more substituents are selected from the group consisting of hydrocarbyl (e.g., alkyl such as methyl) and halogen (e.g., F, Cl) in one embodiment. The one or more Cp groups which the above cyclic bridging moieties may optionally be fused to may be saturated or unsaturated and are selected from the group consisting of those having 4 to 10, more particularly 5, 6 or 7 ring members (selected from the group consisting of C, N, O and S in a particular embodiment) such as, for example, cyclopentyl, cyclohexyl and phenyl. Moreover, these ring structures may themselves be fused such as, for example, in the case of a naphthyl group. Moreover, these (optionally fused) ring structures may carry one or more substituents. Illustrative, non-limiting examples of these substituents are hydrocarbyl (particularly alkyl) groups and halogen atoms.

The ligands $Cp^A$ and $Cp^B$ of formula (I) and (II) are different from each other in one embodiment, and the same in another embodiment.

In yet another aspect, the metallocene catalyst components include mono-ligand metallocene compounds (e.g., mono cyclopentadienyl catalyst components) such as described in WO 93/08221 for example. In this embodiment, the at least one metallocene catalyst component is a bridged "half-sandwich" metallocene represented by the formula (III):

$$Cp^A(A)QMX_n \qquad (III)$$

wherein $Cp^A$ is defined above and is bound to M; (A) is defined above and is a bridging group bonded to Q and $Cp^A$; and wherein an atom from the Q group is bonded to M; and n is 0 or an integer from 1 to 3; 1 or 2 in a particular embodiment. In formula (III), $Cp^A$, (A) and Q may form a fused ring system. The X groups and n of formula (III) are as defined above in formula (I) and (II). In one embodiment, $Cp^A$ is selected from the group consisting of cyclopentadienyl, indenyl, tetrahydroindenyl, fluorenyl, substituted versions thereof, and combinations thereof.

In formula (III), Q is a heteroatom-containing ligand in which the bonding atom (the atom that is bonded with the metal M) is selected from the group consisting of Group 15 atoms and Group 16 atoms in one embodiment, and selected from the group consisting of nitrogen, phosphorus, oxygen or sulfur atom in a more particular embodiment, and nitrogen and oxygen in yet a more particular embodiment. Non-limiting examples of Q groups include ethers, amines, phosphines, thioethers, alkylamines, arylamines, mercapto compounds, ethoxy compounds, carboxylates (e.g., pivalate), carbamates, azenyl, azulene, pentalene, phosphoyl, phosphinimine, pyrrolyl, pyrozolyl, carbazolyl, borabenzene other compounds comprising Group 15 and Group 16 atoms capable of bonding with M.

In yet another aspect, the at least one metallocene catalyst component is an unbridged "half sandwich" metallocene represented by the formula (IV):

$$Cp^4 MQ_q X_n \qquad (IV)$$

wherein $Cp^4$ is defined as for the Cp groups in (I) and is a ligand that is bonded to M; each Q is independently bonded to M; Q is also bound to $Cp^4$ in one embodiment; X is a leaving group as described above in (I); n ranges from 0 to 3, and is 1 or 2 in one embodiment; q ranges from 0 to 3, and is 1 or 2 in one embodiment. In one embodiment, $Cp^4$ is selected from the group consisting of cyclopentadienyl, indenyl, tetrahydroindenyl, fluorenyl, substituted version thereof, and combinations thereof.

In formula (IV), Q is selected from the group consisting of $ROO^-$, $RO$—, $R(O)$—, —$NR$—, —$CR_2$—, —$S$—, —$NR_2$, —$CR_3$, —$SR$, —$SiR_3$, —$PR_2$, —H, and substituted and unsubstituted aryl groups, wherein R is selected from the group consisting of hydrocarbyls, lower hydrocarbyls, substituted hydrocarbyls, heterohydrocarbyls, alkyls, lower alkyls, substituted alkyls, heteroalkyls, alkenyls, lower alkenyls, substituted alkenyls, heteroalkenyls, alkynyls, lower alkynyls, substituted alkynyls, heteroalkynyls, alkoxys, lower alkoxys, aryloxys, hydroxyls, alkylthios, lower alkyls thios, arylthios, thioxys, aryls, substituted aryls, heteroaryls, aralkyls, aralkylenes, alkaryls, alkarylenes, halides, haloalkyls, haloalkenyls, haloalkynyls, heteroalkyls, heterocycles, heteroaryls, heteroatom-containing groups, silyls, boryls, phosphinos, phosphines, aminos, amines, cycloalkyls, acyls, aroyls, alkylthiols, dialkylamines, alkylamidos, alkoxycarbonyls, aryloxycarbonyls, carbomoyls, alkyl- and dialkyl-carbamoyls, acyloxys, acylaminos, aroylaminos, and combinations thereof. In another embodiment, R is selected from $C_1$ to $C_6$ alkyls, $C_6$ to $C_{12}$ aryls, $C_1$ to $C_6$ alkylamines, $C_6$ to $C_{12}$ alkylarylamines, $C_1$ to $C_6$ alkoxys, $C_6$ to $C_{12}$ aryloxys, and the like. Non-limiting examples of Q include $C_1$ to $C_{12}$ carbamates, $C_1$ to $C_{12}$ carboxylates (e.g., pivalate), $C_2$ to $C_{20}$ alkyls, and $C_2$ to $C_{20}$ heteroallyl moieties.

Described another way, the "half sandwich" metallocenes above can be described as in formula (II), such as described in, for example, U.S. Pat. No. 6,069,213:

$$Cp^4 M(Q_2 GZ) X_n \text{ or } T(Cp^4 M(Q_2 GZ) X_n)_m \qquad (V)$$

wherein M, $Cp^4$, X and n are as defined above;

$Q_2 GZ$ forms a polydentate ligand unit (e.g., pivalate), wherein at least one of the Q groups form a bond with M, and is defined such that each Q is independently selected from the group consisting of —O—, —NR—, —$CR_2$— and —S—; G is either carbon or silicon; and Z is selected from the group consisting of R, —OR, —$NR_2$, —$CR_3$, —SR, —$SiR_3$, —$PR_2$, and hydride, providing that when Q is —NR—, then Z is selected from the group consisting of —OR, —$NR_2$, —SR, —$SiR_3$, —$PR_2$; and provided that neutral valency for Q is satisfied by Z; and wherein each R is independently selected from the group consisting of hydrocarbyls, lower hydrocarbyls, substituted hydrocarbyls, heterohydrocarbyls, alkyls, lower alkyls, substituted alkyls, heteroalkyls, alkenyls, lower alkenyls, substituted alkenyls, heteroalkenyls, alkynyls, lower alkynyls, substituted alkynyls, heteroalkynyls, alkoxys, lower alkoxys, aryloxys, hydroxyls, alkylthios, lower alkyls thios, arylthios, thioxys, aryls, substituted aryls, heteroaryls, aralkyls, aralkylenes, alkaryls, alkarylenes, halides, haloalkyls, haloalkenyls, haloalkynyls, heteroalkyls, heterocycles, heteroaryls, heteroatom-containing groups, silyls, boryls, phosphinos, phosphines, aminos, amines, cycloalkyls, acyls, aroyls, alkylthiols, dialkylamines, alkylamidos, alkoxycarbonyls, aryloxycarbonyls, carbomoyls, alkyl- and dialkyl-carbamoyls, acyloxys, acylaminos, aroylaminos, and combinations thereof. In another embodiment, R is selected from the group consisting of $C_1$ to $C_{10}$ heteroatom containing groups, $C_1$ to $C_{10}$ alkyls, $C_6$ to $C_{12}$ aryls, $C_6$ to $C_{12}$ alkylaryls, $C_1$ to $C_{10}$ alkoxys, and $C_6$ to $C_{12}$ aryloxys;

n is 1 or 2 in a particular embodiment; and

T is a bridging group selected from the group consisting of $C_1$ to $C_{10}$ alkylenes, $C_6$ to $C_{12}$ arylenes and $C_1$ to $C_{10}$ heteroatom containing groups, and $C_6$ to $C_{12}$ heterocyclic groups; wherein each T group bridges adjacent "$Cp^4 M(Q_2 GZ) X_n$" groups, and is chemically bonded to the $Cp^4$ groups.

m is an integer from 1 to 7; m is an integer from 2 to 6 in a more particular embodiment.

In another aspect, the at least one metallocene catalyst component can be described more particularly in structures (VIa), (VIb), (VIc), (VId), (VIe), and (VIf):

(VIa-i)

(VIa-ii)

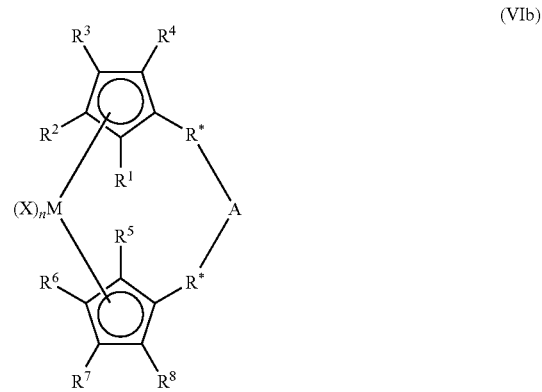

(VIb)

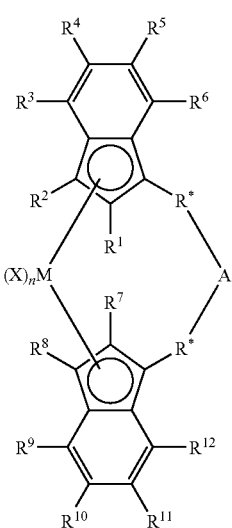
(VIc)

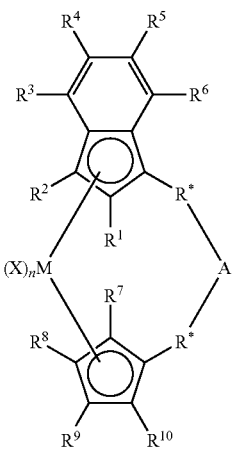
(VId)

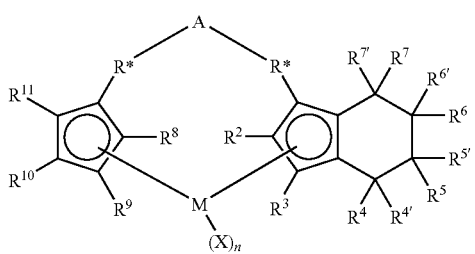
(VIe)

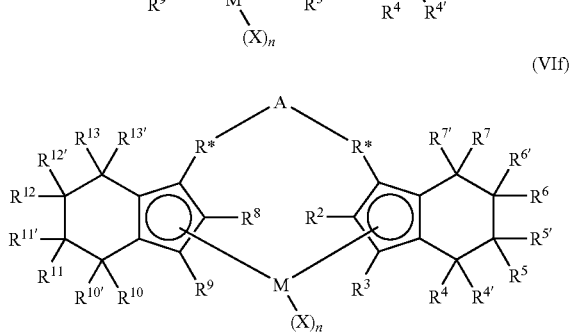
(VIf)

wherein in structures (VIa) to (VIf), M is selected from the group consisting of Group 3 to Group 12 atoms, and selected from the group consisting of Group 3 to Group 10 atoms in a more particular embodiment, and selected from the group consisting of Group 3 to Group 6 atoms in yet a more particular embodiment, and selected from the group consisting of Group 4 atoms in yet a more particular embodiment, and selected from the group consisting of Zr and Hf in yet a more particular embodiment; and is Zr in yet a more particular embodiment;

wherein Q in (VIa) to (VIf) is selected from the group consisting of hydrocarbyls, lower hydrocarbyls, substituted hydrocarbyls, heterohydrocarbyls, alkyls, lower alkyls, substituted alkyls, heteroalkyls, alkenyls, lower alkenyls, substituted alkenyls, heteroalkenyls, alkynyls, lower alkynyls, substituted alkynyls, heteroalkynyls, alkoxys, lower alkoxys, aryloxys, hydroxyls, alkylthios, lower alkyls thios, arylthios, thioxys, aryls, substituted aryls, heteroaryls, aralkyls, aralkylenes, alkaryls, alkarylenes, halides, haloalkyls, haloalkenyls, haloalkynyls, heteroalkyls, heterocycles, heteroaryls, heteroatom-containing groups, silyls, boryls, phosphinos, phosphines, aminos, amines, cycloalkyls, acyls, aroyls, alkylthiols, dialkylamines, alkylamidos, alkoxycarbonyls, aryloxycarbonyls, carbomoyls, alkyl- and dialkyl-carbamoyls, acyloxys, acylaminos, aroylaminos, alkylenes, aryls, arylenes, alkoxys, aryloxys, amines, arylamines (e.g., pyridyl) alkylamines, phosphines, alkylphosphines, substituted alkyls, substituted aryls, substituted alkoxys, substituted aryloxys, substituted amines, substituted alkylamines, substituted phosphines, substituted alkylphosphines, carbamates, heteroallyls, carboxylates (non-limiting examples of suitable carbamates and carboxylates include trimethylacetate, trimethylacetate, methylacetate, p-toluate, benzoate, diethylcarbamate, and dimethylcarbamate), fluorinated alkyls, fluorinated aryls, and fluorinated alkylcarboxylates; wherein the saturated groups defining Q comprise from 1 to 20 carbon atoms in one embodiment; and wherein the aromatic groups comprise from 5 to 20 carbon atoms in one embodiment; wherein R* may be selected from divalent alkyls, divalent lower alkyls, divalent substituted alkyls, divalent heteroalkyls, divalent alkenyls, divalent lower alkenyls, divalent substituted alkenyls, divalent heteroalkenyls, divalent alkynyls, divalent lower alkynyls, divalent substituted alkynyls, divalent heteroalkynyls, divalent alkoxys, divalent lower alkoxys, divalent aryloxys, divalent alkylthios, divalent lower alkyl thios, divalent arylthios, divalent aryls, divalent substituted aryls, divalent heteroaryls, divalent aralkyls, divalent aralkylenes, divalent alkaryls, divalent alkarylenes, divalent haloalkyls, divalent haloalkenyls, divalent haloalkynyls, divalent heteroalkyls, divalent heterocycles, divalent heteroaryls, divalent heteroatom-containing groups, divalent hydrocarbyls, divalent lower hydrocarbyls, divalent substituted hydrocarbyls, divalent heterohydrocarbyls, divalent silyls, divalent boryls, divalent phosphinos, divalent phosphines, divalent aminos, divalent amines, divalent ethers, divalent thioethers. Additionally, R* may be from the group of divalent hydrocarbylenes and heteroatom-containing hydrocarbylenes in one embodiment; and selected from the group consisting of alkylenes, substituted alkylenes and heteroatom-containing hydrocarbylenes in another embodiment; and selected from the group consisting of $C_1$ to $C_{12}$ alkylenes, $C_1$ to $C_{12}$ substituted alkylenes, and $C_1$ to $C_{12}$ heteroatom-containing hydrocarbylenes in a more particular embodiment; and selected from the group consisting of $C_1$ to $C_4$ alkylenes in yet a more particular embodiment; and wherein both R* groups are identical in another embodiment in structures (VIf);

A is as described above for (A) in structure (II), and more particularly, selected from the group consisting of a chemical bond, —O—, —S—, —SO$_2$—, —NR—, =SiR$_2$, =GeR$_2$, =SnR$_2$, —R$_2$SiSiR$_2$—, RP=, $C_1$ to $C_{12}$ alkylenes, substituted $C_1$ to $C_{12}$ alkylenes, divalent $C_4$ to $C_{12}$ cyclic hydrocarbons and substituted and unsubstituted aryl groups in one embodiment; and selected from the group consisting of $C_5$ to $C_8$ cyclic hydrocarbons, —$CH_2CH_2$—, =$CR_2$ and =$SiR_2$ in a more particular embodiment; wherein and R is selected from the group consisting of alkyls, cycloalkyls, aryls, alkoxys, fluoroalkyls and heteroatom-containing hydrocarbons in one embodiment; and R is selected from the group consisting of $C_1$ to $C_6$ alkyls, substituted phenyls, phenyl, and $C_1$ to $C_6$ alkoxys in a more particular embodiment; and R is selected from the group consisting of methoxy, methyl, phenoxy, and phenyl in yet a more particular embodiment; wherein A may be absent in yet another embodiment, in which case each R* is defined as for $R^1$-$R^{13}$; each X is as described above in (I); n is an integer from 0 to 4, and from 1 to 3 in another embodiment, and 1 or 2 in yet another embodiment; and $R^1$ through $R^{13}$ are independently: selected from the group consisting of hydrogen radicals, hydrocarbyls, lower hydrocarbyls, substituted hydrocarbyls, heterohydrocarbyls, alkyls, lower alkyls, substituted alkyls, heteroalkyls, alkenyls, lower alkenyls, substituted alkenyls, heteroalkenyls, alkynyls, lower alkynyls, substituted alkynyls, heteroalkynyls, alkoxys, lower alkoxys, aryloxys, hydroxyls, alkylthios, lower alkyls thios, arylthios, thioxys, aryls, substituted aryls, heteroaryls, aralkyls, aralkylenes, alkaryls, alkarylenes, halides, haloalkyls, haloalkenyls, haloalkynyls, heteroalkyls, heterocycles, heteroaryls, heteroatom-containing groups, silyls, boryls, phosphinos, phosphines, aminos, amines, cycloalkyls, acyls, aroyls, alkylthiols, dialkylamines, alkylamidos, alkoxycarbonyls, aryloxycarbonyls, carbomoyls, alkyl- and dialkyl-carbamoyls, acyloxys, acylaminos, aroylaminos through $R^{13}$ may also be selected independently from $C_1$ to $C_{12}$ alkyls, $C_2$ to $C_{12}$ alkenyls, $C_6$ to $C_{12}$ aryls, $C_7$ to $C_{20}$ alkylaryls, $C_1$ to $C_{12}$ alkoxys, $C_1$ to $C_{12}$ fluoroalkyls, $C_6$ to $C_{12}$ fluoroaryls, and $C_1$ to $C_{12}$ heteroatom-containing hydrocarbons and substituted derivatives thereof in one embodiment; selected from the group consisting of hydrogen radical, fluorine radical, chlorine radical, bromine radical, $C_1$ to $C_6$ alkyls, $C_2$ to $C_6$ alkenyls, $C_7$ to $C_{18}$ alkylaryls, $C_1$ to $C_6$ fluoroalkyls, $C_2$ to $C_6$ fluoroalkenyls, $C_7$ to $C_{18}$ fluoroalkylaryls in a more particular embodiment; and hydrogen radical, fluorine radical, chlorine radical, methyl, ethyl, propyl, isopropyl, butyl, isobutyl, tertiary butyl, hexyl, phenyl, 2,6-dimethylpheyl, and 4-tertiarybutylpheyl groups in yet a more particular embodiment; wherein adjacent R groups may form a ring, either saturated, partially saturated, or completely saturated.

The structure of the metallocene catalyst component represented by (XIa) may take on many forms such as disclosed in, for example, U.S. Pat. No. 5,026,798, U.S. Pat. No. 5,703,187, and U.S. Pat. No. 5,747,406, including a dimmer or oligomeric structure, such as disclosed in, for example, U.S. Pat. No. 5,026,798 and U.S. Pat. No. 6,069,213.

In a particular embodiment of the metallocene represented in (VId), $R^1$ and $R^2$ form a conjugated 6-membered carbon ring system that may or may not be substituted.

In one non-limiting embodiment, the metallocene compound is selected from the group consisting of (Pentamethylcyclopentadienyl)(Propylcyclopentadienyl)ZrX'$_2$, (Tetramethylcyclopentadienyl)(Propylcyclopentadienyl)ZrX'$_2$, (Pentamethylcyclopentadienyl)(Butyl cyclopentadienyl)ZrX'$_2$, (Tetramethylcyclopentadienyl)(Butyl cyclopentadienyl)ZrX'$_2$, Me2Si(Indenyl)2ZrX2, Me2Si(Tetrahydroindenyl)2ZrX'$_2$, (n-propyl cyclopentadienyl)2ZrX'$_2$, (n-propyl cyclopentadienyl)2HfX'$_2$, (n-butyl cyclopentadienyl)2ZrX'$_2$, (n-butyl cyclopentadienyl)2HfX'$_2$, (1-Methyl, 3-Butyl cyclopentadienyl)2ZrX'$_2$, HN(CH2CH2N(2,4,6-Me3-Phenyl))2ZrX'$_2$, HN(CH2CH2N(2,3,4,5,6-Me5-Phenyl))2ZrX'$_2$, (1-Me, 3-Bu-Cp)2ZrCl2, (CpPr)(Me4 Cp)HfCl2, (CpBu)2ZrCl2, (CpPr)2ZrCl2, (CpBu)2HfCl2, (CpPr)2HfCl2, and any combinations thereof.

By "derivatives thereof", it is meant any substitution or ring formation as described above; and in particular, replacement of the metal "M" (Cr, Zr, Ti or Hf) with an atom selected from the group consisting of Cr, Zr, Hf and Ti; and replacement of the "X" group with any of $C_1$ to $C_5$ alkyls, $C_6$ aryls, $C_6$ to $C_{10}$ alkylaryls, fluorine or chlorine; n is 1, 2 or 3.

It is contemplated that the metallocene catalysts components described above include their structural or optical or enantiomeric isomers (racemic mixture), and may be a pure enantiomer in one embodiment.

As used herein, a single, bridged, asymmetrically substituted metallocene catalyst component having a racemic and/or meso isomer does not, itself, constitute at least two different bridged, metallocene catalyst components.

The "metallocene catalyst component" may comprise any combination of any "embodiment" described herein.

Metallocene compounds and catalysts are known in the art and any one or more may be utilized herein. Suitable metallocenes include but are not limited to all of the metallocenes disclosed and referenced in the U.S. patents cited above, as well as those disclosed and referenced in U.S. Pat. Nos. 7,179,876, 7,169,864, 7,157,531, 7,129,302, 6,995,109, 6,958,306, 6,884748, 6,689,847, U.S. Patent Application publication number 2007/0055028, and published PCT Application Nos. WO 97/22635, WO 00/699/22, WO 01/30860, WO 01/30861, WO 02/46246, WO 02/50088, WO 04/026921, and WO 06/019494, all fully incorporated herein by reference. Additional catalysts suitable for use herein include those referenced in U.S. Pat. Nos. 6,309,997, 6,265,338, U.S. Patent Application publication number 2006/019925, and the following articles: Chem Rev 2000, 100, 1253, Resconi; Chem Rev 2003, 103, 283; Chem. Eur. J. 2006, 12, 7546 Mitsui; J Mol Catal A 2004, 213, 141; Macromol Chem Phys, 2005, 206, 1847; and J Am Chem Soc 2001, 123, 6847.

Group 15-Containing Catalysts

"Group 15-containing catalyst components", as referred to herein, include Group 3 to Group 12 metal complexes, wherein the metal is 2 to 4 coordinate, the coordinating moiety or moieties including at least two Group 15 atoms, and up to four Group 15 atoms. In one embodiment, the Group 15-containing catalyst component is a complex of a Group 4 metal and from one to four ligands such that the Group 4 metal is at least 2 coordinate, the coordinating moiety or moieties including at least two nitrogens. Representative Group 15-containing compounds are disclosed in, for example, WO 98/46651, WO 99/01460; EP A1 0 893,454; EP A1 0 894 005; U.S. Pat. No. 5,318,935; U.S. Pat. No. 5,889, 128 U.S. Pat. No. 6,333,389 B2 and U.S. Pat. No. 6,271,325 B1.

The Group 15-containing catalyst components are prepared by methods known in the art, such as those disclosed in, for example, EP 0 893 454 A1, U.S. Pat. No. 5,889,128, U.S. Pat. No. 6,333,389 B2 and WO 00/37511.

The "Group 15-containing catalyst component" may comprise any combination of any "embodiment" described herein.

Phenoxide Transition Metal Catalysts

Phenoxide transition metal catalyst compositions are heteroatom substituted phenoxide ligated Group 3 to 10 transition metal or lanthanide metal compounds wherein the metal is bound to the oxygen of the phenoxide group. Phenoxide transition metal catalyst compounds may be represented by Formula XIV or XV:

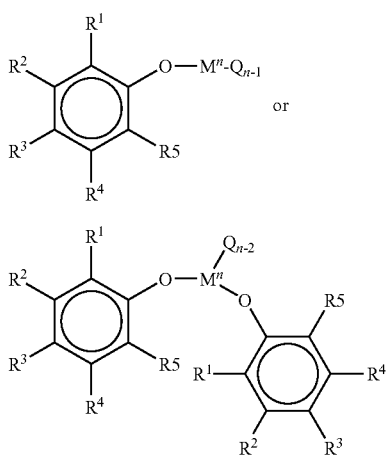

wherein $R^1$ is hydrogen or a $C_4$ to $C_{100}$ group, preferably a tertiary alkyl group, preferably a $C_4$ to $C_{20}$ alkyl group, preferably a $C_4$ to $C_{20}$ tertiary alkyl group, preferably a neutral $C_4$ to $C_{100}$ group and may or may not also be bound to M;

at least one of $R^2$ to $R^5$ is a heteroatom containing group, the rest of $R^2$ to $R^5$ are independently hydrogen or a $C_1$ to $C_{100}$ group, preferably a $C_4$ to $C_{20}$ alkyl group, preferred examples of which include butyl, isobutyl, t-butyl, pentyl, hexyl, heptyl, isohexyl, octyl, isooctyl, decyl, nonyl, dodecyl, and any of $R^2$ to $R^5$ also may or may not be bound to M;

Each $R^1$ to $R^5$ group may be independently substituted or unsubstituted with other atoms, including heteroatoms or heteroatom containing group(s);

O is oxygen;

M is a Group 3 to Group 10 transition metal or lanthanide metal, preferably a Group 4 metal, preferably M is Ti, Zr or Hf;

n is the valence state of the metal M, preferably 2, 3, 4, or 5; and

Q is, and each Q may be independently be, an alkyl, halogen, benzyl, amide, carboxylate, carbamate, thiolate, hydride or alkoxide group, or a bond to an R group containing a heteroatom which may be any of $R^1$ to $R^5$.

A heteroatom containing group may be any heteroatom or a heteroatom bound to carbon, silicon or another heteroatom. Preferred heteroatoms include boron, aluminum, silicon, nitrogen, phosphorus, arsenic, tin, lead, antimony, oxygen, selenium, and tellurium. Particularly preferred heteroatoms include nitrogen, oxygen, phosphorus, and sulfur. Even more particularly preferred heteroatoms include nitrogen and oxygen. The heteroatom itself may be directly bound to the phenoxide ring or it may be bound to another atom or atoms that are bound to the phenoxide ring. The heteroatom containing group may contain one or more of the same or different heteroatoms. Preferred heteroatom containing groups include imines, amines, oxides, phosphines, ethers, ketones, oxoazolines heterocyclics, oxazolines, thioethers, and the like.

Particularly preferred heteroatom containing groups include imines. Any two adjacent R groups may form a ring structure, preferably a 5 or 6 membered ring. Likewise the R groups may form multi-ring structures. In one embodiment any two or more R groups do not form a 5 membered ring.

In a preferred embodiment the heteroatom substituted phenoxide transition metal compound is an iminophenoxide Group 4 transition metal compound, and more preferably an iminophenoxidezirconium compound.

It is further contemplated by the invention that other catalysts can be combined with the compounds of the invention. For example, see Hlalky, G. G. *Chem. Rev.* (2000), 100, 1347; Alt, H.; Koppl, A. *Chem. Rev.* (2000), 100, 1205; Resconi, L. et al., *Chem. Rev.* (2000), 100, 1253; Bryntzinger, H. H. et. al., *Angew. Chem. Int. Ed. Engl.* (1995), 34, 1143; Ittel, S. D. et al., *Chem. Rev.* (2000), 100, 1169; Gibson, V. C. et al., *Chem. Rev.* (2003), 103, 283; Skupinska, J., *Chem. Rev.* (1991), 91, 613; Carter, A. et al., *Chem. Commun.*, 2002, 858; McGuinness, D. S.; et al., *J. Am. Chem. Soc.* (2003), 125, 5272; McGuiness, D. S., *Chem. Commun* (2003), 334; U.S. Pat. Nos. 4,937,299, 4,935,474, 5,281,679, 5,359,015, 5,470,811, and 5,719,241, all of which are herein fully incorporated herein reference.

In another embodiment of the invention one or more catalyst compounds or catalyst systems may be used in combination with one or more conventional-type catalyst compounds or catalyst systems. Non-limiting examples of mixed catalysts and catalyst systems are described in U.S. Pat. Nos. 4,159,965, 4,325,837, 4,701,432, 5,124,418, 5,077,255, 5,183,867, 5,391,660, 5,395,810, 5,691,264, 5,723,399 and 5,767,031, and PCT Publication No. WO 96/23010 published Aug. 1, 1996, all of which are herein fully incorporated by reference.

High Molecular Weight Catalysts

With respect to the catalyst systems of the disclosure wherein the high molecular weight catalyst compound is a non-metallocene compound generally the compound is a biphenyl phenol catalyst (BPP) compound. BPP catalyst compounds are known in the art and any are suitable for use herein such as, but not limited to those disclosed in U.S. Pat. Nos. 7,091,282, 7,030,256, 7,060,848, 7,126,031, 6,841,502, U.S. Patent Application publication numbers 2006/0025548, 2006/020588, 2006/00211892, and published PCT application numbers WO 2006/020624, WO 2005/108406, and WO 2003/091262, all incorporated herein by reference.

Preference may be given to BPP compounds having formula (XVI) shown below:

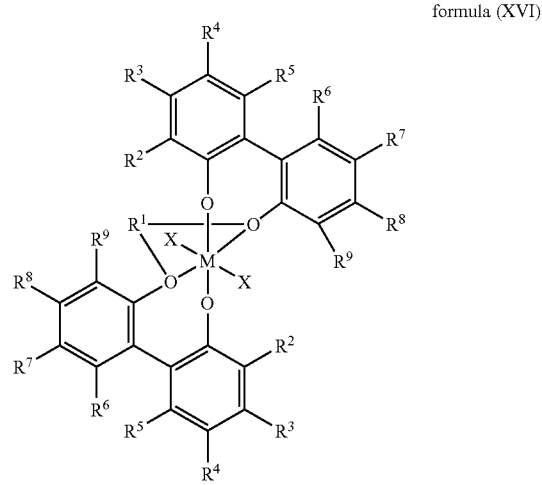

formula (XVI)

wherein M may be Ti, Zr, or Hf. In one embodiment $R^1$ of formula I is hydride, hydrocarbyl, lower hydrocarbyl, substituted hydrocarbyl, heterohydrocarbyl, alkyl, lower alkyl, substituted alkyl, heteroalkyl, alkenyl, lower alkenyl, substituted alkenyl, heteroalkenyl, alkynyl, lower alkynyl, substituted alkynyl, heteroalkynyl, alkoxy, lower alkoxy, aryloxy, hydroxyl, alkylthio, lower alkyl thio, arylthio, thioxy, aryl, substituted aryl, heteroaryl, aralkyl, aralkylene, alkaryl, alkarylene, halide, haloalkyl, haloalkenyl, haloalkynyl, heteroalkyl, heterocycle, heteroaryl, heteroatom-containing group, silyl, boryl, phosphino, phosphine, amino, amine In some embodiments, the bridging group $R^1$ is selected from the group consisting of optionally substituted divalent hydrocarbyl and divalent heteroatom containing hydrocarbyl. In other embodiments, $R^1$ is selected from the group consisting of optionally substituted divalent alkyl, divalent lower alkyl, divalent substituted alkyl, divalent heteroalkyl, divalent alkenyl, divalent lower alkenyl, divalent substituted alkenyl, divalent heteroalkenyl, divalent alkynyl, divalent lower alkynyl, divalent substituted alkynyl, divalent heteroalkynyl, divalent alkoxy, divalent lower alkoxy, divalent aryloxy, divalent alkylthio, divalent lower alkyl thio, divalent arylthio, divalent aryl, divalent substituted aryl, divalent heteroaryl, divalent aralkyl, divalent aralkylene, divalent alkaryl, divalent alkarylene, divalent halide, divalent haloalkyl, divalent haloalkenyl, divalent haloalkynyl, divalent heteroalkyl, divalent heterocycle, divalent heteroaryl, divalent heteroatom-containing group, divalent hydrocarbyl, divalent lower hydrocarbyl, divalent substituted hydrocarbyl, divalent heterohydrocarbyl, divalent silyl, divalent boryl, divalent phosphino, divalent phosphine, divalent amino, divalent amine, divalent ether, divalent thioether. In still other embodiments, $R^1$ can be represented by the general formula $-(Q''R^{40}_{2-z''})_{z'}-$ wherein each Q" is either carbon or silicon and each $R^{40}$ may be the same or different from the others such that each $R^{40}$ is selected from the group consisting of hydride and optionally substituted hydrocarbyl, and optionally two or more $R^{40}$ groups may be joined into a ring structure having from 3 to 50 atoms in the ring structure (not counting hydrogen atoms); and z' is an integer from 1 to 10, more specifically from 15 and even more specifically from 25 and z" is 0, 1 or 2. For example, when z" is 2, there is no $R^{40}$ groups associated with Q", which allows for those cases where one Q" is multiply bonded to a second Q". In more specific embodiments, $R^{40}$ is selected from the group consisting of hydride, halide, and optionally substituted alkyl, alkenyl, alkynyl, heteroalkyl, heteroalkenyl, heteroalkynyl, aryl, heteroaryl, alkoxyl, aryloxyl, silyl, boryl, phosphino, amino, thioxy, alkylthio, arylthio, and combinations thereof. Specific $R^1$ groups within these embodiments include $—(CH_2)_2—$, $—(CH_2)_4—$ and $—(CH_2)—(C_6H_4)—(CH_2)—$. Other specific bridging moieties are set forth in the example ligands and complexes herein.

In one embodiment $R^2$-$R^9$ of formula (XVI) are optionally hydrocarbyl, lower hydrocarbyl, substituted hydrocarbyl, heterohydrocarbyl, alkyl, lower alkyl, substituted alkyl, heteroalkyl, alkenyl, lower alkenyl, substituted alkenyl, heteroalkenyl, alkynyl, lower alkynyl, substituted alkynyl, heteroalkynyl, alkoxy, lower alkoxy, aryloxy, hydroxyl, alkylthio, lower alkyl thio, arylthio, thioxy, aryl, substituted aryl, heteroaryl, aralkyl, aralkylene, alkaryl, alkarylene, halide, haloalkyl, haloalkenyl, haloalkynyl, heteroalkyl, heterocycle, heteroaryl, heteroatom-containing group, silyl, boryl, phosphino, phosphine, amino, or amine Each X in formula (XVI) is independently selected from the group consisting of: any leaving group in one embodiment; halogen ions, hydrides, $C_1$ to $C_{12}$ alkyls, $C_2$ to $C_{12}$ alkenyls, $C_6$ to $C_{12}$ aryls, $C_7$ to $C_{20}$ alkylaryls, $C_1$ to $C_{12}$ alkoxys, $C_6$ to $C_{16}$ aryloxys, $C_7$ to $C_{18}$ alkylaryloxys, $C_1$ to $C_{12}$ fluoroalkyls, $C_6$ to $C_{12}$ fluoroaryls, and $C_1$ to $C_{12}$ heteroatom-containing hydrocarbons and substituted derivatives thereof in a more particular embodiment; hydride, halogen ions, $C_1$ to $C_6$ alkyls, $C_2$ to $C_6$ alkenyls, $C_7$ to $C_{18}$ alkylaryls, $C_1$ to $C_6$ alkoxys, $C_6$ to $C_{14}$ aryloxys, $C_7$ to $C_{16}$ alkylaryloxys, $C_1$ to $C_6$ alkylcarboxylates, $C_1$ to $C_6$ fluorinated alkylcarboxylates, $C_6$ to $C_{12}$ arylcarboxylates, $C_7$ to $C_{18}$ alkylarylcarboxylates, $C_1$ to $C_6$ fluoroalkyls, $C_2$ to $C_6$ fluoroalkenyls, and $C_7$ to $C_{18}$ fluoroalkylaryls in yet a more particular embodiment; hydride, chloride, fluoride, methyl, phenyl, phenoxy, benzoxy, tosyl, fluoromethyls and fluorophenyls in yet a more particular embodiment; $C_1$ to $C_{12}$ alkyls, $C_2$ to $C_{12}$ alkenyls, $C_6$ to $C_{12}$ aryls, $C_7$ to $C_{20}$ alkylaryls, substituted $C_1$ to $C_{12}$ alkyls, substituted $C_6$ to $C_{12}$ aryls, substituted $C_7$ to $C_{20}$ alkylaryls and $C_1$ to $C_{12}$ heteroatom-containing alkyls, $C_1$ to $C_{12}$ heteroatom-containing aryls and $C_1$ to $C_{12}$ heteroatom-containing alkylaryls in yet a more particular embodiment; chloride, fluoride, $C_1$ to $C_6$ alkyls, $C_2$ to $C_6$ alkenyls, $C_7$ to $C_{18}$ alkylaryls, halogenated $C_1$ to $C_6$ alkyls, halogenated $C_2$ to $C_6$ alkenyls, and halogenated $C_7$ to $C_{18}$ alkylaryls in yet a more particular embodiment; fluoride, methyl, ethyl, propyl, phenyl, methylphenyl, dimethylphenyl, trimethylphenyl, fluoromethyls (mono-, di- and trifluoromethyls) and fluorophenyls (mono-, di-, tri-, tetra- and pentafluorophenyls) in yet a more particular embodiment.

Other non-limiting examples of X groups in formula (XVI) include amines, phosphines, ethers, carboxylates, dienes, hydrocarbon radicals having from 1 to 20 carbon atoms, fluorinated hydrocarbon radicals (e.g., $—C_6F_5$ (pentafluorophenyl)), fluorinated alkylcarboxylates (e.g., $CF_3C(O)O^-$), hydrides and halogen ions and combinations thereof. Other examples of X ligands include alkyl groups such as cyclobutyl, cyclohexyl, methyl, heptyl, tolyl, trifluoromethyl, tetramethylene, pentamethylene, methylidene, methyoxy, ethyoxy, propoxy, phenoxy, bis(N-methylanilide), dimethylamide, dimethylphosphide radicals and the like. In one embodiment, two or more X's form a part of a fused ring or ring system.

In one embodiment of the compound represented by formula (XVI), M may be Ti, Zr, or Hf. $R^1$, $R^3$, $R^5$ through $R^9$ are H; each $R^2$ may be any of alkyl, aryl, or heteroaryl; each $R^4$ may be any of H, alkyl, aryl; and each X may be any of F, Cl, Br, I, Me, Bnz, $CH_2SiMe_3$, or C1 to C5 alkyls.

In another non-limiting embodiment of the compound represented by formula (XVI), M may be Ti, Zr, or Hf; $R^1$ may be any of $CH_2CH_2$, $(CH_2)_3$, $(CH_2)_4$, $CH_2CHMeCH_2$, $CH_2CMe_2CH_2$, $Me_2S_1$, $CH_2SiMe_2CH_2$, each $R^2$ may be any of an aryl group, defined here to bind through the 1-position to the BPP ring, with substituents in the 2-position or substituents in the 2 and 6 positions such as 2,4-$Me_2Ph$, 2,5-$Me_2Ph$, 2,6-$Me_2Ph$, 2,6-$Et_2Ph$, 2,6-$Pr_2$-Ph, 2,6-$Bu_2Ph$, 2-MeNapthyl, 2,4,6-$Me_3Ph$, 2,4,6-$Et_3Ph$, 2,4,6-$Pr_3Ph$, carbazole and substituted carbazoles; $R^3$ and $R^5$ through $R^9$ are H; each $R^4$ may be any of H, Methyl, Ethyl, Propyl, Butyl, Pentyl; and each X may be any of F, Cl, Br, I, Me, Bnz, $CH_2SiMe_3$, or C1 to C5 alkyls.

In one preferred embodiment, M may be either Zr or Hf; and X may be any of F, Cl, Br, I, Me, Bnz, or $CH_2SiMe_3$. In another preferred embodiment, M may be either Zr or Hf; $R^1$ may be either $(CH_2)_3$ or $(CH_2)_4$; each $R^2$ may be any of 2,6-Me2Ph, 2,6-Et2Ph, 2,6-Pr2-Ph, 2,6-Bu2Ph, 2-MeNapthyl, 2,4,6-Me3Ph, 2,4,6-Et3Ph, 2,4,6-Pr3Ph, and carbazole; each $R^4$ may be any of H, Methyl or Butyl; and X may be any of F, Cl, or Me. In even another preferred embodiment, the $R^1$ is $(CH_2)_3$; each $R^3$ is either 2,4,6-$Me_3Ph$ or 2-MeNapthyl; each $R^4$ is $CH_3$; X is Cl; and M is Zr.

In another non-limiting embodiment, the high molecular weight catalyst component may be any catalyst that produces a polymer having a weight average molecular weight (Mw) of greater than about 1 million g/mol, preferably greater than about 1.5 million g/mol, even more preferably greater than about 2 million g/mol, and still more preferably greater than about 3 million g/mol. The low molecular weight catalyst may be any catalyst that produces a polymer having a weight average molecular weight (Mw) in the range of from about 40,000 to about 200,000 g/mol, preferably from about 50,000 to about 180,000 g/mol, more preferably from about 60,000 to about 175,000 g/mol, and even more preferably from about 70,000 to about 150,000 g/mol. In one preferred embodiment, the high molecular weight catalyst produces polymer having an Mw greater than about 5 million g/mol, and the low molecular weight catalyst produces polymer having an Mw of about 100,000 g/mol.

The amount of each catalyst component present in the catalyst systems of the disclosure may be varied within a range. The amount of each catalyst component present in the catalyst systems may be dependent on one or more reaction parameters including but not limited to reactor temperature, hydrogen concentration, and comonomer concentration. The low molecular weight catalyst is generally present in an amount greater than that of the high molecular weight catalyst. Generally, the high molecular weight catalyst component is present in a catalyst system in an amount in a range of from about 0.001 to about 5.0 mol % of said low molecular weight catalyst component, preferably in a range of from about 0.05 to about 2.5 mol % of said low molecular weight catalyst component, more preferably in a range of from about 0.1 to about 2.0 mol % of said low molecular weight catalyst component. For example, in the case of one high and one low molecular weight catalyst, the mol % of the high molecular weight catalyst may be calculated from the equation: 100 (moles of high molecular weight catalyst)/(moles of low molecular weight catalyst+moles of high molecular weight catalyst).

Activators and Activation Methods

The above described low and high molecular weight precatalyst compounds can be combined with an activator and optionally a support or carrier in a manner that will allow production of a polymer with low and high molecular weight components. The term "cocatalyst" or "cocatalysts" may be used interchangeably with one or more "activators". This activation yields catalyst compounds capable of polymerizing olefins.

For the purposes of this patent specification and appended claims, the term "activator" is defined to be any compound or component or method which can activate any of the precatalyst metal compounds of the invention as described above. Non-limiting activators, for example may include a Lewis acid or a non-coordinating ionic activator or ionizing activator or any other compound including Lewis bases, aluminum alkyls, conventional-type cocatalysts or an activator-support and combinations thereof that can convert a neutral precatalyst metal compound to a catalytically active cationic metal compound. It is within the scope of this invention to use alumoxane or modified alumoxane as an activator, and/or to also use ionizing activators, neutral or ionic, such as tri (n-butyl)ammonium tetrakis(pentafluorophenyl)boron or a trisperfluorophenyl boron metalloid precursor or a trisperfluoronaphtyl boron metalloid precursor that would ionize the neutral precatalyst metal compound.

The low and high molecular weight catalyst precursors according to this invention may be activated for polymerization catalysis in any manner sufficient to allow coordination or cationic polymerization. This can be achieved for coordination polymerization when one ligand can be abstracted and another will either allow insertion of the unsaturated monomers or will be similarly abstractable for replacement with a ligand that allows insertion of the unsaturated monomer (labile ligands), eg. alkyl, silyl or hydride. The traditional activators of coordination polymerization art are suitable, those typically include Lewis acids such as alumoxane compounds, and ionizing, anion precursor compounds that abstract one so as to ionize the bridged metallocene metal center in to a cation and provide a counterbalancing noncoordianting ion. In one embodiment, an activation method using ionizing ionic compounds not containing an active proton but capable of producing both a cationic metal compound catalyst and a noncoordinating anion are also contemplated, and are described in EP-A-0 426 637, EP-A-0 573 403 and U.S. Pat. No. 5,387,568, which are all herein incorporated by reference.

Alkylalumoxanes and modified alkylalumoxane are suitable as catalyst activators, particularly for the invention metal compounds where $R^1$=halide or other functional group. Alkylalumoxanes and modified alkylalumoxane are also suitable as catalyst for the invention metal compounds where $R^1$=hydrocarbyl or substituted hydrocarbyl. In one embodiment, one or more alumoxanes are utilized as an activator in the catalyst composition of the invention. Alumoxanes, sometimes called aluminoxanes in the art, are generally oligomeric compounds containing —Al(R)—O— subunits, where R is an alkyl group. Examples of alumoxanes include methylalumoxane (MAO), modified methylalumoxane (MMAO), ethylalumoxane and isobutylalumoxane. Alkylalumoxanes and modified alkylalumoxanes are suitable as catalyst activators, particularly when the abstractable ligand is a halide. Mixtures of different alumoxanes and modified alumoxanes may also be used. For further descriptions, see U.S. Pat. Nos. 4,665,208, 4,952,540, 5,041,584, 5,091,352, 5,206,199, 5,204,419, 4,874,734, 4,924,018, 4,908,463, 4,968,827, 5,329,032, 5,248,801, 5,235,081, 5,157,137, 5,103,031 and EP 0 561 476 A1, EP 0 279 586 B1, EP 0 516 476 A, EP 0 594 218 A1 and WO 94/10180.

Alumoxanes may be produced by the hydrolysis of the respective trialkylaluminum compound. MMAO may be produced by the hydrolysis of trimethylaluminum and a higher trialkylaluminum such as triisobutylaluminum. MMAO's are generally more soluble in aliphatic solvents and more stable during storage. There are a variety of methods for preparing alumoxane and modified alumoxanes, non-limiting examples of which are described in U.S. Pat. Nos. 4,665,208, 4,952,540, 5,091,352, 5,206,199, 5,204,419, 4,874,734, 4,924,018, 4,908,463, 4,968,827, 5,308,815, 5,329,032, 5,248,801, 5,235,081, 5,157,137, 5,103,031, 5,391,793, 5,391,529, 5,693,838, 5,731,253, 5,731,451, 5,744,656, 5,847,177, 5,854,166, 5,856,256 and 5,939,346 and European publications EP-A-0 561 476, EP-B1-0 279 586, EP-A-0 594-218 and EP-B1-0 586 665, and PCT publications WO 94/10180 and WO 99/15534, all of which are herein fully incorporated by reference. It may be preferable to use a visually clear methylalumoxane. A cloudy or gelled alumoxane can be filtered to produce a clear solution or clear alumoxane can be decanted from the cloudy solution. Another preferred alumoxane is a modified methyl alumoxane (MMAO) cocatalyst type 3A (commercially available from Akzo Chemicals, Inc. under the trade name Modified Methylalumoxane type 3A, covered under U.S. Pat. No. 5,041,584).

Aluminum alkyl or organoaluminum compounds which may be utilized as activators (or scavengers) include trimethylaluminum, triethylaluminum, triisobutylaluminum, tri-n-hexylaluminum, tri-n-octylaluminum and the like.

It is within the scope of this invention to use an ionizing or stoichiometric activator, neutral or ionic, such as tri(n-butyl) ammonium tetrakis(pentafluorophenyl)boron, a trisperfluorophenyl boron metalloid precursor or a trisperfluoronaphtyl boron metalloid precursor, polyhalogenated heteroborane anions (WO 98/43983), boric acid (U.S. Pat. No. 5,942,459) or combination thereof. It is also within the scope of this invention to use neutral or ionic activators alone or in combination with alumoxane or modified alumoxane activators.

Examples of neutral stoichiometric activators include tri-substituted boron, tellurium, aluminum, gallium and indium or mixtures thereof. The three substituent groups are each independently selected from alkyls, alkenyls, halogen, substituted alkyls, aryls, arylhalides, alkoxy and halides. Preferably, the three groups are independently selected from halogen, mono or multicyclic (including halosubstituted) aryls, alkyls, and alkenyl compounds and mixtures thereof, preferred are alkenyl groups having 1 to 20 carbon atoms, alkyl groups having 1 to 20 carbon atoms, alkoxy groups having 1 to 20 carbon atoms and aryl groups having 3 to 20 carbon atoms (including substituted aryls). More preferably, the three groups are alkyls having 1 to 4 carbon groups, phenyl, naphthyl or mixtures thereof. Even more preferably, the three groups are halogenated, preferably fluorinated, aryl groups. Most preferably, the neutral stoichiometric activator is trisperfluorophenyl boron or trisperfluoronaphthyl boron.

Ionic stoichiometric activator compounds may contain an active proton, or some other cation associated with, but not coordinated to, or only loosely coordinated to, the remaining ion of the ionizing compound. Such compounds and the like are described in European publications EP-A-0 570 982, EP-A-0 520 732, EP-A-0 495 375, EP-B1-0 500 944, EP-A-0 277 003 and EP-A-0 277 004, and U.S. Pat. Nos. 5,153,157, 5,198,401, 5,066,741, 5,206,197, 5,241,025, 5,384,299 and 5,502,124 and U.S. patent application Ser. No. 08/285,380, filed Aug. 3, 1994, all of which are herein fully incorporated by reference.

Suitable anions are known in the art and will be suitable for use with the catalysts of the invention. See in particular, U.S. Pat. No. 5,278,119, WO2002102857, WO2002051884, WO200218452, WO2000037513, WO2000029454, WO2000004058, WO9964476, WO2003049856, WO2003051892, WO2003040070, WO2003000740, WO2002036639, WO2002000738, WO2002000666, WO2001081435, WO2001042249, WO2000004059. Also see the review articles by S. H. Strauss, "The Search for Larger and More Weakly Coordinating Anions", *Chem. Rev.*, 93, 927-942 (1993) and C. A. Reed, "Carboranes: A New Class of Weakly Coordinating Anions for Strong Electrophiles, Oxidants and Superacids", *Acc. Chem. Res.*, 31, 133-139 (1998).

Illustrative, but not limiting examples of boron compounds which may be used as an activating cocatalyst in the preparation of the improved catalysts of this invention are tri-substituted ammonium salts such as: trimethylammonium tetraphenylborate, triethylammonium tetraphenylborate, tripropylammonium tetraphenylborate, tri(n-butyl)ammonium tetraphenylborate, tri(t-butyl)ammonium tetraphenylborate, N,N-dimethylanilinium tetraphenylborate, N,N-diethylanilinium tetraphenylborate, N,N-dimethyl-(2,4,6-trimethylanilinium)tetraphenylborate, trimethylammonium tetrakis(pentafluorophenyl)borate, triethylammonium tetrakis(pentafluorophenyl)borate, tripropylammonium tetrakis(pentafluorophenyl)borate, tri(n-butyl)ammonium tetrakis(pentafluorophenyl)borate, tri(sec-butyl)ammonium tetrakis(pentafluorophenyl)borate, N,N-dimethylanilinium tetrakis(pentafluorophenyl)borate, N,N-diethylanilinium tetrakis(pentafluorophenyl)borate, N,N-dimethyl-(2,4,6-trimethylanilinium)tetrakis(pentafluorophenyl)borate, trimethylammonium tetrakis(heptafluoronaphthyl)borate, triethylammonium tetrakis(heptafluoronaphthyl)borate, tripropylammonium tetrakis(heptafluoronaphthyl)borate, tri(n-butyl)ammonium tetrakis(heptafluoronaphthyl)borate, tri(sec-butyl)ammonium tetrakis (heptafluoronaphthyl)borate, N,N-dimethylanilinium tetrakis(heptafluoronaphthyl)borate, N,N-diethylanilinium tetrakis(heptafluoronaphthyl)borate, trimethylammonium (2-perfluorobiphenyl)$_3$(perfluorophenylalkynyl)borate, triethylammonium (2-perfluorobiphenyl)$_3$(perfluorophenylalkynyl)borate, tripropylammonium (2-perfluorobiphenyl)$_3$(perfluorophenylalkynyl)borate, tri(n-butyl)ammonium (2-perfluorobiphenyl)$_3$(perfluorophenylalkynyl)borate, tri(sec-butyl)ammonium (2-perfluorobiphenyl)$_3$(perfluorophenylalkynyl)borate, N,N-dimethylanilinium (2-perfluorobiphenyl)$_3$(perfluorophenylalkynyl) borate, N,N-diethylanilinium (2-perfluorobiphenyl)$_3$(perfluorophenylalkynyl)borate, trimethylammonium tetrakis-(2,3,4,6-tetrafluorophenylborate, triethylammonium tetrakis-(2,3,4,6-tetrafluorophenyl)borate, tripropylammonium tetrakis-(2,3,4,6-tetrafluorophenyl)borate, tri(n-butyl)ammonium tetrakis(2,3,4,6-tetrafluoro-phenyl)borate, dimethyl(t-butyl)ammonium tetrakis-(2,3,4,6-tetrafluorophenyl)borate, N,N-dimethylanilinium tetrakis-(2,3,4,6-tetrafluorophenyl)borate, N,N-diethylanilinium tetrakis-(2,3,4,6-tetrafluoro-phenyl)borate, and N,N-dimethyl-(2,4,6-trimethylanilinium)tetrakis-(2,3,4,6-tetrafluorophenyl)borate; dialkyl ammonium salts such as: di-(i-propyl)ammonium tetrakis(pentafluorophenyl)borate, and dicyclohexylammonium tetrakis(pentafluorophenyl)borate; and tri-substituted phosphonium salts such as: triphenylphosphonium tetrakis(pentafluorophenyl)borate, tri(o-tolyl)phosphonium tetrakis(pentafluorophenyl)borate, and tri(2,6-dimethylphenyl)phosphonium tetrakis(pentafluorophenyl)borate; non-Bronsted acids such as triphenylcarbenium tetrakis(pentafluorophenyl)borate, triphenylcarbenium tetrakis(heptafluoronaphthyl)borate, triphenylcarbenium (2-perfluorobiphenyl)$_3$(perfluorophenylalkynyl)borate, trisperfluorophenyl borane, and triperfluoronaphthyl borane.

In general the combined activator and metal compounds are combined in ratios of about 1000:1 to about 0.5:1.

When the activator is an alumoxane (modified or unmodified), any quantity of alumoxane that activates a precatalyst metal compound may be used. Preferably, the ratio of Aluminum to the total molar amount of precatalyst or catalyst metal is between 1000:1 and 1:1. More preferably, the ratio is from 500:1 to 25:1. Even more preferably, the ratio is from 250:1 to 50:1. Even more preferably, the ratio is between 200:1 and 75:1.

When the activator is an ionizing activator, any quantity of ionizing activator that activates a precatalyst metal compound may be used. Preferably, the ratio of ionizing activator to the total molar amount of precatalyst or catalyst metal is between 10:1 and 1:10. More preferably, the ratio is from 5:1 to 1:5. Even more preferably, the ratio is from 4:1 to 1:4. Even more preferably, the ratio is between 2:1 and 1:2.

When a combination of activators is employed, any quantity of activators that activates precatalyst metal compounds may be used.

Supports and Methods of Supporting

In a preferred embodiment, the catalysts of the invention comprise high and low molecular weight catalyst precursors, an activator and a support material. Methods for preparing supported catalysts are well known in the art and are easily extendible to the preparation of catalysts with high and low molecular weight catalyst metal compounds.

The above described precatalyst metal compounds and activators may be combined with one or more support materials or carriers using one of the support methods well known in the art or as described below. In the preferred embodiment, the method of the invention uses a polymerization catalyst in a supported form. For example, in a most preferred embodiment, a catalyst system is in a supported form, for example deposited on, bonded to, contacted with, or incorporated within, adsorbed or absorbed in, or on, a support or carrier.

The terms "support" or "carrier" are used interchangeably and are any support material, preferably a porous support material, for example, talc, inorganic oxides and inorganic chlorides. Other carriers include resinous support materials such as polystyrene, functionalized or crosslinked organic supports, such as polystyrene divinyl benzene polyolefins or polymeric compounds, zeolites, clays, or any other organic or inorganic support material and the like, or mixtures thereof.

The preferred carriers are inorganic oxides that include those Group 2, 3, 4, 5, 13 or 14 metal oxides. The preferred supports include silica, alumina, silica-alumina, magnesium chloride, and mixtures thereof. Other useful supports include magnesia, titania, zirconia, montmorillonite (EP-B1 0 511 665) and the like. Also, combinations of these support materials may be used, for example, silica-chromium, silica-alumina, silica-titania and the like.

It is preferred that the carrier, most preferably an inorganic oxide, has a surface area in the range of from about 10 to about 700 $m^2/g$, pore volume in the range of from about 0.1 to about 4.0 mL/g and average particle size in the range of from about 5 to about 500 µm. More preferably, the surface area of the carrier is in the range of from about 50 to about 500 $m^2/g$, pore volume of from about 0.5 to about 3.5 mL/g and average particle size of from about 10 to about 200 µm. Most preferably the surface area of the carrier is in the range is from about 100 to about 400 $m^2/g$, pore volume from about 0.8 to about 3.0 mL/g and average particle size is from about 5 to about 100 The average pore size of the carrier of the invention typically has pore size in the range of from 10 to 1000 Å, preferably 50 to about 500 Å, and most preferably 75 to about 350 Å.

Examples of supporting catalyst systems are described in Hlalky, Chem. Rev. (2000), 100, 1347 1376 and Fink et al., Chem. Rev. (2000), 100, 1377 1390, U.S. Pat. Nos. 4,701,432, 4,808,561, 4,912,075, 4,925,821, 4,937,217, 5,008,228, 5,238,892, 5,240,894, 5,332,706, 5,346,925, 5,422,325, 5,466,649, 5,466,766, 5,468,702, 5,529,965, 5,554,704, 5,629,253, 5,639,835, 5,625,015, 5,643,847, 5,665,665, 5,698,487, 5,714,424, 5,723,400, 5,723,402, 5,731,261, 5,759,940, 5,767,032 and 5,770,664, U.S. application Ser. No. 271,598 filed Jul. 7, 1994 and Ser. No. 788,736 filed Jan. 23, 1997, and PCT Publication Nos. WO 95/32995, WO 95/14044, WO 96/06187 and WO 97/02297, all of which are herein fully incorporated by reference.

In one embodiment, the catalyst compounds of the invention may be deposited on the same or separate supports together with an activator, or the activator may be used in an unsupported form, or may be deposited on a support different from the supported catalyst metal compounds of the invention, or any combination thereof.

Polymerization Processes

The catalyst systems and polymerization processes of the present disclosure are directed to polymerization of one or more olefin monomers having from 2 to 30 carbon atoms. The catalysts and polymerization processes are particularly well suited to the polymerization of two or more olefin monomers of ethylene, propylene, 1-butene, 1-pentene, 1-hexene, 1-heptene, 1-octene, 1-nonene, 4-methyl-1-pentene, 1-isobutene, 1-isobutene and 1-decene. Other monomers useful in the processes of the disclosure include ethylenically unsaturated monomers, diolefins having 4 to 18 carbon atoms, conjugated or nonconjugated dienes, polyenes, vinyl monomers and cyclic olefins. Non-limiting monomers useful in the disclosure may include norbornene, norbornadiene, isobutylene, isoprene, vinylbenzocyclobutane, styrenes, alkyl substituted styrene, ethylidene norbornene, dicyclopentadiene and cyclopentene.

The present disclosure encompasses homopolymerization processes comprising a single olefin species such as ethylene or propylene, as well as copolymerization reactions between one olefin species (referred to herein as the "monomer" and "monomer compound") and at least a second olefin species (referred to herein as "comonomer" and "comonomer compound") different from the first species. Generally a copolymer will comprise a major amount of the monomer compound (i.e., greater than about 50 mole percent) and a minor amount of the comonomer (i.e., less than about 50 mole percent). The comonomers generally have from three to about 20 carbon atoms in their molecular chain and examples include, but are not limited to, propylene, 1-butene, 2-butene, 3-methyl-1-butene, isobutylene, 1-pentene, 2-pentene, 3-methyl-1-pentene, 4-methyl-1-pentene, 1-hexene, 2-hexene, 3-hexene, 3-ethyl-1-hexene, 1-heptene, 2-heptene, 3-heptene, the four normal octenes, the four normal nonenes, or the five normal decenes. In one non-limiting embodiment, a copolymer may comprise ethylene copolymerized with a comonomer selected from 1-butene, 1-pentene, 1-hexene, 1-octene, 1-decene, or styrene.

In another embodiment of the process of the invention, ethylene or propylene is polymerized with at least two different comonomers, optionally one of which may be a diene, to form a terpolymer. In one embodiment, two of the three monomers of the terpolymer are butene and ethylene. In one embodiment, the comonomer content is 1.0 to 20.0 wt %, or 2.0 to 15.0 wt %.

The polymerization processes of the present disclosure may be utilized for production of any polyolefin though preference is given to homopolymers and copolymers of polyethylene. In one non-limiting embodiment, the polyolefins are copolymers of ethylene and at least one comonomer selected from the group consisting of propylene, 1-butene, 1-pentene, 1-hexene, 1-heptene, 1-octene, and combinations thereof. In another non-limiting embodiment, the polyolefins are bimodal copolymers of ethylene and at least one comonomer selected from the group consisting of propylene, 1-butene, 1-pentene, 1-hexene, 1-heptene, 1-octene, and combinations thereof.

Polymerization reactors suitable for the present disclosure may be any type of reactor known in the art and may comprise at least one raw material feed system, at least one feed system for catalyst or catalyst components, at least one reactor system, at least one polymer recovery system or any suitable combination thereof. Suitable reactors for the present disclosure may further comprise any one or more of any of a catalyst storage system, an extrusion system, a cooling system, a diluent recycling system, or a control system. Such reactors may comprise continuous take-off and direct recycling of catalyst, diluent, and polymer. Generally, continuous processes may comprise the continuous introduction of a monomer, a catalyst, and optionally a diluent into a polymerization reactor and the continuous removal from this reactor of polymer and recycling of diluent and unreacted monomers and comonomers.

The comonomer, if present in the polymerization reactor, is present at any level that will achieve the desired weight percent incorporation of the comonomer into the finished polyethylene. This is expressed as a mole ratio of comonomer to ethylene as described herein, which is the ratio of the gas concentration of comonomer moles in the cycle gas to the gas concentration of ethylene moles in the cycle gas. In one embodiment, the comonomer is present with ethylene in the cycle gas in a mole ratio range of from 0 or 0.0001 (comonomer:ethylene) to 0.20 or 0.10, and from 0.001 to 0.080 in another embodiment, and from 0.001 to 0.050 in even another embodiment, and from 0.002 to 0.20 in still another embodiment. In yet another embodiment, the comonomer is present with ethylene in the cycle gas in a mole ratio range comprising any combination of any upper limit with any lower limit as described herein.

The processes of the present disclosure may be characterized in that the desired composition of high molecular weight to low molecular weight moiety can be achieved at any of the above comonomer to ethylene ratios.

Hydrogen, if present in the polymerization reactor, is present at any level that will achieve the desired melt index (MI, or I2) and molecular weights of the high and the low molecular weight component. Using the catalyst systems of the present disclosure increasing the concentration of hydrogen may increase the melt index of the polyolefin generated. MI can thus be influenced by the hydrogen concentration. The amount of hydrogen in the polymerization can be expressed as a mole ratio relative to the total polymerizable monomer, for example, ethylene, or a blend of ethylene and another alpha olefin. The amount of hydrogen used in the polymerization processes of the present disclosure is an amount necessary to achieve the desired MI of the final polyolefin resin.

In one embodiment, the ratio of hydrogen to total ethylene monomer (mol ppm H2:mol % ethylene) in the circulating gas stream is in a range of from 0 to 100, in a range of from 0.05 to 50 in another embodiment, in a range of from 0.10 to 40 in even another embodiment, and in a range of from 0.15 to 35 in still another embodiment. In yet another embodiment, the ratio of hydrogen to total ethylene monomer (mol ppm H2: mol % ethylene) in the circulating gas stream may be in a range comprising any combination of any upper mole ratio limit with any lower mole ratio limit described above.

The processes of the disclosure may be characterized in that the desired composition of high molecular weight to low molecular weight moiety can be achieved at any of the above hydrogen to ethylene ratios.

The process may also include "condensing agents" as is known in the art and disclosed in, for example, U.S. Pat. Nos. 4,543,399, 5,405,922 and 462,999. The condensing agent, if present in the reactor can be at any level that will achieve the desired increase in the dew point in order to improve cooling and ultimately space time yields. Suitable condensing agents include but are not limited to saturated hydrocarbons such as propane, n-butane, isobutane, n-pentane, isopentane, neopentane, n-hexane, isohexane, n-heptane, n-octane or mixtures thereof.

The catalysts and catalyst systems of the invention described above are suitable for use in any polymerization process over a wide range of temperatures and pressures. The temperatures may be in the range of from −60° C. to about 280° C., preferably from 50° C. to about 200° C., and the pressures employed may be in the range from 1 atmosphere to about 500 atmospheres or higher.

The polymerization processes of the disclosure may be carried out in solution, in bulk, in suspension, in gas-phase, in slurry-phase, as a high-pressure process, or any combinations thereof. Generally solution, gas-phase and slurry-phase processes are preferred. The processes may be carried out in any one or more stages and/or in any one or more reactor having any one or more reaction zone and are conducted substantially in the absence of catalyst poisons. As known by one of skill in the art, organometallic compounds may be employed as scavenging agents for poisons to increase the catalyst activity. The polymerization processes may be carried out batchwise, continuously run, or any combinations thereof. In one non-limiting embodiment, the polymerization processes of the present disclosure are carried out in a continuous gas-phase reactor. In another non-limiting embodiment, polymerization processes of the disclosure are carried out in a single gas-phase reactor.

Generally, the polymers of the disclosure comprise a high molecular weight component and a low molecular weight component. The polymers of the disclosure generally comprise from about 0.01 to about 25% of the high molecular weight component, preferably from about 0.05 to about 20%, more preferably from about 0.075 to about 15% of a very high molecular weight component, even more preferably from about 0.1 to about 12.5% of a very high molecular weight component, wherein the fraction of the high molecular weight component is determined by integrating the area under the molecular weight vs. dwt %/d Log M curve from molecular weight=1,000,000 to molecular weight=10,000,000.

As described previously, "high molecular weight" is defined herein as being greater than about 1,000,000 g/mol, preferably greater than about 1,500,000 g/mol, more preferably greater than about 2,000,000 g/mol, and even more preferably greater than about 3,000,000 g/mol. In one non-limiting embodiment, high molecular weight is greater than 5,000,000 g/mol. As described previously, "low molecular weight" is defined herein as being in the range of from about 40,000 to about 200,000 g/mol, preferably from about 50,000 to about 180,000 g/mol, more preferably from about 60,000 to about 175,000 g/mol, and even more preferably from about 70,000 to about 150,000 g/mol. In one non-limiting embodiment, low molecular weight is about 100,000 g/mol.

Generally the high molecular weight component comprises a molecular weight at least 10 times greater than the low molecular weight component, preferably at least 20 times greater than that of the low molecular weight component, more preferably at least 30 times greater than that of the low molecular weight component, and even more preferably at least 40 times greater than that of the low molecular weight component.

Generally the polymers of the disclosure may have a density in the range of from about 0.86 g/cc to 0.97 g/cm$^3$ as measured according to ASTM 1505-03.

The resins of the disclosure generally exhibit melt strength values greater than that of conventional linear or long chain branched polyethylene of similar melt index. As used herein "melt strength" refers to the force required to draw a molten polymer extrudate at a rate of 12 mm/s$^2$ at an extrusion temperature (190° C. and 250° C. were used herein) until breakage of the extrudate whereby the force is applied by take up rollers. The melt strength of the polymers of the disclosure, also referred to herein as "melt tension", may be expressed as a function of the embodiments, the MI value may be greater than $8*MI^{-0.6675}$. In still non-limiting embodiments, the MI value may be greater than $10*MI^{-0.6675}$.

In one non-limiting embodiment, the polymers of the present disclosure may have a melt index ("MI" or "I$_2$") as measured by ASTM-D-1238-E (190° C., 2.16 kg weight) in the range of from 0.001 dg/min to 25 dg/min. In other non-limiting embodiments, the polymers of the present disclosure may have a MI in a range of from about 0.001 dg/min to about 5 dg/min; in even other non-limiting embodiments a MI in a range of from about 0.01 dg/min to about 5 dg/min in other embodiments; and in still other non-limiting embodiments a MI in a range of from about 0.01 dg/min to about 1 dg/min.

In one non-limiting embodiment, the polymers of the present disclosure may have a melt flow ratio (MFR) in the range of from about 10 to 300. MFR is defined as $I_{21}/I_2$, wherein $I_{21}$ is measured by ASTM-D-1238-F, at 190° C., 21.6 kg weight. In other non-limiting embodiments, the polymers of the present disclosure may have a MFR in a range of from about 15 to 250; in even other non-limiting embodiments, a MFR in a range of from about 15 to 200; and in still other non-limiting embodiments a MFR in a range of from about 20 to 150.

As known by one of skill in the art, when subjected to uniaxial extension at a given strain rate, the extensional viscosity of a polymer increases with time. As also known by one of skill in the art, the transient uniaxial extensional viscosity of a linear polymer can be predicted. Strain hardening occurs when a polymer is subjected to uniaxial extension and the transient extensional viscosity increases more than what is predicted from linear viscoelastic theory. As defined herein, the strain hardening index is the ratio of the observed transient uniaxial extensional viscosity to the theoretically predicted transient uniaxial extensional viscosity. Strain hardening index is expressed herein as the following ratio:

$\eta_E^+$observed/$\eta_E^+$predicted.

At conditions characteristic of film blowing, for example strain rate of 1 sec$^{-1}$, temperature of 190° C., and time of 4 seconds (i.e., a strain (c) of 4), generally the strain hardening index of the polymers of the present disclosure is a ratio/value greater than 3 in some embodiments, a value greater than 5 in other embodiments, a value greater than 8 in even other embodiments, and a value greater than 10 in still other embodiments.

The polymers of the present disclosure may be characterized in that they exhibit an activation energy (Ea) of less than 7 kcal/mol/K. In other non-limiting embodiments, the Ea of the polymers of the present disclosure may be less than 6 kcal/mol/K.

In the present disclosure, the activation energy is determined from dynamic oscillatory shear rheology measurements at five different temperatures, 150° C., 170° C., 190° C., 210° C., 230° C. and 250° C. At each temperature, scans are performed as a function of angular shear frequency (from ω=100 rad/s to ω=0.01 rad/s) at a constant shear strain. Master curves of storage modulus, G', and loss modulus, G", are obtained by time-temperature (t-T) superposition and the flow activation energies ($E_a$) are obtained from an Arrhenius plot, $a_T$=exp($E_a$/kT), where 1/T is plotted as a function of ln($a_T$), which relates the shift factor ($a_T$) to $E_a$.

As known by one of skill in the art, rheological data may be presented by plotting the phase angle versus the absolute value of the complex shear modulus to produce a van Gurp-Palmen (vGP) plot. The vGP plot of conventional polyethylene polymers shows monotonic behavior and a negative slope toward higher G* values. Conventional LLDPE polymer both with and without long chain branches also exhibit a negative slope on a vGP plot. The vGP plots of the polymers described in the present disclosure exhibit two slopes—a positive slope at lower G* values and a negative slope at higher G* values.

Referring now to FIG. 1, there are shown van Gurp-Palmen (vGP or VGP) plots of various linear polyethylene resins: a conventional monodispersed PE (hydrogenated polyputadiene) (closed circles), a conventional metallocene LLDPE resin with a narrow molecular weight distribution (closed squares), a conventional bimodal resin having a broad molecular weight distribution (asterisk), and an inventive resin of the disclosure (closed diamonds). The molecular weights and molecular weight distributions of the conventional resins are shown in Table 1 below. Increasing polydispersity in comparative conventional resins stretches the curve along the abscissa, but does not change the monotonic nature of the vGP plot (note how their curves in FIG. 1 become less steep). The resin (Exceed™ 1018) and the bimodal resin (Borouge™ FB 2230) are commercially available resins. In non-limiting embodiments of the present disclosure, the introduction of a high molecular weight fraction according to the disclosure may change the shape of the vGP plot in that it causes a maximum in the vGP plot as shown in FIG. 1.

TABLE 1

| Resin | Grade | Mw | Mw/Mn |
|---|---|---|---|
| Anionically polymerized hydrogenated polybutadiene | | 87,400 g/mol | 1.02 |
| Metallocene PE resin | Exceed ™ 1018 | 101,000 g/mol | 2.2 |
| Dual reactor bimodal PE resin | Borouge ™ FB 2230 | 192800 | 20.4 |

In non-limiting embodiments, the ratio of the z-average molecular weight (Mz) to the weight average molecular weight (Mw) of the polymers of the present disclosure may be a ratio having a value in a range of from about 6 to 12. In other non-limiting embodiments, the Mz/Mw ratio may be a value in a range of from about 7 to 15. In even other non-limiting embodiments, the Mz/Mw ratio may be a value greater than 10. The ratio of the Mw to the number average molecular weight (Mn) (ratio of Mw/Mn is also referred to as polydispersity) can be in the range of from 2.5 to 8 in some non-limiting embodiments, from 3.0 to 10 in other non-limiting embodiments, and from 3.5 to 12 in even other non-limiting embodiments. Generally for the polymers of the disclosure, the Mz/Mw ratio is a value greater than the Mw/Mn ratio. As known in the art, Mn is the number average molecular weight and may be expressed as $\Sigma(M_iN_i)/\Sigma N_i$; Mw is the weight average molecular weight and may be expressed as $\Sigma(M_i^2N_i)/\Sigma(M_iN_i)$; and Mz is the z-average molecular weight of a polymer and may be expressed as $\Sigma(M_i^3N_i)/\Sigma(M_i^2N_i)$ wherein Ni is the number of molecules of molecular weight Mi. Techniques for determining these values are known in the art and any may be used herein.

The polymers of the disclosure generally show very high viscosities at low shear rates and exhibit strong shear thinning. A shear thinning index may be expressed as the ratio of the complex viscosities ($\eta^*$) at two given oscillatory shear frequencies, arbitrarily selected herein to be 0.01 rad/sec ($\eta^*_{0.01}$) and 100 rad/sec ($\eta^*_{100}$). Thus, the shear thinning index is expressed herein as ($\eta^*_{0.01}$)/($\eta^*_{100}$). Both ($\eta^*_{0.01}$) and ($\eta^*_{100}$) are obtained from oscillatory shear rheometry as described herein. The shear thinning index ($\eta_{0.01}/\eta^*_{100}$) of the polymers of the present disclosure may be a value in the range of 5 to 500. In other non-limiting embodiments, the shear thinning index may be in the range of 25 to 500. In even other embodiments, the shear thinning index may be in the range of 50 to 500. In still other embodiments, the shear thinning index may be in the range of 100 to 500.

The resins of the disclosure are suitable for use in a variety of products and end-use applications including, but not limited to film, sheets, laminating, jacketing, insulating, and a variety of articles produced by injection molding, blow molding, extrusion coating, profile extrusion, and combinations thereof.

EXAMPLES

It is to be understood that while the invention has been described in conjunction with the specific embodiments thereof, the foregoing description is intended to illustrate and not limit the scope of the invention. Other aspects, advantages and modifications will be apparent to those skilled in the art to which the invention pertains.

Therefore, the following examples are put forth so as to provide those skilled in the art with a complete disclosure and description of how to make and use the compounds of the invention, and are not intended to limit the scope of that which the inventors regard as their invention. Because of the high molecular weights of the polyethylene resins described herein, it is necessary to measure size exclusion chromatography at elevated temperatures to ensure adequate solubility of the polymer molecules. Molecular weights and molecular weight distributions of the resins described herein were determined using high temperature size exclusion chromatography.

Measurements of Molecular Weights and Molecular Weight Distributions

The molecular weights and molecular weight distributions of the resins described in the present disclosure were characterized using a High Temperature Size Exclusion Chromatograph (PL 220, Polymer Laboratories), equipped with a differential refractive index detector (DRI). Three Polymer Laboratories PLgel 10 mm Mixed-B columns were used. The nominal flow rate was 1.0 cm$^3$/min, and the nominal injection volume was 300 μL. The various transfer lines, columns and differential refractometer (the DRI detector) were contained in an oven maintained at 160 C.

Polymer solutions were prepared in filtered 1,2,4-Trichlorobenzene (TCB) containing 1000 ppm of butylated hydroxy toluene (BHT). The same solvent was used as the SEC eluent. Polymer solutions were prepared by dissolving the desired amount of dry polymer in the appropriate volume of SEC eluent to yield concentrations ranging from 0.5 to 1.5 mg/mL. The sample mixtures were heated at 160° C. with continuous agitation for about 2 to 2.5 hours. Sample solution will be filtered off-line before injecting to GPC with 2 μm filter using the Polymer Labs SP260 Sample Prep Station.

The separation efficiency of the column set was calibrated using a series of narrow MWD polystyrene standards, which reflects the expected MW range for samples and the exclusion limits of the column set. Eighteen individual polystyrene standards, ranging from Mp ~580 to 10,000,000, were used to generate the calibration curve. The polystyrene standards are obtained from Polymer Laboratories (Amherst, Mass.). To assure internal consistency, the flow rate is corrected for each calibrant run to give a common peak position for the flow rate marker (taken to be the positive inject peak) before determining the retention volume for each polystyrene standard. The flow marker peak position thus assigned was also used to correct the flow rate when analyzing samples; therefore, it is an essential part of the calibration procedure. A calibration curve (log Mp vs. retention volume) is generated by recording the retention volume at the peak in the DRI signal for each PS standard, and fitting this data set to a 2$^{nd}$-order polynomial. The equivalent polyethylene molecular weights are determined by using the following Mark-Houwink coefficients:

|    | k (dL/g)        | A     |
|----|-----------------|-------|
| PS | 1.75 × 10−4     | 0.67  |
| PE | 5.79 × 10−4     | 0.695 |

Dynamic Rheology

For dynamic oscillatory shear measurements, the resins were stabilized with 500 ppm of Irganox 1076 and 1500 ppm of Irgafos168. The measurements were carried out on an oscillatory rheometer (Rheometrics RDS-2, ARES) with 25 mm diameter parallel plates in a dynamic mode under nitrogen atmosphere. For all experiments, the rheometer was thermally stable at 190° C. for at least 30 minutes before inserting compression-molded sample of resin onto the parallel plates. To determine the samples viscoelastic behavior, frequency sweeps in the range from 0.01 to 100 rad/s were carried out at 190° C. under constant strain. To determine the activation energy, the sweeps were carried out at 5 different temperatures as described herein.

Structures of Precatalysts and Ligands

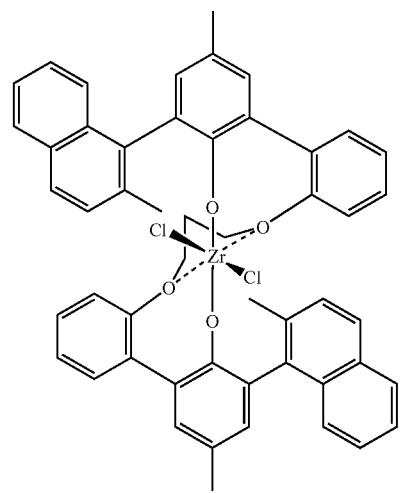

Precat A

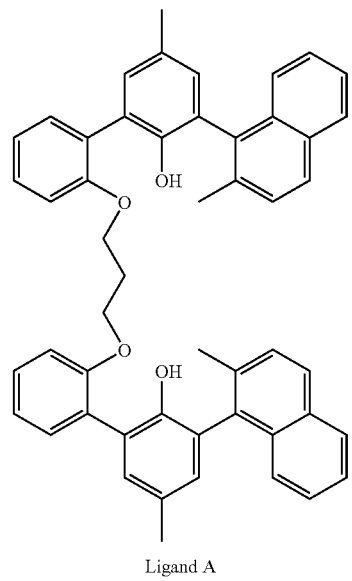

Ligand A

-continued

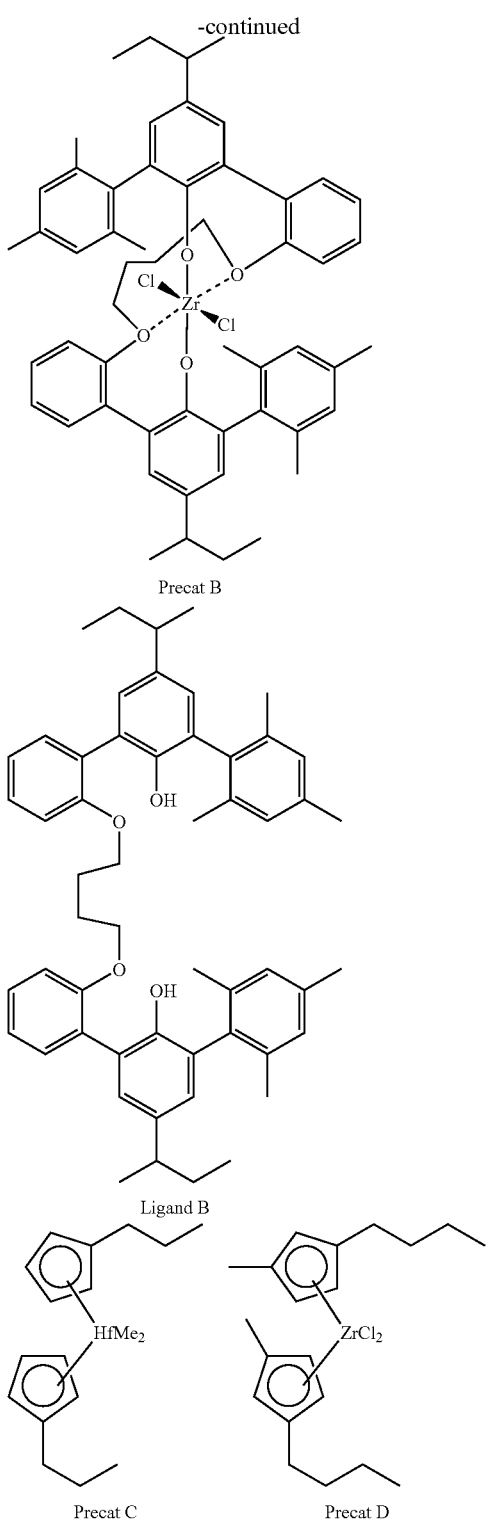

Precat B

Ligand B

Precat C    Precat D

Anhydrous oxygen free solvents were used. Thirty-weight percent methylaluminoxane (MAO) and (1-Me, 3-BuCp)$_2$ ZrCl$_2$ were obtained from Albemarle Corporation. (n-PrCp)$_2$ HfCl$_2$ was obtained from Boulder Scientific. (n-PrCp)$_2$ HfMe$_2$ may be prepared by methylation of (n-PrCp)$_2$HfCl$_2$ with methyl lithium in toluene. Ligand B was obtained from Symyx Technologies. Zr(CH$_2$Ph)$_2$Cl$_2$(OEt$_2$) was prepared by reaction of ZrBnz$_4$ and ZrCl$_4$ in diethyl ether. Catalyst E is a non-inventive supported catalyst prepared from Precat D, MAO and support used as a standard in gas-phase polymerizations to insure the reactor is running properly.

Example 1

Preparation of Ligand A

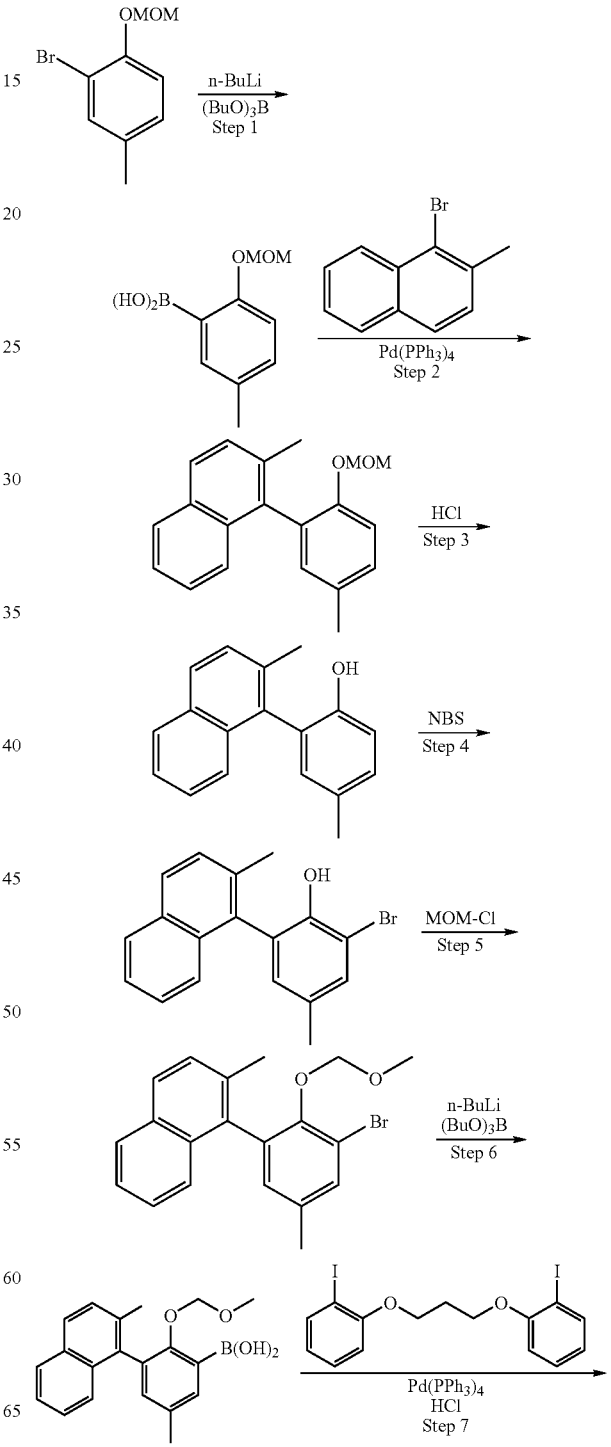

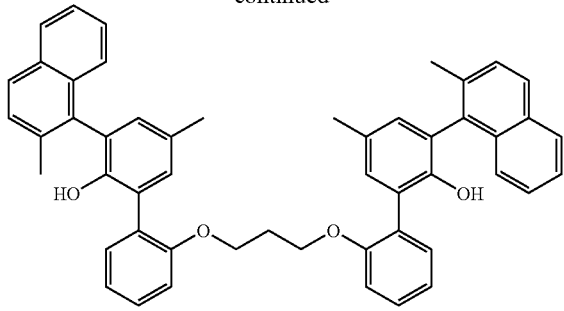

STEP 1. A solution of 30 g (0.13 mol, 1 eq) of O-MOM-bromo methyl compound in 300 ml of dry tetrahydrofuran was cooled to −76° C. 53 ml of n-butyl lithium (1.2 eq, 0.155 mol) was added in such a manner that the temperature did not rise beyond −70° C. The resulting mixture was stirred for another 4 hours at −78° C. 53 ml (0.18 mol, 1.4 eq) of n-butyl borate was then added to the reaction mass maintaining the temperature from −76° C. to −70° C. Stirring was then continued for another 5 hours after which the reaction mass was quenched with 150 ml of water. This was stirred for another 10 hrs. The organic layer and the aqueous layer were separated. The aqueous layer was washed with petroleum ether and the organic layer was washed with 10% sodium hydroxide solution. The aqueous layer and the sodium hydroxide layer were then combined and acidified using 505 conc. HCl solution. A white solid was obtained which was filtered off and dried under vacuum. Yield=20 g.

STEP 2. 15 g (0.067 mol, 1 eq) of 1-Bromo-2-methyl naphthalene, 0.4 g (5 mol %) of palladium tetrakis, 16 g (0.08 μmol, 1.2 eq) of—O-MOM boronic acid, 29 g of 2M solution of sodium carbonate and 150 ml of toluene were taken in a RB flask and heated to 120° C. After 16 hrs, the reaction mass was diluted with ethyl acetate and the two layers were separated. The resulting organic layer was washed with water followed by brine. This was then dried over sodium sulfate, filtered and concentrated. The crude obtained (25 g) was then taken for further step without any purification.

STEP 3. The 25 g of crude material obtained from STEP 2 was stirred along with 240 ml of methanolic HCl solution at RT for 16 hrs. The reaction mass was then diluted with excess of ethyl acetate. The organic layer was then washed with water followed by brine. This was then dried over sodium sulfate, filtered and concentrated. The crude obtained was then purified by column chromatography using 1% of ethyl acetate in petroleum ether. Yield=11.8 g.

STEP 4. 11.8 g (0.047 mol, 1 eq) of methynaphthyl phenol obtained from the above step and 7 ml (0.047 mol, 1 eq) of triethyl amine were taken in 110 ml of dry dichloromethane and stirred well. A solution of 13 g (0.007 mol, 1.5 eq) of N-bromo succinimide in 300 ml of dry dichloromethane was added over a period of 30 mins. The reaction mass was then stirred for 24 hours after which it was quenched with 1.5N HCl. The organic layer was separated and washed with water and brine. It was then dried over sodium sulfate and concentrated. The crude obtained (17 g) was then taken for further step without any purification as it was pure enough. (98%).

STEP 5. To a solution of 17 g (0.052 mol, 1 eq) of the bromo phenol compound and 43 ml (0.26 mol, 5 eq) of diisopropyl ethyl amine in 170 ml of dry dichloromethane, 16 ml (0.208 mol, 4 eq) of MOM chloride was added in drops. The resulting mass was stirred at RT for 16 hrs. The reaction mass was diluted with 1.5N HCl solution. The organic layer was separated and washed with water and brine. It was then dried over sodium sulfate and concentrated. The crude obtained was purified by column chromatography using petroleum ether and ethyl acetate as eluant which was 99% pure by HPLC. This was taken for the further step. Yield=12 g.

STEP 6. A solution of 12 g (0.0323 mol, 1 eq) of O-MOM-bromo compound in 120 ml of dry tetrahydrofuran was cooled to −76° C. To this 13.5 ml of n-butyl lithium (1.2 eq, 0.034 mol) was added in such a manner that the temperature did not rise beyond −70° C. The resulting mixture was stirred for another 1 hr at −78° C. 13 ml (0.045 mol, 1.4 eq) of n-butyl borate was then added to the reaction mass maintaining the temperature from −76° C. to −70° C. The reaction mass was then quenched with 50 ml of water and extraction was done in ethyl acetate. This was dried over sodium sulfate, filtered and concentrated. The crude (11 g) obtained was taken along with 3.7 g (10 mol %) of palladium tetrakis, 3.8 g (0.008 mol) of C3 iodo ether (prepared from the 2-iodophenol and 1,2-dibromopropane), 27 g (0.258 mol, 8 eq) of 2M solution of sodium carbonate and 120 ml of toluene, in a RB flask and heated to 120° C. After 16 hrs, the reaction mass was diluted with ethyl acetate and the two layers were separated. The resulting organic layer was washed with water followed by brine. This was then dried over sodium sulfate, filtered and concentrated. The crude obtained (17 g) was then taken for further step without any purification.

STEP 7. The 17 g of crude material obtained from STEP 6 was stirred along with 170 ml of methanolic HCl solution and 3 ml of dichloromethane at RT for 16 hrs. The reaction mass was then diluted with excess of ethyl acetate. The organic layer was then washed with water followed by brine. This was then dried over sodium sulfate, filtered and concentrated. The crude obtained was then purified by column chromatography using 1% of ethyl acetate in petroleum ether. Two fractions were collected and analyzed by HPLC, NMR and LCMS. The first fraction was 4 g and consisted of two isomers which were confirmed by NMR, LCMS AND HPLC. The second fraction (550 mg) also consists of two isomers which were confirmed by NMR and LCMS.

Example 2

Preparation of Precatalyst A

To a solution consisting of Ligand A (2.750 grams, 3.814 mmol) in approximately 80 milliliters of toluene was added a solution of $Zr(CH_2Ph)_2Cl_2(Et_2O)$ (1.603 grams) in 20 milliliters of toluene. An additional 20 milliliters of solvent were added to the mixture. After stirring the mixture at room temperature for 1 hour, the reaction was heated to 80° C. for 2 hours. Approximately 70% of the solvent was removed, and pentane added to induce further precipitation of the product. The mixture was chilled. The solids collected by filtration and washed with minimum pentane.

Example 3

Preparation of Precatalyst B

A solution of $Zr(CH_2Ph)_2Cl_2(Et_2O)_{12}$ (58.7 mg, 0.1355 mmol) in toluene (8 mL) was added to a hot solution (120° C.) of Ligand B (100 mg, 0.129 mmol) in toluene (32 mL) over a period of 5 minutes while stirring. After 15 min, the reaction was chilled and the solvent mostly removed. When there was 1-2 mL left, the solution was placed in about 15 mL of pentane. The solvents were reduced to ca ½ of the original volume. The slurry was decanted and the solids dried. Yield 39 mg.

Example 4

Preparation of Methyl Aluminoxane Supported on Silica (SMAO)

In a typical procedure, Crosfield ES757 silica (741 g), dehydrated at 600° C., was added to a stirred (overhead mechanical conical stirrer) mixture of toluene (2 L) and 30 wt % solution of methyl aluminoxane in toluene (874 g, 4.52 mol). The silica was chased with toluene (200 mL) then the mixture was heated to 90° C. for 3 h. Afterwards, volatiles were removed by application of vacuum and mild heat (40° C.) overnight then the solid was allowed to cool to room temperature.

Examples 5-21

Supported Catalyst Preparations

A solution of precatalysts (PC) and toluene was added at a rate of ca 0.5 mL/min to a slurry SMAO and pentane (amounts provided in Table 2 below), stirred with an overhead stirrer. After stirring for >30 min, the mixture was filtered and dried in-vacuo.

TABLE 2

Supported Catalyst preparations

| Example # | PC 1 | Mass of PC 1 (mg) | PC 2 | Mass of PC 2 (g) | SMAO (g) | Toluene (mL) | Pentane (mL) | mol % PC 1 |
|---|---|---|---|---|---|---|---|---|
| 5 | A | 1.4 | D | 1.3044 | 80.03 | 60 | 450 | 0.05 |
| 6 | A | 2.6 | D | 1.3 | 80.02 | 60 | 450 | 0.1 |
| 7 | A | 1.3 | D | 0.6469 | 40.01 | 30 | 375 | 0.1 |
| 8 | B | 6.7 | D | 0.647 | 40 | 30 | 375 | 0.48 |
| 9-Comparative | | | D | 0.8136 | 50.06 | 40 | 450 | 0 |
| 10 | B | 1.9 | D | 0.8133 | 50.07 | 30 | 375 | 0.11 |
| 11 | A | 1.5 | D | 0.8166 | 50 | 40 | 450 | 0.09 |
| 12 | A | 7.8 | D | 0.811 | 50 | 30 | 375 | 0.47 |
| 13 | B | 7.1 | D | 0.8113 | 50 | 30 | 375 | 0.4 |
| 14-Comparative | | | D | 0.814 | 50 | 40 | 450 | 0 |
| 15 | B | 1.4 | D | 0.5877 | 40.1 | 30 | 375 | 0.11 |
| 16 | A | 1.7 | D | 0.8127 | 50.02 | 40 | 450 | 0.1 |
| 17-Comparative | | | C | 0.7941 | 50 | 20 | 300 | 0 |
| 18 | A | 1.3 | C | 0.6337 | 39.99 | 50 | 450 | 0.1 |
| 19 | A | 3.3 | C | 0.6339 | 39.95 | 65.4 | 450 | 0.25 |
| 20 | A | 6.6 | C | 0.6363 | 39.9 | 90.8 | 450 | 0.5 |

Examples 22-42

Polymerization Testing in a Continuous Fluidized Bed Reactor

These catalysts were tested in a continuous fluidized-bed gas-phase reactor with a nominal 14" reactor diameter, an average bed weight of about 1900 g, gas-velocity of about 1.6 ft/s, production rate of about 500 g/h. The reactor was operated at a temperature of 79.4° C., and a pressure of 300 psig. The composition of ethylene, hydrogen, and 1-hexene is indicated in Table 3 below; the balance being nitrogen.

TABLE 3

Summary of Polymerization conditions

| Example | Catalyst from Example | H2 conc. (molppm) | Comonomer conc. (mol %) | C2 conc. (mol %) | Residence Time (h) |
|---|---|---|---|---|---|
| 21-comparative | E | 251 | 1.083 | 35.0 | 3.8 |
| 22 | 5 | 246 | 1.109 | 35.0 | 4.2 |
| 23 | 6 | 244 | 1.097 | 35.0 | 3.6 |
| 24-comparative | E | 123 | 0.619 | 34.7 | 4.0 |
| 25-comparative | E | 89 | 0.618 | 35.0 | 4.7 |
| 26 | 7 | 85 | 0.627 | 35.0 | 3.7 |
| 27 | 8 | 94 | 0.725 | 35.1 | 4.3 |
| 28 | 8 | 90 | 0.679 | 34.7 | 3.8 |
| 29-comparative | 9 | 91 | 0.342 | 35.2 | 5.0 |
| 30 | 10 | 99 | 0.312 | 35.1 | 5.7 |
| 31 | 11 | 97 | 0.291 | 35.0 | 3.7 |
| 32 | 12 | 103 | 0.282 | 35.0 | 4.0 |
| 33 | 13 | 102 | 0.320 | 35.0 | 4.2 |
| 34-comparative | 14 and 9 | 85 | 0.179 | 35.0 | 4.2 |
| 35 | 15 and 10 | 84 | 0.171 | 35.0 | 3.3 |
| 36 | 16 and 11 | 82 | 0.178 | 35.0 | 3.3 |

TABLE 3-continued

Summary of Polymerization conditions

| Example | Catalyst from Example | H2 conc. (molppm) | Comonomer conc. (mol %) | C2 conc. (mol %) | Residence Time (h) |
|---|---|---|---|---|---|
| 37 | 13 | 86 | 0.197 | 35.0 | 5.0 |
| 38-comparative | E | 84 | 0.057 | 35.0 | 6.0 |
| 39- | 17 | 115 | 0.019 | 35.0 | 4.1 |

TABLE 3-continued

Summary of Polymerization conditions

| Example | Catalyst from Example | H2 conc. (molppm) | Comonomer conc. (mol %) | C2 conc. (mol %) | Residence Time (h) |
|---|---|---|---|---|---|
| comparative | | | | | |
| 40 | 18 | 115 | 0.003 | 35.0 | 4.0 |
| 41 | 19 | 117 | 0.009 | 35.0 | 4.3 |
| 42 | 20 | 114 | 0.003 | 35.0 | 4.4 |

Example 43

Catalyst Evaluation/Polymer Production in LGPR

The test catalysts were evaluated in a continuous run gas phase reactor R125 (LGPR). The reactor was lined out with standard E catalyst at conditions used to make 1.2 MI, 0.917 density (LGPR condition 51-2006). Product was collected and the reactor was transitioned to each of the other catalysts.

Ethylene/1-hexene copolymers were produced according to the following procedure. The catalyst composition was injected dry into a fluidized bed gas phase polymerization reactor. More particularly, polymerization was conducted in a 152.4 mm diameter gas-phase fluidized bed reactor operating at approximately 2068 kPa total pressure. The reactor bed weight was approximately 2 kg. Fluidizing gas was passed through the bed at a velocity of approximately 0.6 m per second. The fluidizing gas exiting the bed entered a resin disengaging zone located at the upper portion of the reactor. The fluidizing gas then entered a recycle loop and passed through a cycle gas compressor and water-cooled heat exchanger. The shell side water temperature was adjusted to maintain the reactor temperature as specified in Tables 4-8. Ethylene, hydrogen, 1-hexene and nitrogen were fed to the cycle gas loop just upstream of the compressor at quantities sufficient to maintain the desired gas concentrations as specified in Tables 4-8. Gas concentrations were measured by an on-line vapor fraction analyzer. Product (polyethylene particles) was continuously withdrawn from the reactor in batch mode into a purging vessel before it was transferred into a product bin. Residual catalyst and activator in the resin was deactivated in the product drum with a wet nitrogen purge. The catalyst was fed to the reactor bed through a stainless steel injection tube at a rate sufficient to maintain the desired polymer production rate. "$C_6/C_2$ flow ratio ("FR")" is the ratio of the lbs of 1-hexene comonomer feed to the pounds of ethylene feed to the reactor, whereas the $C_6/C_2$ ratio is the ratio of the gas concentration of 1-hexene moles in the cycle gas to the gas concentration of ethylene moles in the cycle gas. The $C_6/C_2$ ratio is obtained from a cycle gas vapor fraction analyzer, whereas the $C_6/C_2$ Flow Ratio comes from some measure of the mass flow. The cycle gas is the gas in the reactor, and is measured from a tap off the recirculating loop around the reactor. The ratios reported in the following tables are from the gas concentrations in the reactor. Samples are taken every 9 min, and thus reported $C_6/C_2$ ratios are running averages. Tables 4-8 provide summaries of run conditions and product properties of non-limiting examples of the present disclosure for resins with densities of 0.91-0.95 as indicated in the tables.

The MI and HLMI values reported in Tables 4-8 as "QC, reactor granules" were obtained from the polymer granules that were isolated from the polymerization reactor. Each granular resin was dry-blended with 1500 ppm BHT (2,6-bis (1,1-dimethylethyl)-4-methylphenol). MI and HLMI were then measured according to ASTM-D-1238-E and ASTM D-1238-F, respectively.

The MI and HLMI values reported in Tables 4-8 as "ASTM, pellets" were obtained from compounded resins. To compound the resins, 500 ppm Irganox 1076 and 1500 ppm Igrafos 168 (both available from Ciba Chemicals) were added to the reactor granules and the admixture extruded using a ¾" Haake twin screw extruder. The melt temperature was 210° C. The output rate was about 3.5 lbs/hr. The MI and HLMI of the pellets were then measured according to ASTM-D-1238-E and ASTM D-1238-F, respectively.

The density values reported in Tables 4-8 as "QC, reactor granules" were obtained from the polymer granules that were isolated from the polymerization reactor. Each granular resin was dry-blended with 1500 ppm BHT and compression molded plaques were produced by heating the polymers in a mold to 179° C. and subsequently cooling them to 23° C. at a rate of 15° C. The molding pressure was chosen such that air pockets are removed and a uniform samples result. The density was then determined by immersing solid specimens of the compression molded plaques in a column filled with liquid of uniformly gradient density. The gradient density was in accordance with ASTM 1505.

The density values reported in Tables 4-8 as "ASTM, pellets" were obtained from compounded resins. To compound the resins, 500 ppm Irganox 1076 and 1500 ppm Igrafos 168 were added to the reactor granules and the admixture extruded using a ¾" Haake twin screw extruder. The melt temperature was 210° C. The output rate was about 3.5 lbs/hr. The density of the pellets was then measured according to ASTM 1505-03.

TABLE 4A

Summary of Process Data - resin density 0.91

| | Example | | |
|---|---|---|---|
| | 21 | 22 | 23 |
| | Catalyst from Example | | |
| | E | 5 | 6 |
| PROCESS DATA | | | |
| H2 conc. (molppm) | 251 | 246 | 244 |
| Hydrogen flow (sccm) | 6.72 | 6.22 | 6.88 |
| Comonomer conc. (mol %) | 1.083 | 1.109 | 1.097 |
| C2 conc. (mol %) | 35.0 | 35.0 | 35.0 |
| Comonomer/C2 Flow Ratio | 0.135 | 0.135 | 0.135 |
| C2 flow (g/hr) | 590 | 606 | 624 |
| H2/C2 Ratio | 7.2 | 7.0 | 7.0 |
| Comonomer/C2 Ratio | 0.031 | 0.032 | 0.031 |
| Rx. Pressure (psig) | 300 | 300 | 300 |
| Reactor Temp (F.) | 175 | 175 | 175 |
| Avg. Bedweight (g) | 1894 | 1930 | 1903 |
| Production (g/hr) | 494 | 462 | 533 |
| Residence Time (hr) | 3.8 | 4.2 | 3.6 |
| C2 Utilization (gC2/gC2 poly) | 1.19 | 1.31 | 1.17 |
| Avg Velocity (ft/s) | 1.58 | 1.57 | 1.46 |
| Catalyst Timer (minutes) | 15.0 | 50.0 | 38.0 |
| Catalyst Feed (g/hr) | 0.694 | 0.208 | 0.274 |
| Cat Prod. (g/g) - MB (new = .249) | 496 | 1546 | 1356 |
| Product Data | | | |
| Bulk Density | 0.3565 | | 0.3993 |
| Powder Flow Time | 7.63 | | 7.25 |
| Total Production (grams) | 26978 | 12717 | 18669 |
| Number of Bedturnovers | 14.2 | 6.6 | 9.8 |

TABLE 4A-continued

Summary of Process Data - resin density 0.91

| | Example 21 | Example 22 | Example 23 |
|---|---|---|---|
| | Catalyst from Example | | |
| | E | 5 | 6 |
| Basic Resin Data (QC) | | | |
| MI (QC reactor granules) | 5.92 | 5.47 | 4.51 |
| HLMI (QC reactor granules) | 112.31 | | 104.81 |
| HLMI/MI (QC reactor granules) | 18.97 | | 23.24 |
| Density (QC reactor granules) | 0.9115 | 0.9107 | 0.9105 |

TABLE 4B

Summary of Resin Data - resin density 0.91

| | Example 21 | Example 22 | Example 23 |
|---|---|---|---|
| | Catalyst from Example | | |
| Product Data | E | 5 | 6 |
| Resin 00270-153 | 020 | 030 | 040 |
| MI (ASTM, pellets) | 5.69 | 5.31 | 4.4 |
| HLMI (ASTM, pellets) | 112.70 | 100.10 | 83.7 |
| HLMI/MI (ASTM, pellets) | 18.90 | 18.90 | 18.8 |
| Density (ASTM, pellets) | 0.9124 | 0.9110 | 0.9118 |

TABLE 5A

Summary of Process Data - resin density 0.92

| | Example 24 | Example 25 | Example 26 | Example 27 | Example 28 |
|---|---|---|---|---|---|
| | Catalyst from Example | | | | |
| | E | E | 7 | 8 | 8 |
| PROCESS DATA | | | | | |
| H2 conc. (molppm) | 123 | 89 | 85 | 94 | 90 |
| Hydrogen flow (sccm) | 4.22 | 1.75 | 1.45 | 1.45 | 1.45 |
| Comonomer conc. (mol %) | 0.619 | 0.618 | 0.627 | 0.725 | 0.679 |
| C2 conc. (mol %) | 34.7 | 35.0 | 35.0 | 35.1 | 34.7 |
| Comonomer/C2 Flow Ratio | 0.088 | 0.085 | 0.084 | 0.084 | 0.084 |
| C2 flow (g/hr) | 631 | 546 | 647 | 504 | 660 |
| H2/C2 Ratio | 3.5 | 2.5 | 2.4 | 2.7 | 2.6 |
| Comonomer/C2 Ratio | 0.018 | 0.018 | 0.018 | 0.021 | 0.020 |
| Rx. Pressure (psig) | 300 | 300 | 300 | 300 | 300 |
| Reactor Temp (F.) | 175 | 175 | 175 | 175 | 175 |
| Avg. Bedweight (g) | 1946 | 1852 | 1834 | 1824 | 1937 |
| Production (g/hr) | 491 | 397 | 497 | 427 | 505 |
| Residence Time (hr) | 4.0 | 4.7 | 3.7 | 4.3 | 3.8 |
| C2 Utilization (gC2/gC2 poly) | 1.29 | 1.37 | 1.30 | 1.18 | 1.31 |
| Avg Velocity (ft/s) | 1.51 | 1.53 | 1.45 | 1.53 | 1.52 |
| Catalyst Timer (minutes) | 17.5 | 20.0 | 20.0 | 14.0 | 16.0 |
| Catalyst Feed (g/hr) | 0.596 | 0.521 | 0.521 | 0.744 | 0.651 |
| Cat Prod. (g/g) - MB (new = .249) | 574 | 532 | 665 | 400 | 541 |
| Product Data | | | | | |
| Melt Index (MI) (QC reactor granules) | 2.22 | 1.21 | 0.69 | 0.12 | 0.12 |
| HLMI (QC reactor granules) | 39.05 | 21.56 | 13.40 | 2.03 | n/a |
| HLMI/MI Ratio | 17.59 | 17.82 | 19.42 | 16.92 | n/a |
| Gradient Density (QC reactor granules) | 0.9186 | 0.9174 | 0.9176 | 0.9181 | 0.9177 |
| Bulk Density | n/a | 0.3718 | n/a | 0.3980 | n/a |
| Powder Flow Time | n/a | 7.7 | 7.5 | 7.3 | n/a |
| Total Production (grams) | 7853.0 | 8738.0 | 10929.0 | 8536.0 | 10096.0 |
| Number of Bedturnovers | 4.0 | 4.7 | 6.0 | 4.7 | 5.2 |
| NOTES | Trouble with H2 analyzer and H2 flow control | | | cat feeder problems at end of run. | |

TABLE 5B

Summary of Resin Data - resin density 0.92

| | | Data Point | | | |
|---|---|---|---|---|---|
| 050-2006 | 051-2006 | 052-2006 | | 054-2006 | 055-2006 |
| | | Example | | | |
| 24 | 25 | 26 | | 27 | 28 |
| | | Catalyst from Example | | | |
| E | E | 7 | | 8 | 8 |

| Product Data | | | | | |
|---|---|---|---|---|---|
| Resin 00270-128 | no sample | 100 | | | |
| MI (ASTM, pellets) | | 1.33 | 0.6 | 0.7 | 0.1 | 0.1 |
| HLMI (ASTM, pellets) | | 22.17 | 13.5 | 14.0 | 5.5 | 5.3 |
| HLMI/MI | | 16.66 | 22.9 | 20.2 | 68.1 | 57.0 |
| Density (ASTM, pellets) | | 0.9171 | 0.9164 | 0.9167 | 0.9172 | 0.9171 |
| Melt Strength (190 C.) | | 13.10 | 18.60 | 15.80 | 17.10 | too high |
| Melt Strength (250 C.) | | 6.10 | 9.60 | 8.90 | 10.00 | 34.90 |
| Shear Thinning Index | | 3.40 | 21.90 | 8.70 | 99.70 | 166.80 |
| Strain Hardening Index | | 1.12 | 6.80 | 4.64 | 8.68 | 250.78 |
| Ea | | No data | No data | No data | No data | No data |
| GPC-3d | | | | | | |
| Mw | | 40033 | 35164 | 42025 | 47289 | 49199 |
| Mw | | 105638 | 130295 | 147701 | 245554 | 243126 |
| Mz | | 189208 | 720683 | 864299 | 1719040 | 1915233 |
| Mw/Mn | | 2.64 | 3.71 | 3.51 | 5.19 | 4.94 |
| Mz/Mw | | 1.79 | 5.53 | 5.85 | 7.00 | 7.88 |

TABLE 6A

Summary of Process Data - resin density 0.93

| | Example | | | | |
|---|---|---|---|---|---|
| | 29 | 30 | 31 | 32 | 33 |
| | | | Catalyst from Example | | |
| | 9 | 10 | 11 | 12 | 13 |

| Process Data | | | | | |
|---|---|---|---|---|---|
| H2 conc. (molppm) | 91 | 99 | 97 | 103 | 102 |
| Hydrogen flow (sccm) | 20.09 | 4.29 | 3.60 | 5.14 | 2.73 |
| Comonomer conc. (mol %) | 0.342 | 0.312 | 0.291 | 0.282 | 0.320 |
| C2 conc. (mol %) | 35.2 | 35.1 | 35.0 | 35.0 | 35.0 |
| Comonomer/C2 Flow Ratio | 0.035 | 0.035 | 0.035 | 0.035 | 0.035 |
| C2 flow (g/hr) | 707 | 602 | 689 | 718 | 711 |
| H2/C2 Ratio | 2.6 | 2.8 | 2.8 | 2.9 | 2.9 |
| Comonomer/C2 Ratio | 0.010 | 0.009 | 0.008 | 0.008 | 0.009 |
| Rx. Pressure (psig) | 300 | 300 | 300 | 300 | 300 |
| Reactor Temp (F.) | 175 | 175 | 175 | 175 | 175 |
| Avg. Bedweight (g) | 1864 | 1865 | 1878 | 1932 | 1939 |
| Production (g/hr) | 375 | 330 | 508 | 487 | 459 |
| Residence Time (hr) | 5.0 | 5.7 | 3.7 | 4.0 | 4.2 |
| C2 Utilization (gC2/gC2 poly) | 1.89 | 1.82 | 1.36 | 1.48 | 1.55 |
| Avg Velocity (ft/s) | 1.57 | 1.58 | 1.58 | 1.58 | 1.58 |
| Catalyst Timer (minutes) | 28.0 | 24.4 | 20.0 | 23.2 | 23.0 |
| Catalyst Feed (g/hr) | 0.372 | 0.426 | 0.521 | 0.449 | 0.453 |
| Cat Prod. (g/g) - MB (new = .249) | 703 | 540 | 680 | 756 | 707 |
| Bulk Density | 0.4018 | 0.4103 | 0.4178 | 0.4298 | 0.4360 |
| Powder Flow Time | 7.16 | 7.78 | 8.10 | 9.22 | 9.32 |
| Total Production (grams) | 28274 | 15410 | 14385 | 20990 | 15082 |
| Number of Bedturnovers | 15.2 | 8.3 | 7.7 | 10.9 | 7.8 |
| Basic Resin Data | | | | | |
| MI (QC reactor granules) | 1.25 | 1.1 | 0.9 | 0.7 | 0.1 |
| HLMI (QC reactor granules) | 22.32 | 21.8 | 21.1 | 19.4 | 9.0 |
| HLMI/MI | 17.80 | 19.9 | 23.2 | 26.7 | 100.8 |
| Density (QC reactor granules) | 0.9285 | 0.9294 | 0.9305 | 0.9310 | 0.9280 |

TABLE 6B

Summary of Resin Data - resin density 0.93

| | Data Point | | | | |
|---|---|---|---|---|---|
| | 5-2__2007 | 5-3__2007 | 5-4__2007 | 5-5__2007 | 5-6__2007 |
| | | | Example | | |
| | 29 | 30 | 31 | 32 | 33 |
| | | | Catalyst from Example | | |
| | 9 | 10 | 11 | 12 | 13 |
| Resin 00270-136 | 100 | 200 | 300 | 400 | 500 |
| MI (ASTM, pellets) | 1.25 | 1.1 | 0.9 | 0.7 | 0.1 |
| HLMI (ASTM, pellets) | 22.32 | 21.8 | 21.1 | 19.4 | 9.0 |
| HLMI/MI | 17.80 | 19.9 | 23.2 | 26.7 | 100.8 |
| Density (ASTM, pellets) | 0.9285 | 0.9294 | 0.9305 | 0.9310 | 0.9280 |
| Melt Strength (190 C.) | 13.10 | 18.60 | 15.80 | 17.10 | too high |
| Melt Strength (250 C.) | 6.10 | 9.60 | 8.90 | 10.00 | 34.90 |
| Shear Thinning Index | | 21.97 | No data | No data | 248.23 |
| Strain Hardening Index | 4.00 | 4.41 | 5.42 | 4.41 | 14.48 |
| Ea | | 7.02 | No data | No data | 5.57 |
| GPC-3d | | | | | |
| Mw | 37426 | 36032 | 36872 | 31984 | 42374 |
| Mw | 120938 | 136675 | 138060 | 162940 | 265891 |
| Mz | 683380 | 1022488 | 1047292 | 1285485 | 2227940 |
| Mw/Mn | 3.23 | 3.79 | 3.74 | 5.09 | 6.27 |
| Mz/Mw | 5.65 | 7.48 | 7.59 | 7.89 | 8.38 |

TABLE 7A

Summary of Process Data - resin density 0.94

| | Example | | | |
|---|---|---|---|---|
| | 34 | 35 | 36 | 37 |
| | | Catalyst from Example | | |
| | 14 and 9 | 15 and 10 | 16 and 11 | 13 |
| PROCESS DATA | | | | |
| H2 conc. (molppm) | 85 | 84 | 82 | 86 |
| Hydrogen flow (sccm) | 7.37 | 7.54 | 6.04 | 3.97 |
| Comonomer conc. (mol %) | 0.179 | 0.171 | 0.178 | 0.197 |
| C2 conc. (mol %) | 35.0 | 35.0 | 35.0 | 35.0 |
| Comonomer/C2 Flow Ratio | 0.020 | 0.020 | 0.020 | 0.020 |
| C2 flow (g/hr) | 736 | 739 | 635 | 408 |
| H2/C2 Ratio | 2.4 | 2.4 | 2.4 | 2.5 |
| Comonomer/C2 Ratio | 0.005 | 0.005 | 0.005 | 0.006 |
| Rx. Pressure (psig) | 300 | 300 | 300 | 300 |
| Reactor Temp (F.) | 175 | 175 | 175 | 175 |
| Avg. Bedweight (g) | 1844 | 1917 | 1857 | 1909 |
| Production (g/hr) | 443 | 588 | 567 | 380 |
| Residence Time (hr) | 4.2 | 3.3 | 3.3 | 5.0 |
| C2 Utilization (gC2/gC2 poly) | 1.66 | 1.26 | 1.12 | 1.07 |
| Avg Velocity (ft/s) | 1.48 | 1.46 | 1.46 | 1.46 |
| Catalyst Timer (minutes) | 18.0 | 19.0 | 16.3 | 22.0 |
| Catalyst Feed (g/hr) | 0.578 | 0.548 | 0.641 | 0.473 |
| Cat Prod. (g/g) - MB(new = .249) | 534 | 748 | 617 | 560 |
| Product Data | | | | |
| Bulk Density | 0.4128 | 0.4500 | 0.4353 | 0.4478 |
| Powder Flow Time | 8.40 | 9.29 | 7.41 | 8.81 |
| Total Production (grams) | 16222 | 14429 | 16463 | 15649 |
| Number of Bedturnovers | 8.8 | 7.5 | 8.9 | 8.2 |
| Basic Resin Data | | | | |
| MI (QC reactor granules) | 1.81 | 1.75 | 1.45 | 1.28 |
| HLMI (QC reactor granules) | 36.19 | 34.26 | 30.36 | 28.25 |
| HLMI/MI | 20.03 | 20.03 | 20.03 | 20.03 |
| Density (QC reactor granules) | 0.9354 | 0.9373 | 0.9373 | 0.9377 |

TABLE 7B

Summary of Resin Data - resin density 0.94

| | Example | | | |
|---|---|---|---|---|
| | 34 | 35 | 36 | 37 |
| | Catalyst from Example | | | |
| | 14 and 9 | 15 and 10 | 16 and 11 | 13 |
| Product Data | | | | |
| MI (ASTM, pellets) | 1.81 | 1.75 | 1.45 | 1.28 |
| HLMI (ASTM, pellets) | 36.19 | 34.26 | 30.36 | 28.25 |
| HLMI/MI | 20.03 | 20.03 | 20.03 | 20.03 |
| Density (ASTM, pellets) | 0.9381 | 0.9375 | 0.9379 | 0.9378 |
| Melt Strength (190 C.) | 13.10 | 18.60 | 15.80 | too high |
| Melt Strength (250 C.) | 6.10 | 9.60 | 8.90 | 34.90 |
| Shear Thinning Index | 5.37 | 4.63 | 19.82 | 80.60 |
| Strain Hardening Index | n/a | 1.00 | 4.14 | 16.64 |
| Ea | | in progress | in progress | in progress |
| GPC-3d | | | | |
| Mn | 26352 | 29682 | 27576 | 28242 |
| Mw | 90911 | 93851 | 94584 | 125147 |
| Mz | 170268 | 176178 | 240151 | 769345 |
| Mw/Mn | 3.45 | 3.16 | 3.43 | 4.43 |
| Mz/Mw | 1.87 | 1.88 | 2.54 | 6.15 |

TABLE 8A

Summary of Process Data - resin density 0.95

| | Data Point | | | | |
|---|---|---|---|---|---|
| | 303-153 | 303-154 | 303-155 | 303-156 | |
| | Example | | | | |
| | 38 | 39 | 40 | 41 | 42 |
| | Catalyst from Example | | | | |
| | E | 17 | 18 | 19 | 20 |
| Start Time | 1700 | 1500 | 1900 | 300 | 2300 |
| Finish Time next day | 1100 same day | 500 | 700 | 1100 same day | 1500 |
| PROCESS DATA | | | | | |
| H2 conc. (molppm) | 84 | 115 | 115 | 117 | 114 |
| Hydrogen flow (sccm) | 7.61 | 3.37 | 3.32 | 3.28 | 3.04 |
| Comonomer conc. (mol %) | 0.057 | 0.019 | 0.003 | 0.009 | 0.003 |
| C2 conc. (mol %) | 35.0 | 35.0 | 35.0 | 35.0 | 35.0 |
| Comonomer/C2 Flow Ratio | 0.007 | 0.003 | 0.003 | 0.003 | 0.003 |
| C2 flow (g/hr) | 587 | 647 | 632 | 646 | 608 |
| H2/C2 Ratio | 2.4 | 3.3 | 3.3 | 3.3 | 3.3 |
| Comonomer/C2 Ratio | 0.002 | 0.001 | 0.00007 | 0.00027 | 0.00007 |
| Rx. Pressure (psig) | 300 | 300 | 300 | 300 | 300 |
| Reactor Temp (F.) | 175 | 175 | 175 | 175 | 175 |
| Avg. Bedweight (g) | 1864 | 1881 | 1879 | 1910 | 1897 |
| Production (g/hr) | 313 | 457 | 472 | 446 | 432 |
| Residence Time (hr) | 6.0 | 4.1 | 4.0 | 4.3 | 4.4 |
| C2 Utilization (gC2/gC2 poly) | 1.87 | 1.42 | 1.34 | 1.45 | 1.41 |
| Avg Velocity (ft/s) | 1.57 | 1.56 | 1.56 | 1.55 | 1.56 |
| Catalyst Timer (minutes) | 15.0 | 45.0 | 45.0 | 45.0 | 43.0 |
| Catalyst Feed (g/hr) | 0.694 | 0.231 | 0.231 | 0.231 | 0.242 |
| Cat Prod. (g/g) - MB (new = .249) | 314 | 1377 | 1422 | 1343 | 1243 |
| Product Data | | | | | |
| Bulk Density | 0.4200 | 0.4038 | 0.4093 | 0.4057 | 0.3884 |
| Powder Flow Time | 6.81 | 7.88 | 7.34 | 7.15 | 6.81 |

TABLE 8A-continued

Summary of Process Data - resin density 0.95

| | Data Point | | | | |
|---|---|---|---|---|---|
| | 303-153 | 303-154 | 303-155 | 303-156 | |
| | | Example | | | |
| | 38 | 39 | 40 | 41 | 42 |
| | | Catalyst from Example | | | |
| | E | 17 | 18 | 19 | 20 |
| Total Production (grams) | 15531 | 33596 | 15131 | 13092 | 26301 |
| Number of Bedturnovers | 8.3 | 17.9 | 8.1 | 6.9 | 13.9 |
| Basic Resin Data | | | | | |
| MI | 1.32 | 0.92 | 0.81 | 0.37 | 0.21 |
| HLMI | 20.60 | 18.27 | 13.96 | 12.18 | 9.29 |
| HLMI/MI | 15.54 | 19.86 | 17.17 | 32.91 | 44.24 |
| Density | 0.9469 | 0.9467 | 0.9485 | 0.9497 | 0.9488 |

TABLE 8B

Summary of Resin Data - resin density 0.94

| | Product Data from Ex | | | | |
|---|---|---|---|---|---|
| | 38 | 39 | 40 | 41 | 42 |
| Resin 00270-157 | 020 | 030 | 040 | 050 | 060 |
| MI (ASTM, pellets) | 1.59 | 1.17 | 0.97 | 0.68 | 0.43 |
| HLMI (ASTM, pellets) | 29.50 | 19.00 | 16.80 | 14.40 | 10.97 |
| HLMI/MI (ASTM, pellets) | 18.55 | 16.24 | 17.32 | 21.18 | 25.51 |
| Density (ASTM, pellets) | 0.9505 | 0.9491 | 0.9514 | 0.9503 | 0.9512 |

The present inventors have found that the polymers produced by a catalyst system of the disclosure comprising a metallocene catalyst component and a non-metallocene catalyst component possess advantageous properties in comparison to polymer produced using the metallocene catalyst alone, and in comparison to conventional polymers.

As used herein, "melt strength" is defined as the force required to draw a molten polymer extrudate at a rate of 12 mm/s$^2$ and at an extrusion temperature (190° C. and 250° C. were used herein) until breakage of the extrudate whereby the force is applied by take up rollers. The polymer is extruded at a velocity of 0.33 mm/s through an annular die of 2 mm diameter and 30 mm length. Melt strength values reported herein are determined using a Gottfert Rheotens tester and are reported in centi-Newtons (cN). Additional experimental parameters for determining the melt strength are listed in Table 9. For the measurements of melt strength, the resins were stabilized with 500 ppm of Irganox 1076 and 1500 ppm of Irgafos168.

TABLE 9

Melt Strength test parameters

| Acceleration | 12 mm/s$^2$ |
|---|---|
| Temperature | 190.0° C. |
| Piston diameter | 12 mm |
| Piston speed | 0.4862 mm/s |
| Die diameter | 2 mm |
| Die length | 30 mm |
| Shear rate at the die | 70.0 s$^{-1}$ |
| Strand length | 125.0 mm |

TABLE 9-continued

Melt Strength test parameters

| Vo | 17.5 mm/s |
|---|---|
| Vs | 70.8 mm/s |

Figure 2:
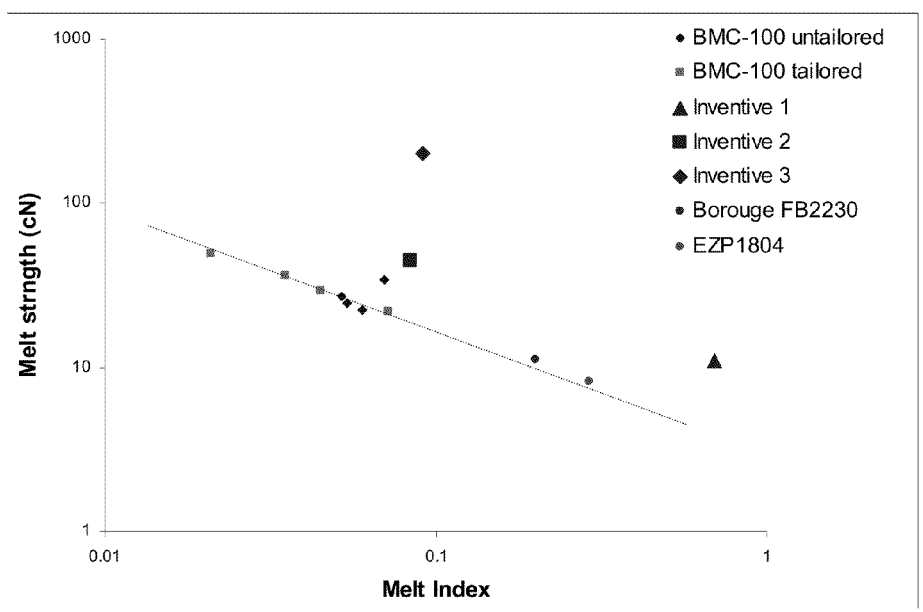
FIG. 2 provides a comparison of the melt strengths of non-limiting example resins of the disclosure and conventional resins having low MI.

FIG. 2 shows the melt strength of non-limiting inventive resins 1, 2, and 3 compared with several conventional resins having low MI (BMC-100 untailored, BMC-100 tailored, Borouge FB2230, and EZP 1804). As seen in FIG. 2, the melt strength of inventive resin 3 is an order of magnitude higher than that of linear or long chain branched polyethylenes of similar MI.

It is known in the art that when a polymer is subjected to uniaxial extension, the extensional viscosity of the polymer increases with strain rate. It is also known that the transient uniaxial extensional viscosity of a linear polymer can be predicted. "Strain hardening" occurs when a polymer is subjected to uniaxial extension and the transient extensional viscosity increases more than what is predicted from linear viscoelastic theory. As defined herein, the strain hardening index is the ratio of the observed transient uniaxial extensional viscosity ($\eta_E^+$ observed) to the theoretically predicted transient uniaxial extensional viscosity ($\eta_E^+$ predicted). Strain hardening index is expressed herein as the following ratio:

$$\eta_E^+\text{observed}/\eta_E^+\text{predicted}.$$

Figure 3:
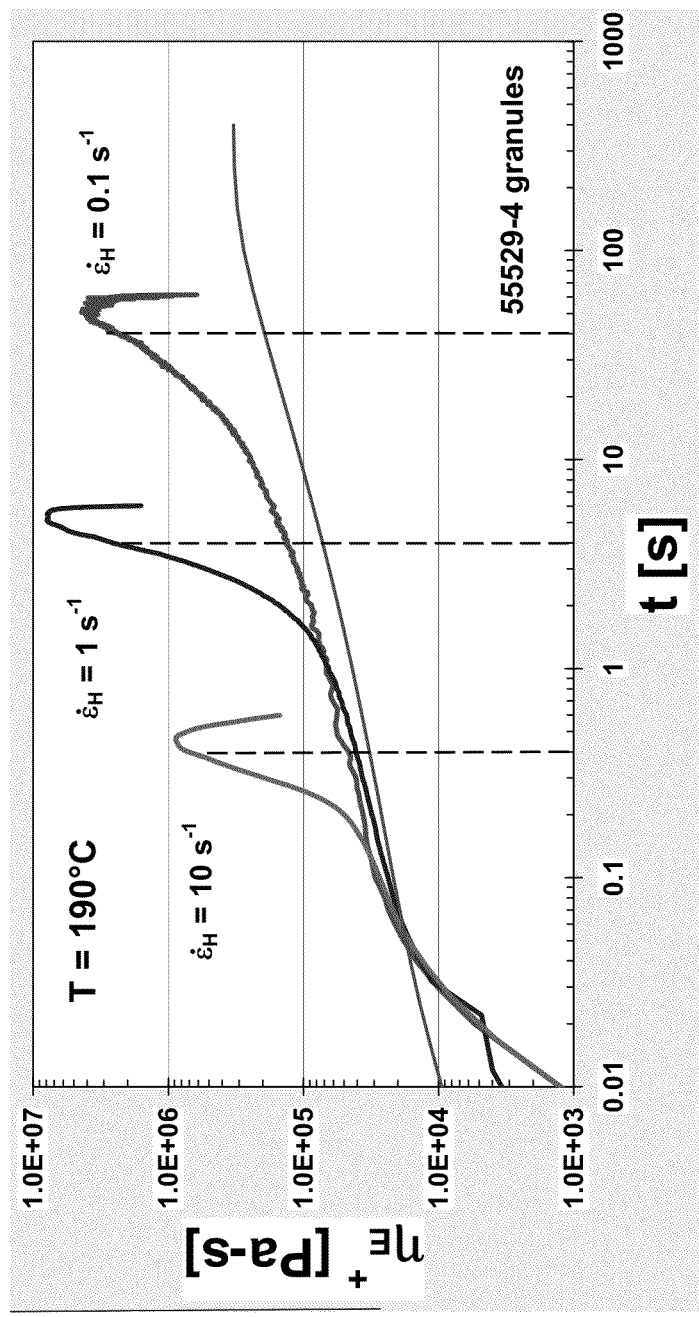
FIG. 3 depicts the transient uniaxial extensional viscosity of non-limiting example resin 3 of the disclosure as a function of time.

Referring now to FIG. 3 there is provided the extensional viscosity of inventive resin 3 at a function of time. At conditions characteristic of film blowing for example strain rate of 1 sec$^{-1}$, temperature of 190° C., and time of 4 seconds (i.e., a strain (ε) of 4), the strain hardening index of the polymers of the present disclosure is a value greater than 3 in some embodiments, a value greater than 5 in other embodiments, a value greater than 8 in even other embodiments, and a value greater than 10 in still other embodiments.

For extensional viscosity measurements, the resins were stabilized with 500 ppm of Irganox 1076 and 1500 ppm of Irgafos168. The transient uniaxial extensional viscosity was measured at temperatures of 150° C. and 190° C. and different strain rates, 0.1 sec$^{-1}$, 1.0 sec$^{-1}$, and 10 sec$^{-1}$. For example, the transient uniaxial extensional viscosity can be measured using a SER-HV-401 Testing Platform, which is commercially available from Xpansion Instruments LLC, Tallmadge, Ohio, USA. The SER Testing Platform was used on a Rheometrics ARES-LS rotational rheometer, which is available from TA Instruments. Inc., Newcastle, Del., USA. The SER Testing Platform is described in U.S. Pat. No. 6,578,413, which is incorporated herein by reference. A general description of transient uniaxial extensional viscosity measurements is provided, for example in, "Strain hardening of various polyolefins in uniaxial elongational flow", The Society of Rheology, Inc. J. Rheol. 47(3), 619-630 (2003); and "Measuring the transient extensional rheology of polyethylene melts using the SER universal testing platform", The Society of Rheology, Inc. J. Rheol. 49(3), 585-606 (2005), incorporated herein by reference.

Extensional rheology data from the Sentmanat Extensional Rhoemeter (SER) indicate the inventive resins show strain hardening behavior and extremely high transient uniaxial extensional viscosities (also referred to herein simply as "extensional viscosity"). FIG. 3 shows extensional viscosity of inventive resin 3 as a function of time. The reference line in FIG. 3 is the predicted linear viscoelastic envelop.

Figure 4:
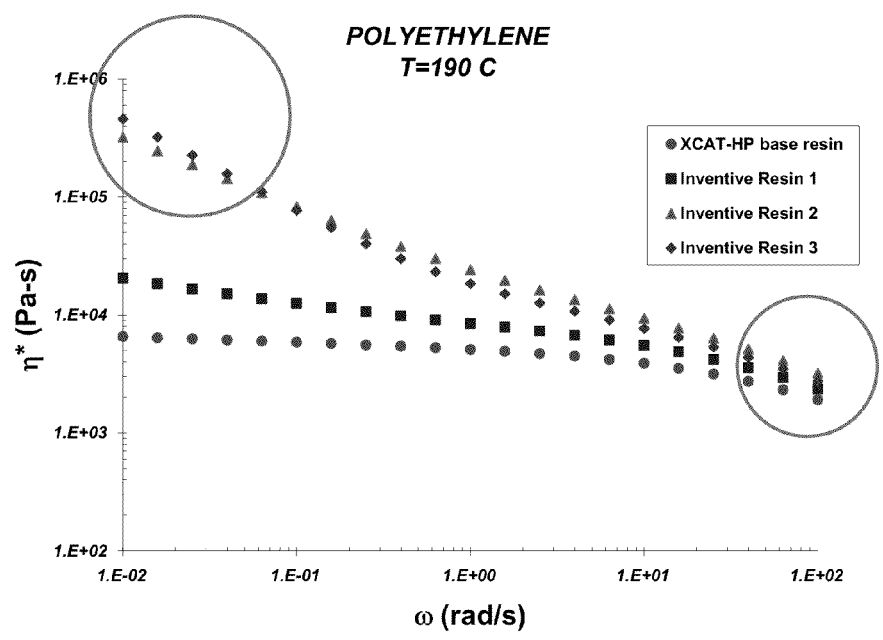
FIG. 4 provides a comparison of the shear thinning characteristics of a non-limiting example resin of the disclosure and a control resin.
Figure 5:
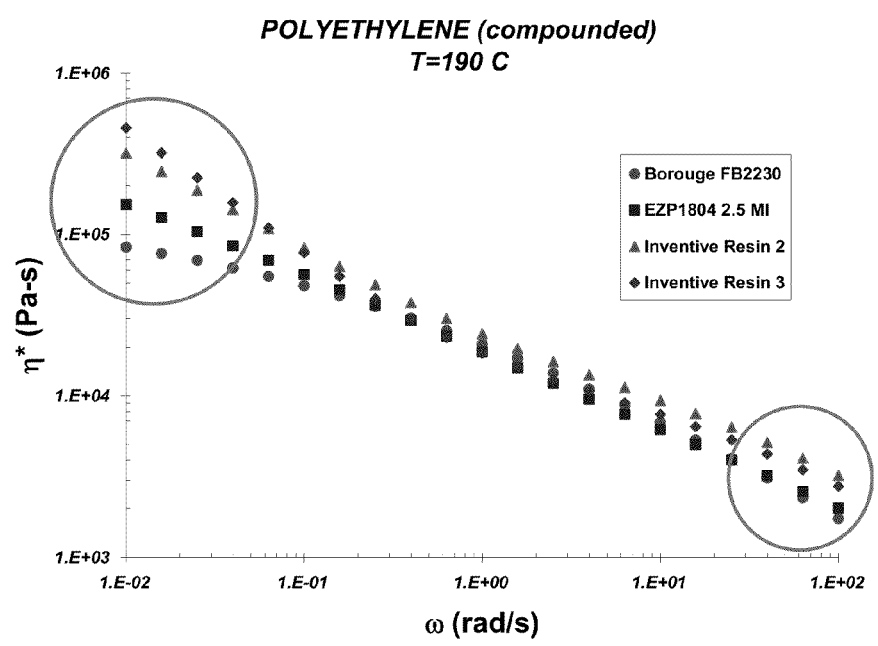
FIG. 5 provides a comparison of non-limiting example resins of the disclosure and conventional resins.

The inventive resins show strong shear thinning. They can be readily extruded but have very high viscosities at low shear rates, providing for the high melt strength. FIG. 4 shows the shear thinning characteristics of inventive resins 1, 2 and 3 compared to the XCAT-HP base resin. As can be seen in FIG. 4, the inventive resins have similar viscosities at high frequencies but much higher viscosities at low frequencies than the base resin (shear thinning) FIG. 5 compares inventive resins 1, 2, and 3 with conventional resins (Borouge FB2230 and EZP 1804), which show very high/strong shear thinning characteristics. As can be seen in FIG. 5, the inventive resins have similar viscosities at high frequencies but much higher viscosities at low frequencies than comparative resins (comparative resins already show very high shear thinning)

Figure 6:
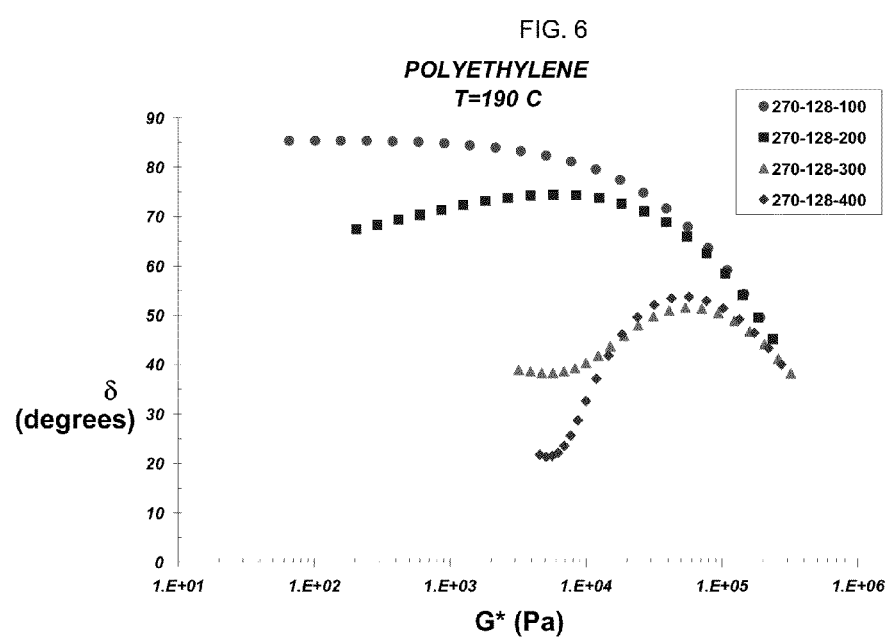
FIG. 6 provides a comparison of Van Gurp-Palmen plots of non-limiting example resins of the disclosure and a control resin.
Figure 7:
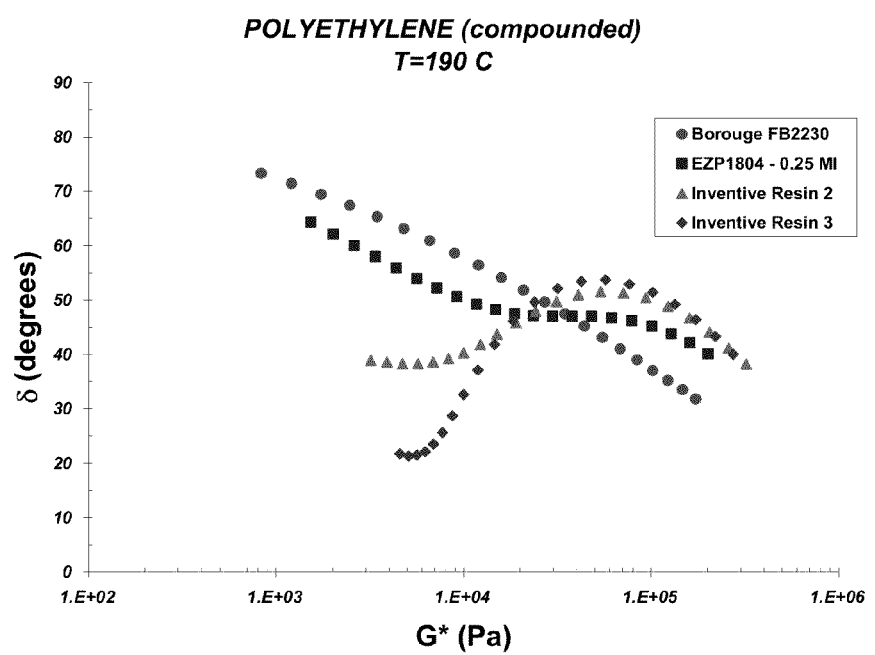
FIG. 7 provides a comparison of Van Gurp-Palmen plots of non-limiting example resins of the disclosure and conventional resins.

In FIG. 6, the Van Gurp-Palmen plots of non-limiting inventive resins 2 and 3 are shown in comparison with the HP-100 base resin. FIG. 7 shows a comparison of the van Gurp-Palmen plots of non-limiting inventive resins 2 and 3 and two conventional resins (Borouge FB2230 and EZP 1804). EZP1804 exhibits the signature of a highly branched long-chain LLDPE. Borouge 2230 is a commercial bimodal LLDPE that does not have long chain branches. Both conventional resins show the expected behavior.

Example 44

Film Products

Despite the high viscosities, the material could readily be made into film with good bubble stability. Blown films were made using Haake Rheomex 252P single screw extruder in connection with a Brabender blown film die. The extruder was equipped with a 19 mm (0.75 inch) metering screw that has a compression ratio 3:1. Ratio of screw diameter over length was 20:1. Output rate was about 3.5 lbs/hr. Additional film blowing parameters are provided in Table 10.

TABLE 10

| Film Blowing parameters Film Blowing Conditions | |
|---|---|
| Temperature Profile | |
| Zone 1 (° C.) | 185 |
| Zone 2 (° C.) | 185 |
| Zone 3 (° C.) | 195 |
| Die (° C.) | 200 |
| Melt Temperature (° C.) | 198 |
| Process Data | |
| Output (lb/h) | 3.5 |
| Head Pressure (psi) | 343 |
| Die Pressure (psi) | 2350 |
| Screw Speed (rpm) | 32 |
| Gauge (mils) | 1 |

Tables 11 and 12 provide some properties of non-limiting example films produced from resins of the disclosure.

TABLE 11

| Film Properties - Resin Density 0.93 | | | | | | | | | | |
|---|---|---|---|---|---|---|---|---|---|---|
| | Sample ID 00270-136 | | | | | | | | | |
| | -011 | -012 | -021 | -022 | -031 | -032 | -041 | -042 | -051 | -052 |
| Material: Films from resin example | 29 | 29 | 30 | 30 | 31 | 31 | 32 | 32 | 33 | 33 |
| MI | 1.25 | 1.254 | 1.10 | 1.10 | 0.91 | 0.91 | 0.73 | 0.73 | 0.09 | 0.089 |
| HLMI | 22.32 | 22.32 | 21.84 | 21.84 | 21.08 | 21.08 | 19.37 | 19.37 | 8.975 | 8.975 |
| MIR | 17.8 | 17.8 | 19.9 | 19.9 | 23.2 | 23.2 | 26.7 | 26.7 | 100.8 | 100.8 |
| Density | 0.928 | 0.928 | 0.929 | 0.929 | 0.930 | 0.930 | 0.931 | 0.931 | 0.929 | 0.929 |
| Film Properties | | | | | | | | | | |
| BUR | 2.2 | 3.2 | 2.2 | 3.2 | 2.2 | 3.2 | 2.2 | 3.2 | 2.2 | 3 |
| 1% Secant Modulus (psi) | | | | | | | | | | |
| MD | 37695 | 40501 | 45924 | 39999 | 47090 | 36373 | 48140 | 41123 | | |
| TD | 48655 | 46125 | 49548 | 54153 | 57231 | 52400 | 59120 | 49967 | | |

TABLE 11-continued

| | Film Properties - Resin Density 0.93 | | | | | | | | | |
|---|---|---|---|---|---|---|---|---|---|---|
| | Sample ID 00270-136 | | | | | | | | | |
| | -011 | -012 | -021 | -022 | -031 | -032 | -041 | -042 | -051 | -052 |
| Tensile Yield Strength (psi) | | | | | | | | | | |
| MD | 1847 | 1870 | 1946 | 2054 | 2061 | 1999 | 2109 | 2090 | | 1,998 |
| TD | 2091 | 2069 | 2268 | 2309 | 2461 | 2493 | 2395 | 2435 | | |
| Elongation @ Yield (%) | | | | | | | | | | |
| MD | 5.2 | 5.5 | 5.5 | 6 | 5.4 | 5.3 | 5.4 | 5.4 | | 5.7 |
| TD | 5.3 | 5.3 | 5.6 | 5 | 5.9 | 5.6 | 4.9 | 5.1 | | |
| Tensile Strength (psi) | | | | | | | | | | |
| MD | 6529 | 6601 | 5901 | 6675 | 6691 | 6757 | 7314 | 7197 | | 8,678 |
| TD | 6518 | 6579 | 6446 | 6840 | 6499 | 6637 | 5855 | 6837 | | |
| Elongation @ Break (%) | | | | | | | | | | |
| MD | 596 | 628 | 380 | 492 | 454 | 567 | 386 | 462 | | 165 |
| TD | 704 | 715 | 730 | 701 | 738 | 707 | 717 | 675 | | |
| Gloss (GU)* | | | | | | | | | | |
| MD | 74 | 67 | 62 | 55 | 60 | 51 | 37 | 33 | 18 | 15 |
| TD | 76 | 67 | 60 | 57 | 60 | 48 | 35 | 30 | 19 | 11 |
| Haze | 6 | 12.4 | 10.5 | 12.5 | 9.1 | 13.1 | 17.4 | 24.5 | 45.3 | 42.4 |
| Clarity | 97 | 96 | 84.7 | 86.7 | 87.2 | 84.5 | 70.5 | 73.3 | 40.2 | 35.5 |
| Transmittance | 92.6 | 92.6 | 92.6 | 92.7 | 92.6 | 92.8 | 92.5 | 74 | 91.9 | 92.2 |
| Internal Haze | 2.06 | 2.47 | 1.74 | 2.26 | 1.64 | 1.61 | 1.24 | 1.4 | 0.81 | 0.97 |
| Elmendorf Tear | | | | | | | | | | |
| MD (gms) | 35.06 | 56.16 | 21.84 | 18.56 | 19.8 | 42.28 | 14.86 | 24.74 | | |
| TD (gms) | 634.4 | 603.52 | 589.12 | 551.52 | 634.08 | 570.88 | 718.08 | 623.84 | | |
| MD (gms/mil) | 34 | 57 | 19 | 22 | 19 | 45 | 15 | 27 | | |
| TD (gms/mil) | 560 | 579 | 511 | 592 | 548 | 611 | 619 | 675 | | |
| Puncture | | | | | | | | | | |
| Peak Load (lbs) | 10.73 | 10.76 | 11.5 | 8.79 | 11.36 | 8.98 | 10.6 | 9.43 | | |
| Peak Force/mil (lbs/mil) | 8.94 | 10.06 | 9.5 | 9.66 | 9.62 | 8.89 | 9.46 | 10.14 | | |
| Break Energy (inch-lbs) | 17.98 | 23.49 | 14.79 | 14.88 | 15.67 | 14.44 | 14.74 | 16.14 | | |
| Break Energy/mil (inch-lbs/mil) | 14.98 | 21.96 | 12.22 | 16.35 | 13.28 | 14.29 | 13.16 | 17.36 | | |
| Dart Drop | | | | | | | | | | |
| gms | 119 | 115.5 | 117 | 84 | 87 | 70 | 90 | 484 | | |
| gms/mil | 99.17 | 107.94 | 96.69 | 92.31 | 73.73 | 69.31 | 80.36 | 90.3 | | |
| Shrink | | | | | | | | | | |
| MD | 87 | 80 | 89 | 88 | 90 | 88 | 89 | 86 | 88 | 85 |
| TD | −18 | 13 | −16 | 12 | −14 | 21 | −8 | 22 | 21 | 24 |
| FAR | −10 | −30 | −20 | −20 | −20 | −20 | −20 | | | |
| Gauge Mic (mils) | | | | | | | | | | |
| Average | 1.2 | 1.07 | 1.21 | 0.91 | 1.18 | 1.01 | 1.12 | 0.93 | 1.16 | 1.02 |
| Low | 0.95 | 0.84 | 1.05 | 0.6 | 0.96 | 0.56 | 0.89 | 0.6 | 0.51 | 0.54 |
| High | 1.68 | 1.41 | 1.69 | 1.2 | 1.49 | 1.55 | 1.35 | 0.93 | 1.71 | 1.38 |

TABLE 12

| | Film Properties - Resin Density 0.92 | | | | | | | |
|---|---|---|---|---|---|---|---|---|
| | Sample ID 00270 | | | | | | | |
| | -128-011 | -128-021 | 128-031 | -128-041 | -128-051 | -135-011 | -135-021 | -135-022 |
| Material: Films from resin example | 24 | 26 | 27 | 28 | commercial control Exceed 1018 CA | 1a | 1b | 1c |
| MI | 1.331 | 0.6933 | 0.0808 | 0.093 | | | 0.59 | 0.59 |
| HLMI | 22.17 | 13.97 | 5.5 | 5.3 | | | 13.54 | 13.54 |
| MIR | 16.66 | 20.15 | 68.07 | 56.99 | | | 22.95 | 22.95 |
| Density | 0.91707 | 0.91671 | 0.91721 | 0.91712 | | 0.91540 | 0.91636 | 0.91636 |

TABLE 12-continued

Film Properties - Resin Density 0.92

Sample ID 00270

| | -128-011 | -128-021 | 128-031 | -128-041 | -128-051 | -135-011 | -135-021 | -135-022 |
|---|---|---|---|---|---|---|---|---|
| Film Properties | | | | | | | | |
| BUR | | | | | | | 2.2 | 3.2 |
| Gauge (mil) | 1.41 | 1.31 | 1.09 | 0.92 | 1.25 | | | |
| Average | 1.27 | 1.18 | 0.80 | 0.72 | 0.97 | 0.99 | 0.96 | 0.80 |
| Low | 1.60 | 1.46 | 1.37 | 1.14 | 1.53 | 0.68 | 0.76 | 0.55 |
| High | | | | | | 1.27 | 1.13 | 1.21 |
| Elmendorf Tear | | | | | | | | |
| MD (g) | 315 | 128 | 24 | 36 | 384 | 218 | 32 | 62 |
| TD (g) | 567 | 690 | 755 | 603 | 396 | 331 | 410 | 395 |
| MD (g/mil) | 255 | 105 | 29 | 49 | 311 | 233 | 34 | 79 |
| TD (g/mil) | 451 | 591 | 797 | 674 | 333 | 369 | 416 | 540 |
| Dart Drop Mthd A | | | | | | | | |
| (g) | * | 301.5 | * | * | * | 288 | 249 | 225 |
| (g/mil) | * | 230 | * | * | * | 291 | 259 | 281 |
| Tensile & Elongation | | | | | | | | |
| Tensile @ Yield (psi) | | | | | | | | |
| MD | 1,129 | 1,170 | 1,622 | 1,308 | 1,227 | 1,086 | 1,290 | |
| TD | 1,244 | 1,352 | 1,520 | 1,420 | 1,317 | 1,132 | 1,227 | |
| Ultimate Tensile (psi) | | | | | | | | |
| MD | 8,404 | 8,235 | 10,139 | 9,593 | 9,218 | 8,046 | 8,793 | |
| TD | 8,191 | 8,955 | 9,025 | 8,402 | 9,428 | 8,814 | 7,329 | |
| Elongation @ Yield (%) | | | | | | | | |
| MD | 6.1 | 6.3 | 6.9 | 6.4 | 5.8 | 6.2 | 5.5 | |
| TD | 6 | 5.7 | 5.2 | 5.1 | 5.9 | 6.1 | 6.5 | |
| Break Elongation (%) | | | | | | | | |
| MD | 661 | 570 | 311 | 324 | 9218 | 636 | 559 | |
| TD | 668 | 622 | 622 | 609 | 9428 | 620 | 486 | |
| MD | 21,675 | 20,776 | 27,391 | 25,079 | 23,856 | 19,821 | 21,395 | |
| TD | 20,449 | 22,779 | 31,745 | 24,763 | 23,377 | 18,103 | 20,055 | |
| Puncture Mthd A | | | | | | | | |
| Peak Force (lb) | 15.2 | 15.7 | 10.8 | 14.2 | 12.0 | 9.4 | 11.6 | |
| Peak Force (lb/mil) | 10.8 | 12.0 | 9.9 | 15.4 | 9.6 | 9.5 | 12.1 | |
| Break Energy (in-lb) | 51.7 | 46.9 | 20.3 | 31.2 | 43.3 | 32.0 | 28.0 | |
| Break Energy (in-lb/mil) | 36.7 | 35.8 | 18.6 | 33.9 | 34.6 | 32.3 | 29.2 | |
| Internal Haze (%) | | | | | | | | |
| average value(%) | 2.62 | 0.91 | 0.64 | 0.76 | 5.42 | 1.06 | 1.08 | |
| Shrink (%) | | | | | | | | |
| MD | 62 | 81 | 87 | 89 | 30 | 47 | 84 | 81 |
| TD | 6 | -9 | 3 | 8 | 19 | 8 | 21 | 14 |
| GLOSS | | | | | | | | |
| MD | 47 | 67.7 | 12.5 | 19.8 | 9.4 | 44.5 | 42 | |
| TD | 46.6 | 70.1 | 14.5 | 16.8 | 9.6 | 42.6 | 37.6 | |
| Haze (%) | | | | | | | | |
| average value (%) | 13.9 | 6.03 | 50.5 | 41.1 | 66.9 | 15.0 | 16.6 | |

*exhausted sample and unable to obtain 10/10 ratio

The phrases, unless otherwise specified, "consists essentially of" and "consisting essentially of" do not exclude the presence of other steps, elements, or materials, whether or not, specifically mentioned in this specification, as along as such steps, elements, or materials, do not affect the basic and novel characteristics of the invention, additionally, they do not exclude impurities normally associated with the elements and materials used.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, within a range includes every point or individual value between its end points even though not explicitly recited. Thus, every point or individual value may serve as its own lower or upper limit combined with any other point or individual value or any other lower or upper limit, to recite a range not explicitly recited.

All priority documents are herein fully incorporated by reference for all jurisdictions in which such incorporation is permitted and to the extent such disclosure is consistent with the description of the present invention. Further, all documents and references cited herein, including testing procedures, publications, patents, journal articles, etc. are herein fully incorporated by reference for all jurisdictions in which such incorporation is permitted and to the extent such disclosure is consistent with the description of the present invention.

While the invention has been described with respect to a number of embodiments and examples, those skilled in the art, having benefit of this disclosure, will appreciate that other embodiments can be devised which do not depart from the scope and spirit of the invention as disclosed herein.

What is claimed is:

1. A catalyst system comprising:
a first catalyst component comprising a metallocene catalyst compound;
a second catalyst component having the following formula I:

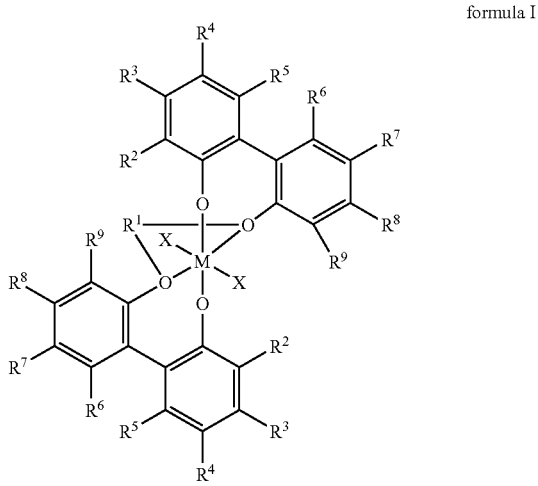

formula I wherein M is Zr;
wherein $R^1$ is selected from $CH_2CH_2$, $(CH_2)_3$, $(CH_2)_4$, $CH_2CHMeCH_2$, $CH_2CMe_2CH_2$;
wherein $R^2$ is a substituted aryl or a substituted heteroaryl;
wherein $R^4$ is selected from methyl, ethyl, propyl, butyl, and pentyl;
wherein $R^3$ and $R^5$ to $R^9$ are H; and
wherein X is selected from F, Cl, Br, I, benzyl, or $C_1$ to $C_5$ alkyls;
and optionally, a cocatalyst;
wherein said metallocene catalyst compound has a formula selected from the group consisting of $Cp^A Cp^B M'X'_n$, $Cp^A(A)Cp^B M'X'_n$, $Cp^A(A)QM'X'_n$ and $Cp^A M'Q_q X'_n$, wherein $Cp^A$ and $Cp^B$ are independently selected from the group consisting of cyclopentadienyl ligands and ligands isolobal to cyclopentadienyl, either or both $Cp^A$ and $Cp^B$ optionally contain heteroatoms, and either or both $Cp^A$ and $Cp^B$ may be substituted by one or more R groups, wherein M' is selected from the group consisting of Groups 3 through 12 atoms and lanthanide Group atoms, wherein X' is a leaving group, wherein n is 0 or an integer from 1 to 4, wherein A is selected from the group consisting of divalent alkyls, divalent lower alkyls, divalent substituted alkyls, divalent heteroalkyls, divalent alkenyls, divalent lower alkenyls, divalent substituted alkenyls, divalent heteroalkenyls, divalent alkynyls, divalent lower alkynyls, divalent substituted alkynyls, divalent heteroalkynyls, divalent alkoxys, divalent lower alkoxys, divalent aryloxys, divalent alkylthios, divalent lower alkyl thios, divalent arylthios, divalent aryls, divalent substituted aryls, divalent heteroaryls, divalent aralkyls, divalent aralkylenes, divalent alkaryls, divalent alkarylenes, divalent haloalkyls, divalent haloalkenyls, divalent haloalkynyls, divalent heteroalkyls, divalent heterocycles, divalent heteroaryls, divalent heteroatom-containing groups, divalent hydrocarbyls, divalent lower hydrocarbyls, divalent substituted hydrocarbyls, divalent heterohydrocarbyls, divalent silyls, divalent boryls, divalent phosphinos, divalent phosphines, divalent aminos, divalent amines, divalent ethers, and divalent thioethers; wherein Q is selected from the group consisting of heteroatom-containing ligands, $ROO^-$, $RO-$, $R(O)-$, $-NR-$, $-CR_2-$, $-S-$, $-NR_2$, $-CR_3$, $-SR$, $-SiR_3$, $-PR_2$, $-H$, and substituted and unsubstituted aryl groups; wherein R is selected from the group consisting of alkyls, lower alkyls, substituted alkyls, heteroalkyls, alkenyls, lower alkenyls, substituted alkenyls, heteroalkenyls, alkynyls, lower alkynyls, substituted alkynyls, heteroalkynyls, alkoxys, lower alkoxys, aryloxys, alkylthios, lower alkyl thios, arylthios, aryls, substituted aryls, heteroaryls, aralkyls, aralkylenes, alkaryls, alkarylenes, haloalkyls, haloalkenyls, haloalkynyls, heteroalkyls, heterocycles, heteroaryls, heteroatom-containing groups, hydrocarbyls, lower hydrocarbyls, substituted hydrocarbyls, heterohydrocarbyls, silyls, boryls, phosphinos, phosphines, aminos, amines, ethers, and thioethers; and wherein q is selected from 0 to 3; and
wherein said second catalyst component is present in an amount in a range of from about 0.001 to about 5.0 mol % relative to said first catalyst component.

2. The catalyst system of claim 1 wherein said second catalyst component is present in an amount in a range of from about 0.05 to about 2.5 mol % relative to said first catalyst component.

3. The catalyst system of claim 1 wherein said metallocene catalyst compound is selected from the group consisting of (Pentamethylcyclopentadienyl)(Propyl cyclopentadienyl)ZrX'$_2$, (Tetra methylcyclopentadienyl)(Propyl cyclopentadienyl)ZrX'$_2$, (Pentamethylcyclopentadienyl)(Butyl cyclopentadienyl)ZrX'$_2$, (Tetramethylcyclopentadienyl)(Butyl cyclopentadienyl)ZrX'$_2$, Me$_2$Si(Indenyl)$_2$ZrX'$_2$, Me$_2$Si(Tetrahydroindenyl)$_2$ZrX'$_2$, (n-propyl cyclopentadienyl)$_2$ZrX'$_2$, (n-propyl cyclopentadienyl)$_2$HfX'$_2$, (n-butyl cyclopentadienyl)$_2$ZrX'$_2$, (n-butyl cyclopentadienyl)$_2$HfX'$_2$, (1-Methyl, 3-Butyl cyclopentadienyl)$_2$ZrX'$_2$, HN(CH$_2$CH$_2$N(2,4,6-Me$_3$Phenyl))$_2$ZrX'$_2$, HN(CH$_2$CH$_2$N(2,3,4,5,6-Me$_5$Phenyl))$_2$ZrX'$_2$, (1-Me, 3-Bu-cyclopentadienyl)$_2$ZrCl$_2$, (Propyl cyclopentadienyl)(Tetramethylcyclopentadienyl)HfCl$_2$, (Butyl cyclopentadienyl)$_2$ZrCl$_2$, (Propyl cyclopentadienyl)$_2$ ZrCl$_2$, (Butyl cyclopentadienyl)$_2$HfCl$_2$, (Propyl cyclopentadienyl)$_2$HfCl$_2$, and any combinations thereof.

4. The catalyst system of claim 1 wherein $R^2$ is an aryl group with substituents in the 2 and 6 positions.

5. The catalyst system of claim 1 wherein each $R^1$ is either $(CH_2)_3$ or $(CH_2)_4$; each $R^2$ is selected from the group consisting of 2,6-Me$_2$Ph, 2,6-Et$_2$Ph, 2,6-Pr$_2$-Ph, 2,6-Bu$_2$Ph, 2-MeNapthyl, 2,4,6-Me$_3$Ph, 2,4,6-Et$_3$Ph, 2,4,6-Pr$_3$Ph, and carbazole; each R$^4$ is selected from the group consisting of Methyl and Butyl; and X is selected from the group consisting of F, Cl, and Me.

6. The catalyst system of claim 5 wherein R$^1$ is (CH$_2$)$_3$; each R$^2$ is either 2,4,6-Me3Ph or 2-MeNapthyl; each R$^4$ is CH$_3$; X is Cl.

7. The catalyst system of claim 1 wherein said cocatalyst includes an activator and, the catalyst system optionally includes a support.

8. The catalyst system of claim 7 wherein said activator is methylaluminoxane and said support is silica.

9. A method for making the catalyst system of claim 1 comprising: contacting in a diluent (a) the first catalyst component; and (b) the second catalyst component, and (c) a cocatalyst to form the catalyst system.

10. The method of claim 9 wherein said diluent is selected from the group consisting of pentane, isopentane, hexane, isohexane, heptane, octane, nonane, cyclopentane, cyclohexane, benzene, toluene, ethylbenzene and diethylbenzene.

11. A method for olefin polymerization comprising: contacting one or more olefin monomers with the catalyst system of claim 1 under olefin polymerization conditions to create a polyolefin, wherein said first catalyst component produces polymer having a weight average molecular weight (Mw) in the range of from 40,000 to 200,000 g/mol, and said second catalyst component produces polymer having an Mw of greater than 1,000,000 g/mol.

12. The method of claim 11 wherein said olefin monomers comprise ethylene, and optionally, hexene, butene, octene, or mixtures thereof.

13. The method of claim 11 wherein said olefin monomers further comprise at least one comonomer species selected from the group consisting of propylene, 1-butene, t-pentene, 1-hexene, 1-heptene, 1-octene, and combinations thereof.

14. The method of claim 11 wherein said contacting is in a gas-phase, slurry-phase or solution-phase reactor.

\* \* \* \* \*